US009636325B2

(12) United States Patent
Matson

(10) Patent No.: US 9,636,325 B2
(45) Date of Patent: May 2, 2017

(54) INDOLE LACTIC ACID OR A MIXTURE OF INDOLE LACTIC ACID AND INDOLE-3-PROPIONIC ACID FOR TREATMENT OF HUNTINGTON'S DISEASE

(71) Applicant: COUNTERPOINT HEALTH SOLUTIONS, INC., Bedford, MA (US)

(72) Inventor: Wayne R. Matson, Ayer, MA (US)

(73) Assignee: IXCELA, INC., Bedford, MA (US)

( * ) Notice: Subject to any disclaimer, the term of this patent is extended or adjusted under 35 U.S.C. 154(b) by 0 days.

(21) Appl. No.: 14/688,781

(22) Filed: Apr. 16, 2015

(65) Prior Publication Data

US 2015/0216845 A1    Aug. 6, 2015

Related U.S. Application Data

(62) Division of application No. 14/515,399, filed on Oct. 15, 2014, which is a division of application No. 14/092,677, filed on Nov. 27, 2013, which is a division of application No. 13/829,773, filed on Mar. 14, 2013.

(60) Provisional application No. 61/616,984, filed on Mar. 28, 2012.

(51) Int. Cl.
| | | |
|---|---|---|
| *A61K 31/405* | (2006.01) | |
| *A61K 38/16* | (2006.01) | |
| *G01N 33/68* | (2006.01) | |
| *G01N 33/483* | (2006.01) | |
| *G01N 33/49* | (2006.01) | |
| *G01N 33/493* | (2006.01) | |
| *A61K 47/48* | (2006.01) | |
| *G01N 33/52* | (2006.01) | |
| *A61K 38/00* | (2006.01) | |
| *A61K 35/741* | (2015.01) | |

(52) U.S. Cl.
CPC .......... *A61K 31/405* (2013.01); *A61K 35/741* (2013.01); *A61K 38/16* (2013.01); *A61K 47/48246* (2013.01); *G01N 33/483* (2013.01); *G01N 33/49* (2013.01); *G01N 33/492* (2013.01); *G01N 33/493* (2013.01); *G01N 33/528* (2013.01); *G01N 33/6812* (2013.01); *A61K 38/00* (2013.01); *G01N 2800/28* (2013.01); *G01N 2800/32* (2013.01)

(58) Field of Classification Search
None
See application file for complete search history.

(56) References Cited

U.S. PATENT DOCUMENTS

| | | | |
|---|---|---|---|
| 4,201,646 A | 5/1980 | Matson | 204/195 H |
| 4,233,031 A | 11/1980 | Matson et al. | 23/230 B |
| 4,288,303 A | 9/1981 | Matson | 204/105 R |
| 4,404,065 A | 9/1983 | Matson | 204/1 T |
| 4,497,199 A | 2/1985 | Matson | 73/61.1 C |
| 4,511,659 A | 4/1985 | Matson | 436/150 |
| RE32,920 E | 5/1989 | Matson et al. | 204/1 T |
| 4,863,873 A | 9/1989 | Matson | 436/63 |
| 5,104,639 A | 4/1992 | Matson | 424/2 |
| 5,501,836 A | 3/1996 | Myerson | 422/57 |
| 6,194,217 B1 | 2/2001 | Matson | 436/63 |
| 6,210,970 B1 | 4/2001 | Matson | 436/64 |
| 6,395,768 B1 | 5/2002 | Pappolla et al. | 514/415 |
| 6,475,799 B1 | 11/2002 | Matson | 436/8 |
| 6,548,252 B1 | 4/2003 | Matson | 435/6 |
| 6,558,955 B1 | 5/2003 | Kristal et al. | 436/63 |
| 6,585,937 B1 | 7/2003 | Matson | 422/69 |
| 7,214,486 B2 | 5/2007 | Matson | 435/6 |
| 7,297,481 B2 | 11/2007 | Matson | 435/6 |
| 7,972,781 B2 | 7/2011 | Matson | 435/6 |
| 2003/0207307 A1 | 11/2003 | Matson | 435/6.11 |
| 2004/0029830 A1 | 2/2004 | Hebert | 514/55 |
| 2005/0287197 A1 | 12/2005 | Kurtz | 424/450 |
| 2006/0008464 A1 | 1/2006 | Gilon | 424/185.1 |
| 2006/0018832 A1 | 1/2006 | Bates | 424/9.1 |
| 2007/0105937 A1 | 5/2007 | Pappolla et al. | 514/419 |
| 2008/0161228 A1 | 7/2008 | Ryals et al. | 514/2 |
| 2008/0207731 A1 | 8/2008 | Rogers | 514/419 |
| 2010/0144836 A1 | 6/2010 | Van Engeland et al. | 514/44 A |
| 2010/0172874 A1 | 7/2010 | Turnbaugh et al. | 424/93.4 |
| 2010/0317710 A1 | 12/2010 | Rogers | 514/419 |
| 2011/0010099 A1 | 1/2011 | Adourian et al. | 702/19 |
| 2011/0319387 A1 | 12/2011 | Schmidt et al. | 514/215 |
| 2012/0022234 A1 | 1/2012 | Bousquet-Gagnon et al. | 530/358 |
| 2012/0238028 A1 | 9/2012 | Reszka et al. | 436/71 |
| 2012/0258874 A1 | 10/2012 | Narain et al. | 506/8 |
| 2013/0267469 A1 | 10/2013 | Matson | 514/16.4 |
| 2013/0330824 A1 | 12/2013 | Li | 435/375 |

FOREIGN PATENT DOCUMENTS

| | | | |
|---|---|---|---|
| CN | 1292693 | 4/2001 | A61K 31/403 |
| EP | 2218792 | 8/2010 | C12Q 1/68 |
| WO | WO2005036180 | 4/2005 | G01N 33/68 |
| WO | WO2008024914 | 2/2008 | A61K 31/405 |
| WO | WO2013012332 | 1/2013 | C12Q 1/10 |

(Continued)

OTHER PUBLICATIONS

Smith, Microb Ecol. 1997; 33: 180-188.*
Poeggler et al., Brain Research, 1999; 815: 382-388.*
Burns et al., J Psychopharmacol. 2006; 20: 732-55.*
Vickers, Drugs Aging, 2002, 19(7): 487-494.*
Borovecki et al., PNAS, 2005; 102: 11023-11028.*
Hall et al., Neurotherapeutics. Jan. 2010;7(1):51-61; doi: 10.1016/j.nurt.2009.10.021.*

(Continued)

*Primary Examiner* — Christina Borgeest
(74) *Attorney, Agent, or Firm* — Hayes Soloway P.C.

(57) ABSTRACT

Indole-3-propionic acid as a marker and for treatment for Huntington Disease.

3 Claims, 28 Drawing Sheets

(56) References Cited

FOREIGN PATENT DOCUMENTS

WO    WO2013148709    10/2013    ............ A61K 31/405

OTHER PUBLICATIONS

Haes et al., Detection of a Biomarker for Alzheimer's Disease from Synthetic and Clinical Samples Using a Nanoscale Optical Biosensor, Journal of American Chemical Society, Jan. 27, 2005, vol. 127, No. 7, pp. 2264-2271 (8 pgs).
International Search Report and Written Opinion issued in application PCT/US15/13888, dated Jul. 24, 2015 (12 pgs).
M. Nic, J. Jirat, B. Kosata, "coordination" Aug. 19, 2012. IUPAC. Compendium of Chemical Terminology, $2^{nd}$ ed. (the Gold Book). Compiled by A. D. McNaught and A. Wilkinson. Blackwell Scientific Publications, Oxford, 1997, updates compiled by A. Jenkins (2 pgs).
M. Nic, J. Jirat, B. Kosata, "covalent bond" Aug. 19, 2012. IUPAC. Compendium of Chemical Terminology, $2^{nd}$ ed. (the Gold Book). Compiled by A. D. McNaught and A. Wilkinson. Blackwell Scientific Publications, Oxford, 1997, updates compiled by A. Jenkins (2 pgs).
Office Action issued in U.S. Appl. No. 14/092,677, dated Jul. 23, 2015 (17 pgs).
Office Action issued in U.S. Appl. No. 14/321,569, dated Jul. 20, 2015 (38 pgs).
Bendheim et al., "Development of indole-3-propionic acid (OXIGON) for Alzheimer's disease," J Mol Neurosci. Aug.-Oct. 2002;19(1-2):213-7. Review. PMID (5 pgs).
Bird et al., "Structural characterization of plasma metabolites detected via LC-electrochemical coulometric array using LC-UV fractionation, MS, and NMR," Anal. Chem. Nov. 20, 2012;84(22):9889-98. doi: 0.1021/ac302278u. Epub Nov. 6, 2012 (10 pgs).
Bogdanov et al., "Increased Oxidative Damage to DNA in ALS Patients," Free Radical Biology & Medicine. Oct. 1, 2000; 29(7): 652-658 (7 pgs).
Bogdanov et al., "Metabolomic profiling to develop blood biomarkers for Parkinson's disease," Brain. Feb. 2008; 389-396 (8 pgs).
Chyan et al., "Potent Neuroprotective Properties against the Alzheimer β-Amyloid by an Endogenous Melatonin-related Indole Structure, Indole-3-propionic Acid," Journal of Biological Chemistry. Jul. 30, 1999; 274(31): 21937-21942 (6 pgs).
Ebbel et al., "Identification of Phenylbutyrate-Generated Metabolites in Huntington Disease Patients using Parallel LC/EC-array/MS and Off-line Tandem MS," Anal Biochem. Apr. 15, 2010; 399(2): 152-161 (20 pgs).
El-Ansary et al., "Biomarker Discovery in Neurological Diseases: A Metabolomic Approach," Open Access Journal of Clinical Trials, Nov. 30, 2009, vol. 1, pp. 27-41 (15 pgs).
Hwang et al., Indole-3-propionic acid attenuates neuronal damage and oxidative stress in the ischemic hippocampus. J Neurosci Res. Jul. 2009;87(9):2126-37. doi: 10.1002/jnr.22030. PMID: 19235887 [PubMed—indexed for MEDLINE] (12 pgs).
International Search Report and Written Opinion issued in corresponding application No. PCT/US2013/033918, dated Jun. 14, 2013 (15 pgs).
International Search Report and Written Opinion issued in related application No. PCT/US14/45139, dated Nov. 10, 2014 (10 pgs).
Johansen, et al., "Metabolomic Profiling in *LRRK2*-Related Parkinson's Disease," PLoS ONE. Oct. 2009; 4(10): e7551 (9 pgs).
Kaddurah-Daouk et al., "Metabolomic changes in autopsy confirmed Alzheimer's disease," Alzheimers Dement. May 2011; 7(3): 309-317 (14 pgs).
Kaddurah-Daouk et al., "Pretreatment metabotype as a predictor of response to sertraline or placebo in depressed outpatients: a proof of concept," Transl Psychiatry. Jul. 26, 2011; 1(7): e26 (7 pgs).
Karbownik et al., "Carcinogen-induced, free radical-mediated reduction in microsomal membrane fluidity: reversal by indole-3-propionic acid," J Bioenerg Biomembr. Feb. 2001;33(1):73-8. PMID: 11460928 [PubMed—indexed for MEDLINE] (6 pgs).
Karbownik et al., "Comparison of potential protective effects of melatonin, indole-3-propionic acid, and propylthiouracil against lipid peroxidation caused by potassium bromate in the thyroid gland," J Cell Biochem. May 1, 2005;95(1):131-8. PMID: 15723291 [PubMed—indexed for MEDLINE] (8 pgs).
Kato et al., "Analytical method for β-amyloid fibrils using CE-laser induced fluorescence and its application to screening for inhibitors of β-amyloid protein aggregation," Anal Chem. Jul. 1, 2007;79(13):4887-91. Epub May 31, 2007 (5 pgs).
LeWitt et al., "Markers of dopamine metabolism in Parkinson's disease," The Parkinson Study Group. Neurology, Nov. 1992;42(11):2111-7 (7 pgs).
Nam et al., "Melatonin protects against neuronal damage induced by 3-nitropropionic acid in rat striatum," Brain Research. 2005: 90-96 (7 pgs).
Office Action issued in related U.S. Appl. No. 13/829,773, dated Aug. 20, 2014 (33 pgs).
Office Action issued in related U.S. Appl. No. 13/829,773, dated Mar. 6, 2015 (25 pgs).
Office Action issued in related U.S. Appl. No. 14/092,677, dated Mar. 27, 2015 (26 pgs).
Office Action issued in related U.S. Appl. No. 14/515,399, dated Apr. 2, 2015 (31 pgs).
Pauley et al., "Effect of Tryptophan Analogs on Derepression of the *Escherichia coli* Tryptophan Operon by Indole-3-Propionic Acid," Journal of Bacteriology, Oct. 1978, vol. 136, No. 1, pp. 219-226 (8 pgs).
Preliminary Report on Patentability; Appln. No. PCT/US2013/033918, dated Oct. 1, 2014, (12 pgs).
Rozen et al., "Metabolomic analysis and signatures in motor neuron disease," Metabolomics. 2005; 1(2): 101-108 (14 pgs).
Schiavo et al., "Metabolite Identification Using a Nanoelectrospray LC-EC-array-MS Integrated System," Anal Chem. Aug. 1, 2008; 80(15): 5912-5923 (21 pgs).
Sitorius, E., "Development of Fourier Transform Mid-Infrared Spectroscopy as a Metabolomic Technique for Characterizing the Protective Properties of Grain Sorghum Against Oxidation," May 1, 2010, Dissertations & Theses in Food Science and Technology, Digital Commons at the University of Nebraska, Lincoln (94 pgs).
Thomas et al., "A novel method for detecting 7-methyl guanine reveals aberrant methylation levels in Huntington disease", Anal Biochem, May 15, 2013;436(2):112-20. doi: 10.1016/j.ab.2013.01.035. Epub Feb. 12, 2013 (19 pgs).
Wikoff et al., "Metabolomics analysis reveals large effects of gut microflora on mammalian blood metabolites," PNAS. Mar. 10, 2009; 106(10): 3698-3703 (6 pgs).
Anderson, George, "Quantitation of tryptophan metabolites in rat feces by thin-layer chromography", *Journal of Chromatography*, 105 (1975) 323-328 (6 pgs).
Bumb et al., "Macromolecular and Dendrimer Based Magnetic Resonance Contrast Agents," NIH Public Access Author Manuscript, 2010, pp. 1-28 (28 pgs).
Crider et al., Folate and DNA Methylation: A Review of Molecular Mechanisms and the Evidence for Folate's Role, Advances in Nutrition, 2012, 3, 21-38 (18 pgs).
Extended European search report issued in application No. 13768233.2, dated Dec. 22, 2015 (15 pgs).
Gurova, K., "New hopes from old drugs: revising DNA-binding small molecules as anticancer agents," NIH Public Access, Author Manuscript, 2009, 1-28 (28 pgs).
International Preliminary Report on Patentability issued in application No. PCT/US2014/045139, dated Jan. 14, 2016 (9 pgs).
Office Action issued in U.S. Appl. No. 13/829,773, dated Feb. 8, 2016 (16 pgs).
Office Action issued in U.S. Appl. No. 14/092,677, dated Dec. 10, 2015 (13 pgs).
Office Action issued in U.S. Appl. No. 14/321,569, dated Jan. 26, 2016 (21 pgs).
Office Action issued in U.S. Appl. No. 14/515,399, dated Mar. 1, 2016 (19 pgs).
Office Action issued in U.S. Appl. No. 14/610,779, dated Dec. 22, 2015 (48 pgs).

(56) References Cited

OTHER PUBLICATIONS

Poeggeler et al., "Indole-3-propionate: a potent hydroxyl radical scavenger in rat brain", Brain Research, Elsevier, 815 (1990) 382-388 (7 pgs).
Yang et al., "Effects of High Tryptophan Doses and Two Experimental Rations on the Excretion of Urinary Tryptophan Metabolites in Cattle" The Journal of Nutrition, 102: 1655-1666, 1972 (11 pgs).
Yoshida et al., "Direct Enrichment of Tryptophan and Its Metabolites in Plasma onto a Pre-column Followed by Reverse Phase HPLC Analysis," Chem Pharm Bull, 1982; 30: 3827-3830 (4 pgs).
Bertini et al., The Metabonomic Signature of Celiac Disease, Journal of Proteome Research 2009, vol. 8, pp. 170-177 (8 pgs).
Chinese Office Action issued in application No. 201380023926.6, dated May 31, 2016 (9 pgs).
Gordis, L., Epidemiology, Second Edition, 2000 WB Saunders Company, Chapter 4, "Assessing the Validity and Reliability of Diagnostic and Screening Tests," pp. 63-80 (19 pgs).
Lopez-Otin et al., The Hallmarks of Aging, Cell, 2013, 153, 1194-1217 (24 pgs).
Office Action issued in U.S. Appl. No. 14/092,677, dated Apr. 14, 2016 (33 pgs).
Office Action issued in U.S. Appl. No. 14/321,569, dated Jun. 6, 2016 (21 pgs).
Office Action issued in U.S. Appl. No. 14/610,779, dated Jun. 14, 2016 (33 pgs).
Office Action issued in U.S. Appl. No. 14/828,204, dated Apr. 22, 2016 (36 pgs).
Office Action issued in U.S. Appl. No. 14/828,211, dated May 19, 2016 (36 pgs).
Office Action issued in U.S. Appl. No. 14/828,211, dated May 5, 2016 (6 pgs).
Rahman, K., Studies on free radicals, antioxidants, and co-factors, Clinical Interventions in Aging, 2007 2(2), 219-236 (18 pgs).
Valko et al., Free radicals, metals and antioxidants in oxidative stress-induced cancer, Chemico-Biological Interactions, 2006, 160, 1-40 (40 pgs).
Yara et al., Iron-Ascorhate-Mediated Lipid Peroxidation Causes Epigenetic Changes in the Antioxidant Defense in Intestinal Epithelial Cells: Impact on Inflammation, PLOS One, 2013, (8(5), 1-11 (11 pgs).
Chinese Office Action issued in application No. 201380023926.6, dated Sep. 22, 2015 (9 pgs).
Chung, MCM, "Structure and Function of Transferrin," 1984, Biochemical Education, vol. 12, issue 4, pp. 146-154 (9 pgs).
European Office Action issued in application No. 13768233.2, dated Oct. 27, 2015 (7 pgs).
Office Action issued in U.S. Appl. No. 13/829,773, dated Sep. 11, 2015 (14 pgs).
Office Action issued in U.S. Appl. No. 14/092,677, dated Sep. 11, 2015 (12 pgs).
Office Action issued in U.S. Appl. No. 14/321,569, dated Sep. 18, 2015 (21 pgs).
Office Action issued in U.S. Appl. No. 14/515,399, dated Sep. 8, 2015 (23 pgs).
Office Action issued in U.S. Appl. No. 14/610,779, dated Oct. 9, 2015 (20 pgs).
Smith et al., "Formation of Phenolic and Indolic Compounds by Anaerobic Bacteria in the Human Large Intestine," Microbial Ecology, vol. 33, No. 3, Apr. 1997, pp. 180-188 (9 pgs).
Tandara et al., "Iron metabolism: current facts and future decisions," 2012, Biochemica Medica, vol. 22, issue 3, pp. 311-328 (14 pgs).
Hall et al., "Antioxidant Therapies for Traumatic Brain Injury," Neurotherapeutics: The Journal of the American Society for Experimental NeuroTherapeutics, vol. 7, Jan. 2010, pp. 51-61 (11 pgs).
International Preliminary Report on Patentability issued in application No. PCT/US2015/013888, dated Aug. 11, 2016 (9 pgs).
Mattson, M., "Excitotoxic and Excitoprotective Mechanisms," NeuroMolecular Medicine, vol. 3, 2003, pp. 65-94 (30 pgs).
Williams et al., "Serum Metabolic Profiling in Inflammatory Bowel Disease," Dig Dis Sci, Apr. 10, 2012, vol. 57, pp. 2157-2165 (9 pgs).
U.S. Appl. No. 13/829,773, filed Mar. 14, 2013, Matson.
U.S. Appl. No. 14/092,677, filed Nov. 27, 2013, Matson.
U.S. Appl. No. 14/515,399, filed Oct. 15, 2014, Matson.
U.S. Appl. No. 14/321,569, filed Jul. 1, 2014, Matson.
U.S. Appl. No. 14/610,779, filed Jan. 30, 2015, Matson.
U.S. Appl. No. 14/828,204, filed Aug. 17, 2015, Matson.
U.S. Appl. No. 14/828,211, filed Aug. 17, 2015, Matson.
U.S. Appl. No. 15/277,861, filed Sep. 27, 2016, Matson.
Notice of Allowance issued in U.S. Appl. No. 14/092,677, dated Nov. 8, 2016 (18 pgs).
Office Action issued in U.S. Appl. No. 13/829,733, dated Nov. 3, 2016 (24 pgs).
Office Action issued in U.S. Appl. No. 14/828,204, dated Nov. 16, 2016 (16 pgs).
Office Action issued in U.S. Appl. No. 14/828,211, dated Nov. 25, 2016 (14 pgs).
Rosas et al., "A systems-level "misunderstanding": the plasma metalolome in Huntington's disease", Annals of Clinical and Translational Neurology, Open Access, dated Apr. 11, 2015, pp. 756-768.
Blech et al., "The Metabolism and Disposition of the Oral Direct Thrombin Inhibitor, Dabigatran, In Humans," 2008; 36: 386-399 (14 pgs).
Caudle et al., "Using 'omics' to define pathogenesis and biomarkers of Parkinson's disease," Expert Review of Neurotherapeutics, vol. 10, No. 6, Jun. 1, 2010, pp. 925-942 (29 pgs).
Cook et al., Pharmacokinetics and Metabolism of [$^{14}$C]eplerenone After Oral Administration to Humans, 2003; 31:1448-1455 (8 pgs).
European Search Report issued in application 14820565.1, dated Feb. 6, 2017 (10 pgs).
Mellick et al., "Exploiting the potential of molecular profiling in Parkinson's disease: current practice and future probabilities," Expert Review of Molecular Diagnostics, vol. 10, No. 8, Nov. 1, 2010, pp. 1035-1050 (16 pgs).
Office Action issued in U.S. Appl. No. 14/321,569, dated Jan. 23, 2017 (17 pgs).
Office Action issued in U.S. Appl. No. 14/515,399, dated Jan. 25, 2017 (24 pgs).
Waldmeier et al., "Absorption, Distribution, Metabolism, and Elimination of the Direct Renin Inhibitor Aliskiren in Health Volunteers," 2007; 35: 1418-1428 (11 pgs).

\* cited by examiner

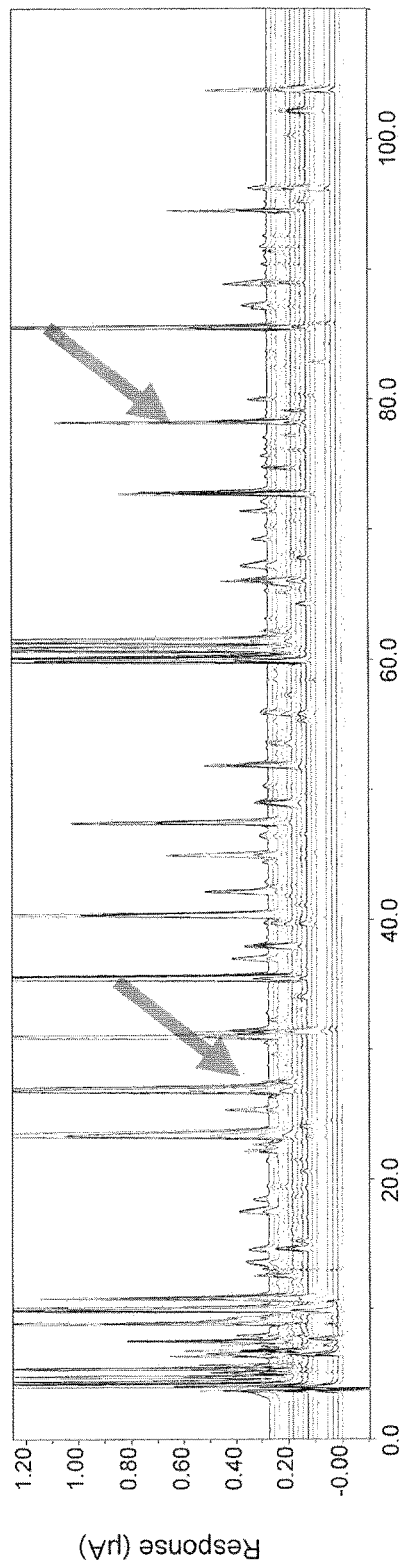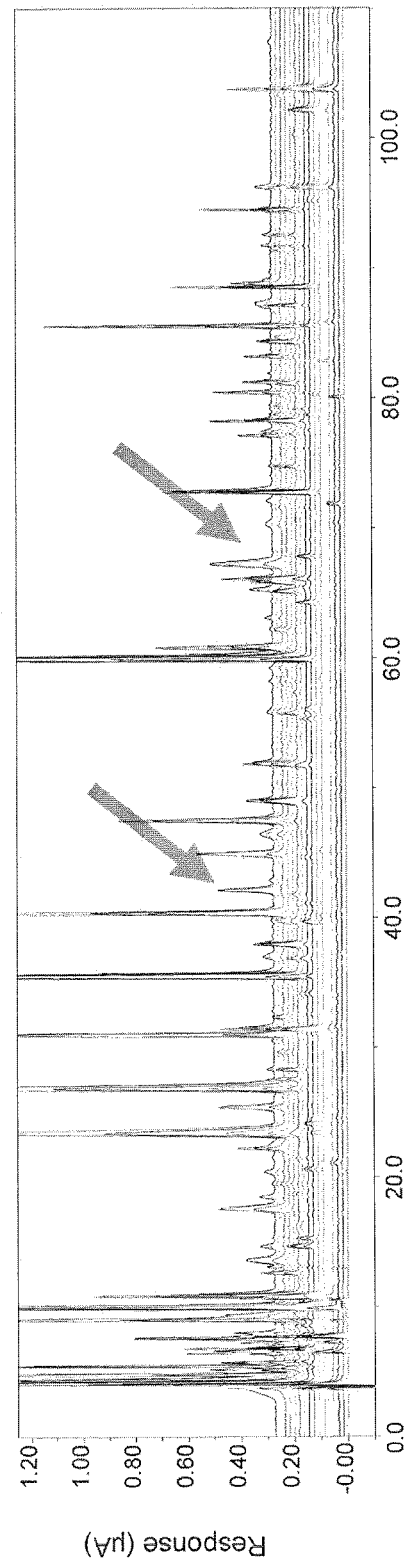

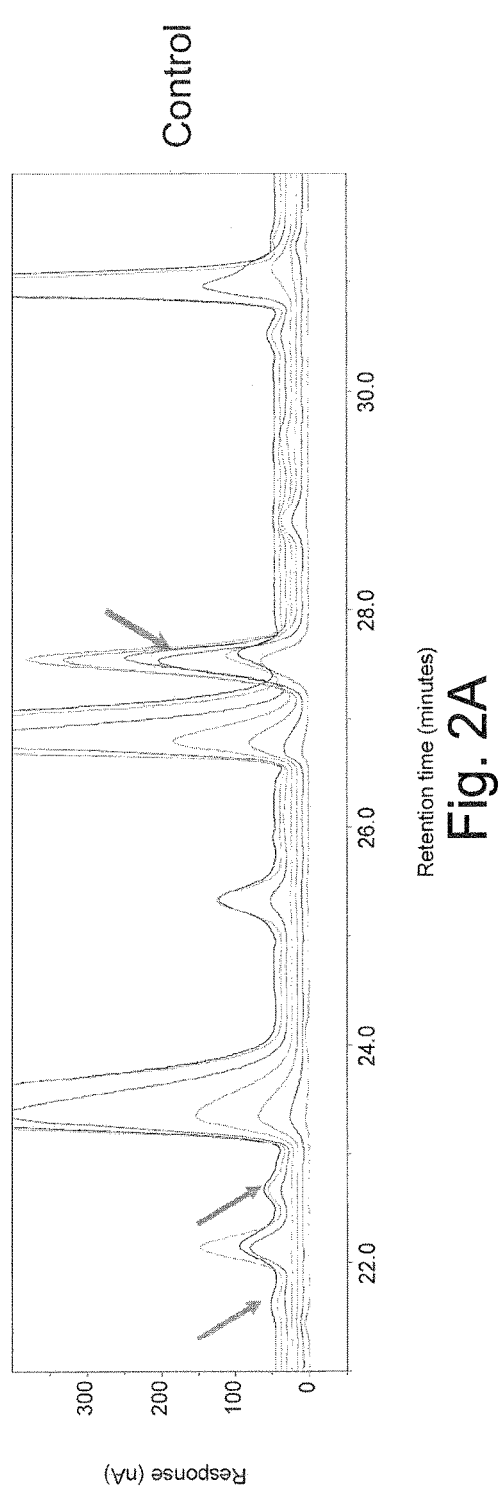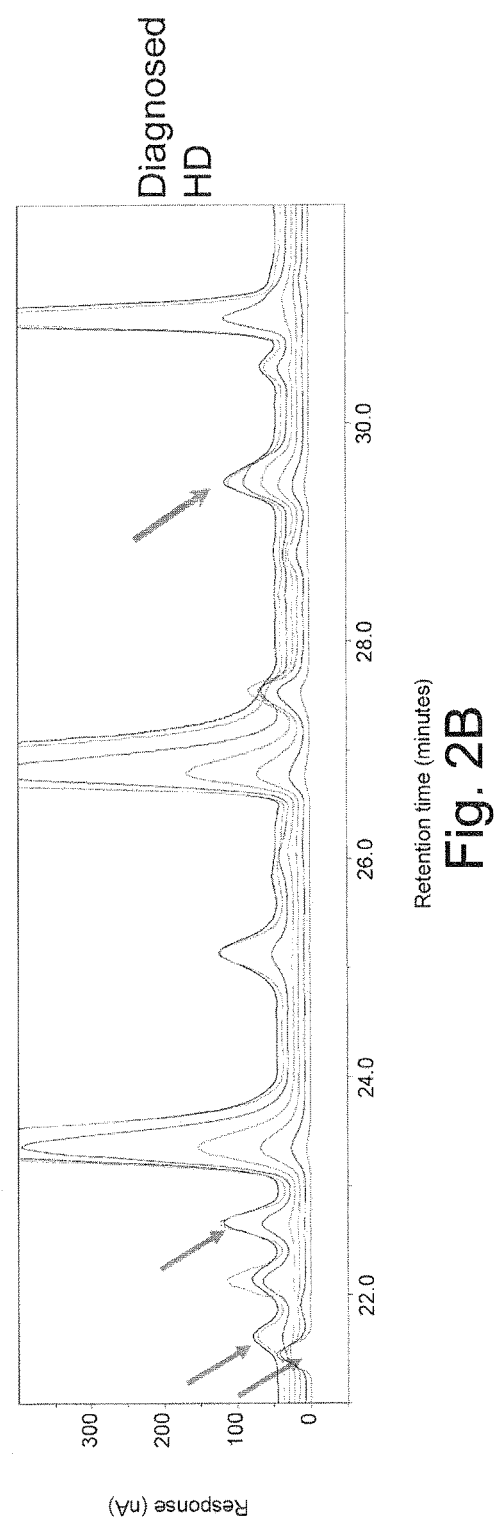

| | CH-RT | CX10647 10/21/04 | CX104 11/30/04 | CX84 2/3/05 | CX105 1/25/05 | CX99 2/7/08 | CC23 8/8/07 | CC25 12/7/06 | CC63 7/3/05 | CC27 8/8/07 | CC21 1/23/08 | AVERAGE Crest | AVERAGE Controls |
|---|---|---|---|---|---|---|---|---|---|---|---|---|---|
| 45151 | 11-78.000 | 2 | 52687 | 169 | 31 | 331 | 2994 | 909 | -284 | 1203 | 3038 | 3933 | 3024 |
| 45152 | 11-78.025 | 198 | 24953 | 480 | 272 | 731 | 15474 | 4051 | 2298 | 6135 | 11729 | 4647 | 4935 |
| 45153 | 11-78.05 | 702 | 11134 | 1261 | 1107 | 2051 | 51457 | 14237 | 13165 | 22335 | 36713 | 7072 | 12821 |
| 45154 | 11-78.075 | 1709 | 4477 | 2979 | 2860 | 4796 | 134589 | 39943 | 39500 | 65412 | 96777 | 12837 | 29239 |
| 45155 | 11-78.1 | 3437 | 2420 | 6122 | 5891 | 9422 | 201967 | 91580 | 99360 | 156700 | 169630 | 24495 | 61377 |
| 45156 | 11-78.125 | 5370 | 3134 | 10762 | 10380 | 13502 | 530433 | 174150 | 203160 | 399910 | 263387 | 42411 | 111042 |
| 45157 | 11-78.15 | 8240 | 8122 | 16132 | 15639 | 20403 | 837700 | 250030 | 345837 | 507767 | 306390 | 65462 | 172845 |
| 45158 | 11-78.175 | 10917 | 15715 | 20751 | 20334 | 26622 | 1046100 | 370035 | 495300 | 605300 | 510167 | 86978 | 229341 |
| 45159 | 11-78.2 | 12612 | 22091 | 23190 | 23140 | 30139 | 1150867 | 434133 | 620167 | 805300 | 566567 | 99668 | 261910 |
| 45160 | 11-78.225 | 12667 | 22958 | 22809 | 22695 | 29822 | 1197767 | 481767 | 627500 | 905900 | 550300 | 98466 | 258528 |
| 45161 | 11-78.25 | 11199 | 20747 | 19952 | 19574 | 26098 | 954700 | 374633 | 522500 | 816033 | 498633 | 85272 | 221791 |
| 45162 | 11-78.275 | 8922 | 16399 | 15675 | 15238 | 20493 | 730167 | 259037 | 423900 | 739439 | 302067 | 66016 | 177970 |
| 45163 | 11-78.3 | 6500 | 11531 | 11203 | 10942 | 14637 | 507367 | 202473 | 301227 | 589233 | 279700 | 46631 | 121299 |
| 45164 | 11-78.325 | 4405 | 8611 | 7409 | 7438 | 9652 | 324720 | 131567 | 199400 | 421300 | 184570 | 30803 | 78752 |
| 45165 | 11-78.35 | 2846 | 5128 | 4611 | 4931 | 5999 | 195057 | 81107 | 123377 | 276417 | 112257 | 19572 | 48475 |
| 45166 | 11-78.375 | 1823 | 2748 | 2739 | 3321 | 3595 | 119110 | 48867 | 74063 | 170027 | 65133 | 12338 | 29065 |
| 45167 | 11-78.4 | 1226 | 1281 | 1555 | 2397 | 2094 | 71537 | 29030 | 44073 | 101727 | 39640 | 7927 | 17494 |
| 45168 | 11-78.425 | 913 | 686 | 818 | 1917 | 1161 | 44543 | 19231 | 26773 | 60497 | 23347 | 5274 | 10927 |
| 45169 | 11-78.45 | 758 | 191 | 363 | 1671 | 594 | 29000 | 13341 | 16971 | 37241 | 14899 | 3657 | 7289 |
| 45170 | 11-78.475 | 667 | 2 | 97 | 1505 | 296 | 16830 | 10002 | 11310 | 24323 | 10094 | 2668 | 5215 |
| 45171 | 11-78.5 | 563 | -25 | -21 | 1338 | 303 | 15577 | 8083 | 7800 | 15350 | 7169 | 2053 | 4043 |

Fig. 3

Early Disease State Compared to Controls

VIP List

| Channel | Time (min) |
|---|---|
| 7 | 35.4 (highest in PS13, lower in C) |
| 7 | 56.75 (highest in HD13, lower in PS13 and C) |
| 9 | 88.75 (highest in PS13, lower in C) |
| 15 | 18.0 (highest in PS13) |
| 15 | 37.0 (highest in PS13, lower in C and HD13) |

Late Disease State Compared to Controls

Early Disease State Compared to Late State Disease

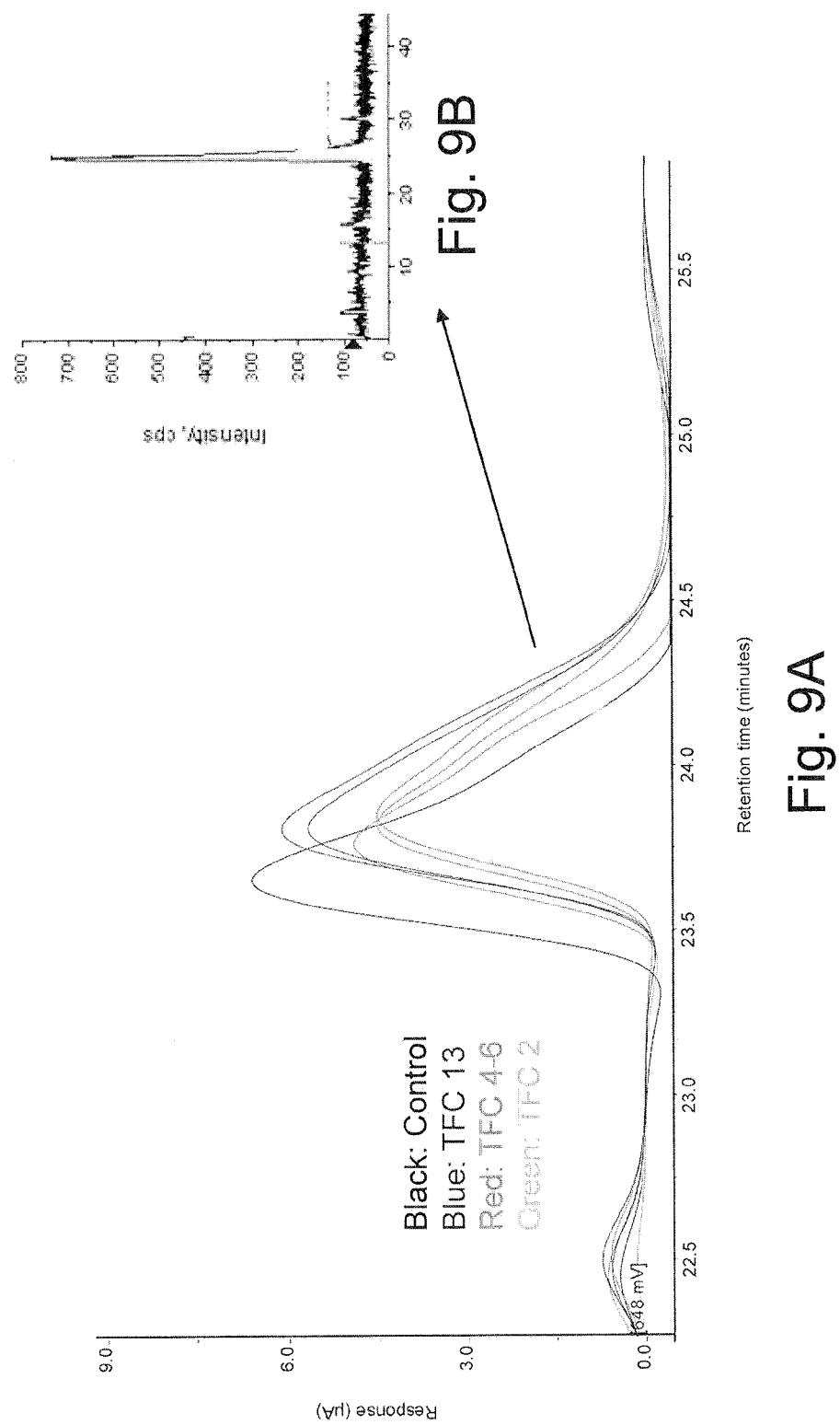

I3PA → Indolyl cation radical intermediate → Kynuric Acid

Oxidation of I3PA

Representation of a PK digested fragment

▲ = Oxidation product of I3PA

|  |  | BRAIN | | PLASMA | | FECES | | URINE |
| --- | --- | --- | --- | --- | --- | --- | --- | --- |
|  |  | IPA | IPAM | IPA | IPAM | IPA | IPAM | peak 1&2 sum uQ |
| IPAM dosed R6/2 |  | pg/mg | pg/mg | ng/ml | ng/ml | pg/mg | pg/mg | nM/ml |
|  | MIPAM10 | 36.34 | 1.71 | 1738.84 | 9.27 | 26734.25 | 21916.58 | 16.18 |
|  | MIPAM3 | 51.01 | 2.16 | 1001.09 | 14.54 | 36782.75 | 6660.25 | 16.78 |
|  | MIPAM4 | 41.40 | 1.28 | 1765.43 |  |  |  | 14.61 |
|  | MIPAM5 | 48.40 | 1.22 | 1894.76 | 6.44 | 8375.38 | 23332.13 | 14.61 |
|  | MIPAM6 | 46.92 | 1.27 | 2023.56 | 10.50 | 14465.50 | 14953.58 | 34.17 |
|  | MIPAM7 | 45.76 | 3.99 | 1630.28 | 11.03 | 6494.00 | 802.07 | 11.65 |
|  | MIPAM9 | 30.98 | 5.60 | 960.30 | 7.72 | 6574.63 | 1335.50 | 21.70 |
| R6/2 mouse |  |  |  |  |  |  |  |  |
|  | MV1 | 2.15 | 0.33 | 71.26 | 0.13 |  |  | 1.70 |
|  | MV10 | 2.18 | 0.12 | 80.47 | 2.68 | 1077.00 | 19.83 | 1.70 |
|  | MV2 | 2.21 | 0.05 | 98.12 | 0.13 | 1825.50 | 7.30 | 1.36 |
|  | MV3 | 1.74 | 0.05 | 136.65 | 3.17 | 2011.32 | 7.65 | 1.26 |
|  | MV4 | 2.69 | 0.05 | 119.79 | 3.00 | 1243.81 | 2.96 | 1.31 |
|  | MV6 | 1.79 | 0.68 | 42.90 | 1.85 | 762.08 | 9.48 | 1.83 |
|  | MV7 | 2.37 | 1.04 | 32.69 | 2.71 | 785.28 | 1.57 | 1.93 |
|  | MV9 | 1.20 | 0.10 | 31.61 | 0.19 | 1179.33 | 0.00 | 0.52 |
| WILD TYPE |  |  |  |  |  |  |  |  |
|  | MWT1 | 2.82 | 0.32 | 100.56 | 0.98 | 1157.18 | 3.07 | 3.40 |
|  | MWT2 | 3.08 | 0.05 | 171.53 | 0.13 | 2151.56 | 7.46 | 4.39 |
|  | MWT5 | 1.99 | 0.05 | 168.53 | 2.65 | 775.75 | 5.22 | 4.04 |
|  | MWT7 | 4.17 | 0.05 | 185.59 | 1.93 | 1754.88 | 0.15 | 2.57 |
|  | MWT8 | 5.50 | 0.81 | 285.73 | 2.42 | 1641.11 | 0.19 | 3.51 |
|  | MWT9 | 4.48 | 0.91 | 185.73 | 0.84 | 805.29 | 10.35 | 2.39 |
| wild type av. |  | 3.674 | 0.364 | 182.946 | 1.490 | 1380.959 | 4.406 | 3.38 |
| R6/2 av |  | 2.026 | 0.298 | 77.462 | 1.962 | 1269.190 | 6.970 | 1.42 |
| ttest p |  | 0.022 | 0.848 | 0.007 | 0.638 | 0.460 | 0.274 | 7.36413E-05 |
| PEARSON r |  |  |  |  |  |  |  |  |
| urine vs. brain all |  | 0.860 |  |  |  |  |  |  |
| urine vs. brain undosed |  | 0.500 |  |  |  |  |  |  |
| urine vs. plama all |  | 0.863 |  |  |  |  |  |  |
| urine vs. plasma undosed |  | 0.627 |  |  |  |  |  |  |

Fig. 30

INDOLE LACTIC ACID OR A MIXTURE OF INDOLE LACTIC ACID AND INDOLE-3-PROPIONIC ACID FOR TREATMENT OF HUNTINGTON'S DISEASE

CROSS REFERENCE TO RELATED APPLICATION

This application is a divisional of U.S. application Ser. No. 14/515,399, filed Oct. 15, 2014, which application in turn is a divisional of U.S. application Ser. No. 14/092,677 filed Nov. 27, 2013, which in turn is a divisional of U.S. application Ser. No. 13/829,773, filed Mar. 14, 2013, which claims priority from U.S. Provisional Application Ser. No. 61/616,984, filed Mar. 28, 2012, the contents of which are incorporated herein by reference.

BACKGROUND OF THE INVENTION

The present disclosure relates to the use of indole-3-propionic acid (hereinafter "IPA" or "I3PA") as a therapeutic agent, as a protective agent against late onset of cardiovascular and neurodegenerative disease, and as a biomarker for disease and health conditions. The disclosure has particular utility in connection with neurodegenerative diseases such as Huntington Disease (HD), Alzheimer Disease (AD), Mild Cognitive Impairment (MCI), Lower Motor Neuron Disease (MND) including but not limited to Amyotrophic Lateral Sclerosis (ALS), Parkinson's Disease (PD) as well as hypertension, stroke and ischemic heart disease and head injury, and will be described in connection with such utilities, although other utilities are contemplated.

IPA is an indole produced in organisms such as *c. Sporogenes* that have the enzyme to remove the OH from the 2 position on the propionic acid side chain of indole lactic acid an end product of tryptophan metabolism in mammalian species. It is one of several gut metabolites that affect the plasma metabolome [12]. Other organisms such as brewers yeast also show the ability to produce IPA (See below a means of producing purified IPA preparations using brewers yeast or similar organisms). Current understanding is that IPA serves as an antioxidant whose intermediate indoxyl positive free radical, unlike such compounds as tocopherols and carotenes has no pro oxidant intermediates [11,14,15, 17] and in vitro has been shown to suppress protein aggregation and suggested as a therapeutic for Alzheimer's Disease [13,16,18]. IPA also has been shown in culture studies to suppress other microbial species such as *E. coli* (Pauley et. al. Effect of Tryptophan analogs on depression of the *Enchiridia Coli* Tryptophan Operon by Indole 3 propionic Acid: Journal of Bacteriology 219-226 (1978). We have shown that in plasma IPA is strongly bound to plasma proteins both albumin and immunoglobulins with normal plasma levels of ca. 200 ng/ml and free levels of ca. 0.1 ng/ml. The loading capacity of plasma for IPA is approximately 10 ug/ml before significant additional loading shows linearity of free material with added material. In plasma loading studies IPA replaces other indoles such as 3 hydroxy kynurenine and 3 hydroxy anthranillic acid which are thought to have possible deleterious effects on protein. We have shown that on free radical attack the intermediate positive ion free radical binds to protein as a kynuric acid moiety. The displacement of other indoles, the strong coordinate binding to protein and the defense of the protein against free radical attack leaving a residue that does not lead to crosslinking and denaturation are mechanisms that provide protection and improve functionality of an organism. We have shown that IPA produced in the gut enters the plasma and crosses the BBB and is found in brain and CSF. Residual fecal levels are lower than plasma levels and indicate that the majority of IPA produced is transferred to plasma. Intra peritoneal injected IPA derivative such as the amide (IPAM) are rapidly converted to IPA in the plasma. We also have identified two metabolites of IPA that allow monitoring of levels in excretion samples such as urine which correlate with plasma and brain levels.

Many late onset illnesses of the CNS or cardiovascular system have characteristics of free radical damage reflected in reduction of protective agents such as tocopherols, ascorbate etc. and damage products of lipids proteins and DNA. Different approaches to controlling this aim at different structures and processes—Antioxidants such as CoQ10 to reduce DNA damage and protect mitochondrial function, selected lipid diets to reduce lipid oxidation, materials such as creatine to enhance energy efficiency and reduce free radical burden, ascorbate to provide general peripheral protection. CNS disorders such as MCI, AD and HD and to a more limited extent PD and ALS also involve protein aggregation-currently considered to be the proximal cause of neuronal death in Huntington's disease, Alzheimer's disease and other neurodegenerative disorders. Specific agents to prevent damage to proteins have not been as extensively studied. These commonalties in late onset disease lead to the concept that there is a failure of control of the biochemical system reflecting the interaction and feedback among the genome transcriptome, proteome metabolome environment and commensal gut microbiome. It is this failure of feedback that in fact is the disease and that leads eventually to the symptoms. Consequently one looks for places in the network where genetic or environmental changes have created a non lethal but sub optimal level of control. These nodes or compounds can then be evaluated as therapeutics or as risk factors that like cholesterol for instance can be modified to reset or reestablish control.

We have shown in animal models and in human studies that the individuals genome determines the aggregate composition of the commensal gut microbiome and consequently the levels of I3PA produced in the gut. I3PA levels are then to an extent an inherited characteristic and low levels that are present in neurodegenerative and cardiovascular disease constitute an inherited characteristic that place individuals at higher risk for these diseases. Increasing these levels by supplementation and/or by modification of the aggregate makeup of the commensal gut microbiome is thus and approach to reducing risk as well as a therapeutic approach to intervention when such risk has been realized in the development of symptoms of disease.

SUMMARY OF THE DISCLOSURE

The network of biochemical interactions in an individual is determined by the individual genome, the effect of the individuals genome on the individuals commensal microflora and the feed back among the genome, transcriptome, proteome, metabolome, microbiome and environment. In this control network there are individual compounds and genes that constitute potential risk factors that can be modified to improve the probability of not developing late onset diseases caused by non lethal but sub optimal control. A well known example is cholesterol that is both genetically and environmentally determined.

We have discovered that IPA levels are individual specific indicators of risk factor for certain diseases. More particularly, we have identified decreased levels of IPA in individuals suffering from neurodegenerative diseases (Huntington's Disease (HD), Presymptomatic HD, Alzheimer's disease (AD) and Mild Cognitive Impairment (MCI), Lower Motor Neuron Disease (LMND), Amyotropic Lateral Sclerosis (ALS), Parkinson's disease (PD)) and in hypertension stroke and individuals with ischemic heart disease, and have also shown that IPA is decreased in ischemic heart disease subjects undergoing mental and/or physical stress tests.

We have shown that IPA levels are not impacted over the short term by SSRI or antihypertensive drugs. Data from studies with serial samples show that IPA is a highly specific individual specific characteristic (FIG. 29). We have shown that IPA levels are related to the genomic makeup of the individual through the effect of the individual's genome on the aggregate genome of the gut microbiome and that levels are highly constant in an individual in the absence of intervention or possible development of certain disease states of the gut (FIG. 29). The individual specificity of IPA levels, the genomic relationship, the prevalence of low levels in numerous disorders and particularly the progression of sequentially lower levels in normal individuals, individuals with MCI and individuals with AD indicate that it is a genetically determined risk factor for the development such late onset disorders as neurodegenerative diseases and hypertension and ischemic heart disease. The reason for low IPA levels can thus be both genetic and environmental including different diet and stress situations of an individual. Since it is inherently easier to influence the aggregate genome of the gut microbiome than the genetic make up of an individual, we propose therapeutic intervention to reduce risk using IPA as a marker by focusing on directly increasing IPA levels or modification of the gut to increase IPA levels. Since IPA is related to the composition of the gut microbiome we developed techniques to show that genetic modification of mice creates a unique associated microbiome indicating that inherent levels of IPA are dependent to on the genetic modification. We also have shown that the microbiome reflected in the foot print of the organisms in fecal material is an individual specific characteristic of human subjects.

Thus, we have found that low IPA like high Cholesterol is innately an inherited risk factor for disease that should be monitored and adjusted by therapeutic supplementation or gut microbiome modification in the population with low IPA levels as a whole.

We also have determined that in certain traumas such as stroke which significantly reduces IPA levels in CSF and plasma, or potential traumas such as military combat or high intensity contact sports IPA supplementation will provide a protective effect against protein and oxidative damage occurring as sequelae.

We also discovered that IPA level monitoring advantageously may be used in drug development. Trials of a therapeutic agent are expensive at all phases from initial animal studies to phase 1, 2 and 3 trials in humans. In animal trials minimizing the number of animal cohorts will reduce expenses considerably which can be achieved by using new technologies with micro techniques of analysis and by analysis of total patterns of metabolomic interactions that reduce the need to sacrifice animals for dose finding and pharmacokinetic studies.

In phase 1 safety and tolerability and dose finding similar processes can be used to develop baseline individual biochemical patterns of differences in metabolism of the therapeutic agent and its metabolites and overall biochemical patterns and network relationships. Such archived data from phase 1 studies provides the baseline for possible specification of outcome or possible contra indication In phase 2 trials use of non invasive biomarkers can be used for more complete assessment of compliance and continuation of the acquisition of the archived data will provide again insight into specification and adverse effects and indications of adjunctive therapeutics or processes reverse such affects.

In phase 3 assessing compliance with non invasive biomarkers will allow the better assessment of therapeutic outcome and verify or validate any biomarkers or biochemical anomalies that are contraindicated in the use of a therapeutic agent.

A common persistent problem in assessing body burden in animal trials of a therapeutic agent and in assessing compliance in human trials is providing means of non invasive monitoring of levels of the therapeutic or effects of an intervention. A second potential problem is in developing an initial set of multiple metabolites and changes in the overall metabolomic network that may have individual specific or group deleterious effects.

The process of developing markers of therapeutic intervention for monitoring and potential deleterious markers involves an initial step of loading a test animal or human individual with the compound of interest and subsequently performing serial global metabolomic profiling tests of urine saliva and plasma and feces (or with mice of serial urine plasma feces and subsequently brain, cord and other organs. The profiles are analyzed by total pattern matching not only to determine traditional pharmacokinetics but also to detect and identify any metabolites of the compound and any changes in the overall self similarity and endogenous compounds or compound relationships. Typically metabolomic profiles are measured for coordinately bound compounds yielding ca 1500-2000 responses. Protocols for analyzing unknown compounds of statistical significance have been developed. Following the use of global metabolic profiling according to the teaching above rapid targeted methods are developed to: (1) allow rapid minimally or non invasive monitoring or compounds of significance in drug trials, and (2) allow population wide monitoring of compounds related to risk factors of disease for potential modification and risk reduction.

As an example we have developed a system for assessing the levels of IPA in both animal and human samples of spot urine 5-10 ul and or finger stick whole blood 20-50 ul. Monitoring in urine is possible because of the discovery of two electro active metabolites of IPA in dosing studies in R6/2 mice (See FIG. 30) from which we isolated and determined two peaks (FIG. 25), as will be discussed below. Using coulometric sensor technology we are able to determine the total coulombs and number of electrons involved in oxidation of the materials as 1. This allows direct determination of the moles of material excreted and assessment of the body burden of the material. The levels of these peaks correlate with levels of plasma in the mice. The same metabolites occur in human subjects and correlate with plasma IPA. The assay can be done on liquid spot urine or more conveniently on urine dried on filter paper normalizing the values of the metabolites to creatinine or to the total integrated electroactive species in the sample. The filter paper approach can be generalized to any metabolites of any compound that may be studied.

The advantage of the discovery of these metabolites in animal studies is that it allows the monitoring of a test cohort without any sacrifice of the animals in the initial steps of determining dose loading and the following steps of assessing actual drug levels during survival and behavioral studies.

In human trials urinary measurements and/or use of finger stick blood samples either alone or taken to filter paper matrix offer a means of monitoring both compliance and adsorption of various formulations. Such methods also offer a convenient protocol for acquisition of samples for risk assessment of levels of compounds such as IPA by an individual in the home environment to reduce the costs of monitoring on a population wide basis.

As well as providing a system for monitoring in direct supplementation or therapeutic use of a compound this protocol also allows tracking of protocols to modify the gut microbiome directed at increasing the levels of potentially beneficial compounds such as IPA or decreasing the levels of potentially harmful compounds such as cresoles or benzoates.

Further this rapid targeted protocol allows the development of a procedure for evaluating the levels of IPA in prior archived profiles and sample sets across a range of neurological diseases and studies where it had previously not been structurally identified prior to our work in concentrating and identifying the peak with a concentration and parallel LCEC/LCMS protocol.

The following is a protocol that we have developed suitable for evaluation of IPA by an individually acquired sample to enable determination of IPA levels; to determine if increased levels would put the individual into a lower risk category and to supply and monitor strategies for increasing IPA levels by supplementation, gut microflora modification or dietary modification.

The kit contains 4 strips of high absorbent filter paper labeled AM fasting urine, AM fasting Blood, PM non fasting urine, PM non fasting blood in individual color coded accession numbered zip lock bags in an insulated shipping kit with a small ice pack. In the morning the individual takes a mid stream urine sample to the filter paper labeled AM fasting urine and a finger stick blood sample to the filter paper labeled AM fasting blood, placing the samples in the appropriate zip lock bags in the shipping kit. In the evening the individual takes a mid stream urine sample to the filter paper labeled PM non fasting Urine and a finger stick sample to the filter paper labeled PM non fasting blood placing the samples in the shipping kit. The shipping kit is then mailed to the laboratory.

Urinary levels of IPA metabolites and blood levels of IPA are determined from the samples provided and a report based on the sample accession number is sent to the mailing address. The report identifies the quintile of the individuals IPA level and the relative risk associated with that level. If indicated the report will suggest appropriate supplements and or modifications to raise IPA levels. These may include direct ingestion of IPA at suggested specified levels in preparations of purified free IPA, IPA bound to protein or bound to inert materials such Froximum (inorganic ash supplement), or activated charcoal, and/or suggested modifications of diet. The effectiveness of the supplements or modifications will be evaluated using a second test kit after a period of 4-8 weeks.

In certain instances IPA levels may be greater than the mean control levels by over 3 standard deviations. In prior work we have seen such levels in cases of gut disorders such as Celiac disease, Diverticulitis, or leaky gut syndrome. High IPA as such is not a diagnostic for these disorders but is an indicator that they or other gut microbiome abnormalities may be present. In cases where such levels are found no supplementation would be suggested but rather a suggestion of possible follow up with medical professionals.

Our animal model and human studies indicate that IPA is best adsorbed through the gut and optimally IPA preparations should reach the gut before becoming available. This can be accomplished by encapsulation and/or by providing the IPA in a form coordinately bound to protein or bound coordinately to an inorganic inert matrix. The coordinately bound forms of which are not easily released by HCl at concentrations in the stomach.

Consider Huntington Disease (HD) as an example. (HD) is a debilitating neurodegenerative disease characterized by gradual onset motor dysfunction, dementia, weight loss and emotional disturbances. HD is inherited in an autosomal dominant fashion and occurs in approximately 5-10 cases per 100,000 individuals [1,2]. It manifests itself in all races and ethnic groups [3]. Currently, in North America, approximately 30,000 individuals are affected by HD and it is likely that close to 150,000 others may develop the condition. Although the age of onset varies from infancy to the early eighties, the average age of onset is in the late thirties. The disease progresses over the course of several years in affected individuals, eventually preventing these individuals from functioning independently.

Occasionally especially when the onset of symptoms occurs before age 20, choreic movements are less prominent; instead bradykinesia and dystonia predominate. As the disorder progresses, the involuntary movements become more severe, dysarthria and dysphagia develop, and balance is impaired. The cognitive disorder manifests first as slowness of mental processing and difficulty in organizing complex tasks. Memory is impaired, but affected persons rarely lose their memory of family, friends, and the immediate situation. Such persons often become irritable, anxious, and depressed. Less frequently, paranoia and delusional states are manifest. The outcome of HD is invariably fatal; over a course of 15-30 years, the affected person becomes totally disabled and unable to communicate, requiring full-time care; death ensues from the complications of immobility.

Unfortunately there is currently no therapy proven to delay onset or to slow progression of the disease, although efforts are being made to develop more effective treatments. The vast majority of current treatment options target managing symptoms related to the disease and assisting with maximizing a patient's function [4-6].

HD patients are frequently very sensitive to side effects of medications. Treatment is needed for patients who are depressed, irritable, paranoid, excessively anxious, or psychotic. Depression can be treated effectively with standard antidepressant drugs with the caveat that drugs with substantial anticholinergic profiles can exacerbate chorea. There is also a body of anecdotal evidence that the SSRI Sertraline can cause a range of undesirable side effects specifically in HD. Our studies of Sertraline in depression show a drop but not statistically significant lowering of IPA levels on 4 weeks of Sertraline therapy which is not seen in studies of IPA levels in subjects taking Citalopram or Escitalopram.

As HD progresses, psychiatric, physical and functional effects become more pronounced, leading to the need for increased care from family members and health care providers.

In 1993, the HD gene was first mapped and cloned [7]. The gene codes for a protein which contains 3144 amino acids and is called "huntingtin". In individuals with HD, a trinucleotide repeat sequence (CAGn) located near the 5' end of the gene is expanded beyond the normal repeat range [7] and this causes translation of an expanded polyglutamine sequence in the protein. Normal individuals usually have between 17 and 29 CAG repeats. Individuals with HD have more than 38 of these repeats. For individuals having more than the "normal" number of repeats, there is a relationship between the number of CAG repeats and the age of disease onset, with higher numbers of repeats leading to earlier onset of disease symptoms. The exact correlation is still being investigated.

Interestingly, in HD, only certain types of neurons are targeted by the disease. Certain populations of neurons degenerate while other less vulnerable populations are not affected [8]. The area most affected by neurodegeneration is the neostriatum, although research has shown that neuronal loss occurs in many other regions of the brain as well [8]. Both degenerative and proliferative changes [9, 10] in certain neurons suggest that mutated huntingtin is the cause of compensatory and degenerative genetic programs in a process that takes place over many years. The sequence of events starts with neuronal dysfunction and eventually leads to death.

Much is still unknown about the biochemical mechanisms of HD. A clear pathway from genetic mutation to neuronal dysfunction has not yet been fully established and understood. The function of huntingtin, a predominantly cytoplasmic protein, is unknown. It is commonly expressed and it has been found to be spread throughout neurons in the brain [11-15]. Most individuals who have the disease possess both normal and mutant alleles, which, in aggregate, create functional changes in which the mutant huntingtin exhibits toxic effects.

It has been suggested that the proteolysis of mutant huntingtin and release of the toxic N-terminal fragment may play a direct role in causing the disease [16-18]. In human, animal and cellular models, the presence of the N-terminal fragment has been shown to lead to protein aggregation in the nucleus and cytoplasm [19-21]. It has also been shown to interfere with the normal processes of neurons. In the normal pathway for elimination of protein aggregates, ubiquitination assists in the removal of these unwanted structures. However, in the case of the N-terminal fragments mentioned above, although ubiquitination occurs, the proteins still remain. It has been proposed that this phenomenon may result from misfolding of the protein and failed mechanisms of protein degradation [22, 23]. Other studies of HD aggregates suggest the ability of variant huntingtin to sequester certain proteasomal proteins [24], chaperones [25], normal huntingtin [26], and transcription factors [27-33]. Huntingtin aggregates have been observed in brain tissue from both patients who died as a result of having HD and those who were at-risk but died before exhibiting symptoms of HD [21, 34-36].

There is still much discussion surrounding the exact mechanism for the damage caused by huntingtin aggregates [37]. Most research suggests that the toxicity is created by mutant huntingtin or its fragments and their interactions with other proteins and transcription factors. Mutant huntingtin may also trigger deleterious biochemical cascades which alter the environment such that the relevant proteins become increasingly susceptible to alteration by oxidative damage, apoptotic signals, energy depletion, and excitotoxic stress. All of these could potentially lead to disordered physiology which results in the death of neurons [38].

Recently, greater understanding of these causes of these biochemical processes has allowed for the proposal of certain therapeutic interventions. Some of these have been studied through the use of HD transgenic mouse models.

There are numerous challenges inherent in the development of creating therapies for HD. In general, there are two goals. The first is to be able to treat patients with HD by delaying or preventing disease onset in those who are at-risk genetically. The second goal is to develop therapies to slow the progression of the disease in those already afflicted. Creating both types of therapies is challenging and time-consuming. In general, potential therapies are first tested and filtered through genetic mouse models of HD when preclinical data suggests that a compound may act in a neuroprotective role. If the compound successfully shows efficacy in mouse models, it is evaluated in phase I drug trials. Unfortunately, the majority of compounds evaluated down this pipeline are preexisting.

Another method being utilized is the "shotgun" method where dozens of compounds are tested at once to see if they are able to ameliorate the neurodegeneration in HD. Although somewhat crude, this approach has helped to increase the number of starting compounds being tested against HD.

As one can imagine, the above process can be complex and time-consuming. Genetic animal models are costly, slow and not entirely genetically accurate representations of the "human" condition of HD, as the most commonly used R6/2 mice typically live only 100 days. Longer lived HD mouse models such as the CAG140 significantly extend the time and cost of initial animal model trials. Ideally, it would be most useful to discover biomarkers of therapeutic response from genetically modified animal models, that affect pathways, mechanisms and compounds that are congruent in both the mouse and human, as they would help researchers to determine the effects of a particular therapy on the animals, and thus would provide mechanistic information about potential drug effects in humans and an indication as to whether the drug may delay the onset of neurodegeneration in the human as well as in the mouse model.

Additional challenges to the process arise in phase I and II trials. Although discovering tolerable dose ranges for compounds being tested in HD patients is usually a straightforward process, it may be difficult to find quantitative "signals" which indicate whether the compound is effective. A method which allows the measure of these "signals" would therefore be of great importance, because it would justify the continuation of these studies in phase III trials. Without quantitative signals/biomarkers such as these, it is difficult to justify the continued study of a particular compound as the symptoms of HD are quite variable and their alteration does not necessarily correlate to amelioration of the disease itself. An example of this phenomenon is seen in the drug Haldol, which may help to lessen a patients' chorea, but may have other deleterious side effects [39]. In this example, improving the symptoms of the disease does not actually slow the disease process, which ultimately would be the most positive outcome of a particular drug study.

Lastly, the final challenge arises in phase III clinical trials. The conclusions from current studies in patients exhibiting symptoms of the disease are based on changes in the TFC (total functional capacity) scores which require measuring hundreds of subjects over at least 5 years to observe small changes (20% slowing) of decline. In order to determine whether a treatment actually delays the onset of symptoms clinically, in patients with the mutation who are presymptomatic, it may take thousands of subjects and dozens of years of follow-up to detect slight changes in the occurrence of symptom onset. As one can imagine, each of these trials requires time, financing and great effort on the part of the clinical investigator. Thus, very few interventions can be (and are) tested. Hence, there would be a great advantage to being able to discover both biomarkers of disease progression and biomarkers which allow for the determination of whether the disease is being slowed in a faster, simpler and less expensive manner.

In one aspect, the present disclosure provides a method for identifying one or more markers for Huntington Disease or other neurodegenerative diseases, or hypertension, stroke or ischemic heart disease. In another aspect, the present disclosure provides a method for monitoring progression of Huntington Disease or other neurodegenerative diseases, or hypertension, stroke or ischemic heart disease and/or effectiveness of therapies for Huntington Disease or other neurodegenerative diseases, or hypertension, stroke or ischemic heart disease. In still yet another aspect, the present disclosure provides a method for therapeutic monitoring and for treating Huntington Disease or other neurodegenerative diseases, or hypertension, stroke or ischemic heart disease, and to therapeutic agents useful for treating Huntington Disease or other neurodegenerative diseases, or hypertension, stroke or ischemic heart disease.

In another aspect, the present disclosure provides a pharmaceutical composition for treating or preventing Huntington Disease or other neurodegenerative diseases, or hypertension, stroke or ischemic heart disease in an animal, including a human, or for delaying or ameliorating the effects of Huntington Disease or other neurodegenerative diseases, or hypertension, stroke or ischemic heart disease in an animal suffering from same, said composition comprising indole-3-propionic acid or a salt or ester or protein complex or inorganically bound preparation thereof and a pharmaceutically acceptable carrier therefor. In a preferred embodiment, the pharmaceutically acceptable carrier comprises a food or beverage with a specified quantity of IPA.

The present disclosure also provides a method for treating Huntington Disease or other neurodegenerative diseases, or hypertension, stroke or ischemic heart disease in an animal in need of said treatment, including a human, said method comprising administering to said animal a therapeutically effective amount of indole-3-propionic acid or a salt or ester or protein complex or inorganically bound preparation thereof. The indole-3-propionic acid or a salt or ester or protein complex or inorganically bound preparation thereof is administered in a pharmaceutically acceptable carrier, preferably in a food or beverage.

The present disclosure also provides a method of treating an animal susceptible to Huntington Disease or other neurodegenerative diseases, or hypertension, stroke or ischemic heart disease, including a human, said method comprising administering to said animal a therapeutically effective amount of indole-3-propionic acid or a salt or ester thereof. The indole-3-propionic acid or a salt or ester or protein complex or inorganically bound preparation thereof is administered in a pharmaceutically acceptable carrier, preferably in a food or beverage.

The present disclosure also provides a method for monitoring an animal suffering from Huntington Disease or other neurodegenerative diseases, or hypertension, stroke or ischemic heart disease such as a human for progression of said disease, which comprises determining the level or changes in the level of indole-3-propionic acid in said animal. In a preferred embodiment, the level of indole-3-propionic acid is determined by examining the animal's blood or plasma, urine or fecal matter.

The present disclosure also provides a method for predicting whether an animal, including a human, is at risk of progression to symptoms of Huntington Disease or at risk for or predisposed to other neurodegenerative diseases, or hypertension, stroke or ischemic heart disease, comprising analyzing a biological sample from said individual for a level or changes in the level of indole-3-propionic acid. In a preferred embodiment the biological sample comprises blood or plasma, urine or fecal matter.

In yet another aspect, the present disclosure provides a method for predicting a response of an animal, including a human, suffering from Huntington Disease or other neurodegenerative diseases, or hypertension, stroke or ischemic heart disease to a therapeutic agent, comprising obtaining a biological sample from said individual, analyzing said sample for the presence of indole-3-propionic acid, and comparing said analysis to a known standard and a data base of normal levels and levels of subjects at risk of or at risk of progression of neurodegenerative diseases, or hypertension, stroke or ischemic heart disease. In a preferred embodiment the biological sample comprises blood or plasma urine or fecal matter. The biological sample may be analyzed using LC-EC and MS, are employed either in parallel or off-line.

In yet another aspect the present disclosure provides a method for diagnosing Huntington Disease or other neurodegenerative diseases, or hypertension, stroke or ischemic heart disease in an animal suspected of suffering from Huntington Disease or other neurodegenerative diseases, or hypertension, stroke or ischemic heart disease, including a human, comprising obtaining a biological sample from said individual, and analyzing said biological sample for a level of indole-3-propionic acid. In a preferred embodiment, the biological sample comprises blood or plasma, urine or fecal matter, and the analysis is performed using LC-EC and MS, are employed either in parallel, or off-line.

The present disclosure also provides a method for predicting development of Huntington Disease or other neurodegenerative diseases, or hypertension, stroke or ischemic heart disease in an animal, including a human, comprising obtaining a biological sample from said individual, and analyzing said biological sample for a level of indole-3-propionic acid. In a preferred embodiment, the biological sample comprises blood or plasma, urine or fecal matter, and analysis is performed using LC-EC and MS and LCEC/MS, employed either in parallel or off-line.

The present disclosure also provides a method for modification of the gut microflora to increase the level of indigenous indole-3-propionic acid to protect individuals from developing symptoms of Huntington Disease or developing other neurodegenerative diseases, or hypertension, stroke or ischemic heart disease.

The present disclosure also provides a method for protecting an animal from effects of or progression of effects from neurodegenerative disease, hypertension, or ischemic heart disease, or for protection against secondary long term effects of stroke or head injury, comprising modifying the gut microflora or microbiome of the animal to increase a level of indigenous indole-3-propionic acid in the gut.

The present disclosure also provides indole-3-propionic acid as a biomarker or as a therapeutic agent for Huntington Disease or other neurodegenerative diseases, or hypertension, or ischemic heart disease and as a risk factor in the normal population for development of other neurodegenerative diseases, or hypertension, or ischemic heart disease, or for control of secondary long term effects of stroke or head injury, or a prophylactic for reducing effects of head injury in subjects at high risk of head injury.

The present disclosure also provides a method for monitoring changes in a healthy state of an individual comprising monitoring changes in the gut microbiome from the foot print of the gut microbiome in the feces of an individual. In one embodiment, the method comprises the steps of acquiring a sample of fecal material on toilet paper and immersing the sample in a stabilizing solution; subjecting the sample to survey LCE, MS and LCEC/MS parallel techniques to create a sample profile, and taking ratios of all compounds in the profile and comparing the ratios to said individual's prior sample or a data base of samples using statistical modeling to determine a category of the individual and changes in the aggregate composition of the gut microbiome as a result of intervention.

The present disclosure also provides a home sampling kit for measurement of Indole-3-propionic acid in normal individuals comprising a collection device for preserving Indole-3-propionic acid for testing in urine, blood sample or fecal sample, and a home sampling kit for measurement of Indole-3-propionic acid in normal individuals, to evaluate effects of dietary modification or to evaluate effectiveness of diet supplementation, comprising a collection device for preserving Indole-3-propionic acid for testing in urine, blood sample or fecal sample.

The present disclosure also provides a method for increasing levels of Indole-3-propionic acid in normal individuals which comprises supplementing the individual's diet with Indole-3-propionic acid or a salt in ester or protein complex or marginally bound preparation thereof, in a suitable carrier.

In yet another aspect, the present disclosure provides a method for treating stroke victims against protein damage and post event free radical damage to brain cells, comprising delivering Indole-3-propionic acids to said stroke victim through injection.

The present disclosure also provides a method of producing purified Indole-3-propionic acids in a protein bound matrix through use of organisms such as brewers yeast operating on purified tryptophan as a substrate.

The present disclosure also provides a method of assessing the disease risk of an individual comprising monitoring changes in the gut microbiome from a foot print of the gut microbiome in the feces of said individual, and assigning that individual to the lower quartiles of the distribution of normal values carrying the highest degree of risk.

Finally, the present disclosure provides a method for modifying the risk of an individual developing neurodegenerative disease, hypertension, stroke or ischemic heart diseases or for ameliorating the effects of head injury, which comprises administering to said individual a composition comprising indole-3-propionic acid or a salt or ester or protein complex or inorganic preparation thereof and a pharmaceutically acceptable carrier therefor.

In my earlier U.S. Pat. Nos. 6,194,217 and 6,210,970, the contents of which are incorporated herein, by reference, I disclose methods and systems for diagnosing, monitoring and categorizing disorders from biochemical profiles, in particular, the metabolome, using liquid chromatography and electrochemical detection (LC-EC) for profiling electroactive molecules in bodily fluids such as plasma, urine and cerebral spinal fluid (CSF), nasal swabs, sweat or other body fluid, for diagnosing disorders in test individuals by categorizing or differentiating individuals based on comparisons of biochemical analytical data of small molecule inventory against data bases of known or previously diagnosed cases. While LC-EC studies permit one to differentiate biochemical differences between patients suffering from HD or other neurodegenerative diseases, or hypertension, stroke or ischemic heart disease and controls, LC-EC studies do not permit one to reproducibly identify specific markers or potential therapies for patients suffering from HD or neurodegenerative diseases, or hypertension, stroke or ischemic heart disease.

In accordance with the present disclosure, we employed a combination of separation and analytical techniques to separate and identify small molecule profiles of individual and pooled sample materials to identify specific markers, for HD or other neurodegenerative diseases, or hypertension, stroke or ischemic heart disease, and we demonstrated therapeutic agents for treating individuals suffering from HD or other neurodegenerative diseases, or hypertension, stroke or ischemic heart disease. More particularly, we employed a combination of LC-EC and LC-MS arrays in parallel and off-line, to separate and identify the compounds of the small molecule profiles of individually and pooled samples, to identify specific markers for HD or other neurodegenerative diseases, or hypertension, stroke or ischemic heart disease, and to monitor and demonstrate the results of therapeutic intervention. It should be noted, however, that other separation and analytical technologies also advantageously could be used, including, by way of non-limiting example, HPLC, TLC, electrochemical analysis, mass spectroscopy, refractive index spectroscopy (RI), Ultra-Violet spectroscopy (UV), fluorescent analysis, radiochemical analysis, Near-InfraRed spectroscopy (Near-IR), Nuclear Magnetic Resonance spectroscopy (NMR), Light Scattering analysis (LS) and other methods known in the art. Using the above described separation and analytical techniques, we discovered that the gut microbiome product indole propionic acid (IPA) is dramatically reduced in patients suffering from HD or other neurodegenerative diseases, or hypertension, stroke or ischemic heart disease, and that treating patients suffering from HD or other neurodegenerative diseases, or hypertension, stroke or ischemic heart disease with IPA and/or modifying the nature of the gut microbiome of an individual suffering from HD or other neurodegenerative diseases, or hypertension, stroke or ischemic heart disease, i.e. to increase the level of indigenous indole-3-propionic acid, may significantly delay the time before symptoms of the disease occur, as well as the life span, functionality and quality of life of individuals suffering from HD or other neurodegenerative diseases, or hypertension, stroke or ischemic heart disease. Increasing levels of IPA in the lower two quartiles of IPA levels of normal subjects will also potentially reduce the risk of these individuals for neurodegenerative diseases, or hypertension, stroke or ischemic heart disease. Increasing IPA in prenatal mothers may also prevent the transmission of HD or tendency to risk of other neurodegenerative diseases, or hypertension, stroke or ischemic heart disease to an individual's offspring.

BRIEF DESCRIPTIONS OF THE DRAWINGS

Further features and advantages of the present disclosure are seen from the following detailed description, taken in conjunction with the accompanying drawings, wherein:

FIGS. 1A and 1B show a side-by-side comparison of two off-line LC-EC array chromatograms showing a single control patient plasma sample post ACN precipitation (enclosed) and a single plasma sample from a diagnosed HD patient post ACN precipitation;

FIGS. 2A and 2B show a side-by-side comparison of the same two off-line LC-EC array chromatograms enlarged in the region 21-32 min;

FIG. 3 is a digital map of data exported from the off-line LC-EC array;

FIG. 9 is an example of one peak of particular interest in HD plasmas, 9A shows the response of the isolated peak in the parallel LC-EC and 9B the corresponding TIC response in the parallel MS;

Figure 18:
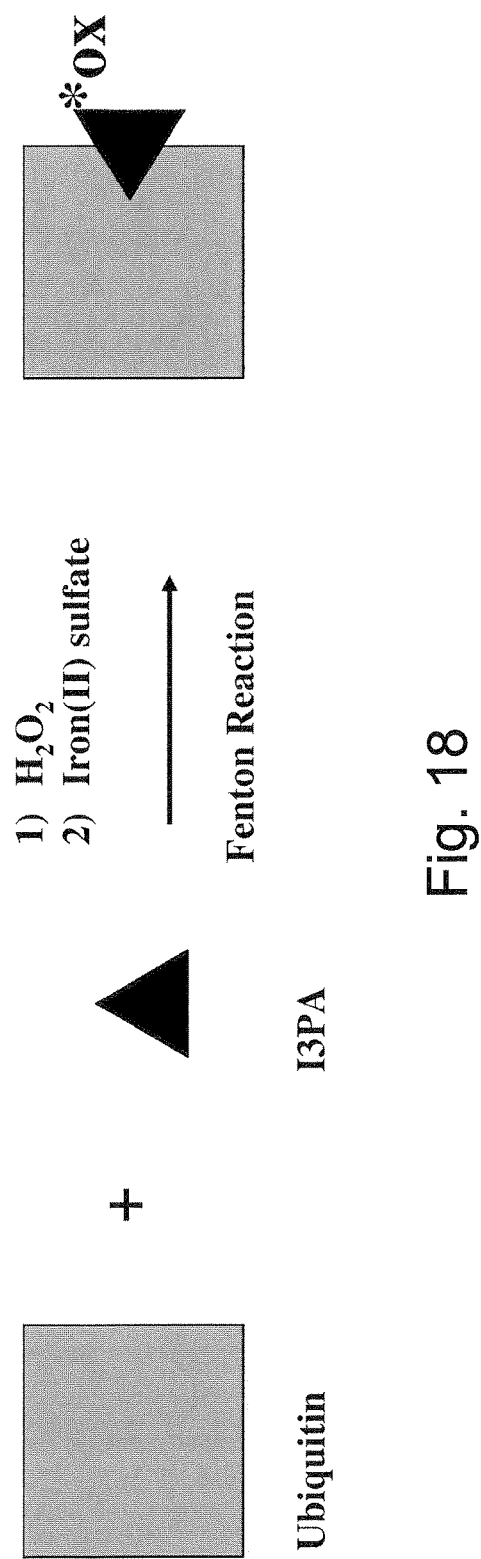
Figure 19:
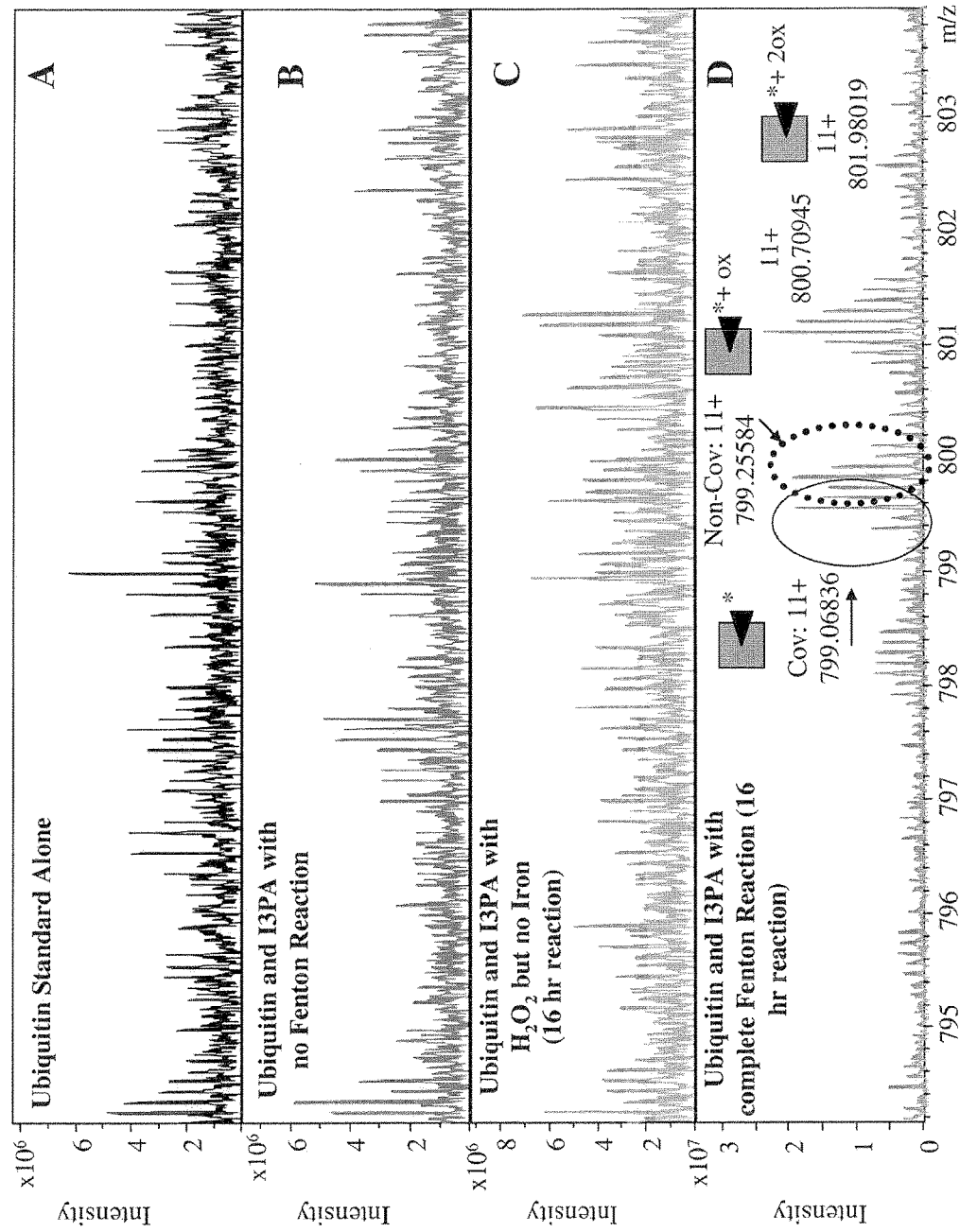
Figures 20, 21:
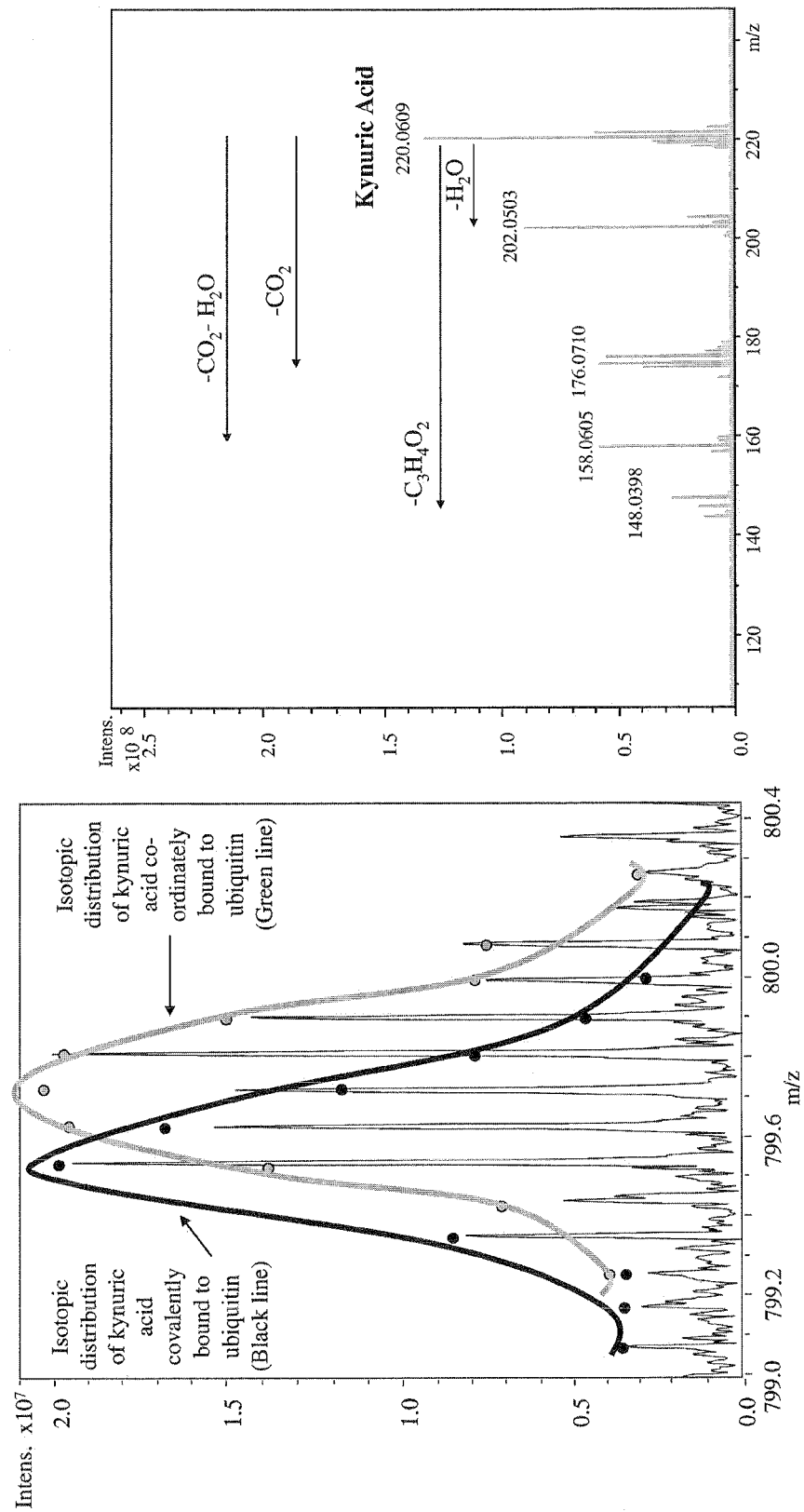
Figure 22:
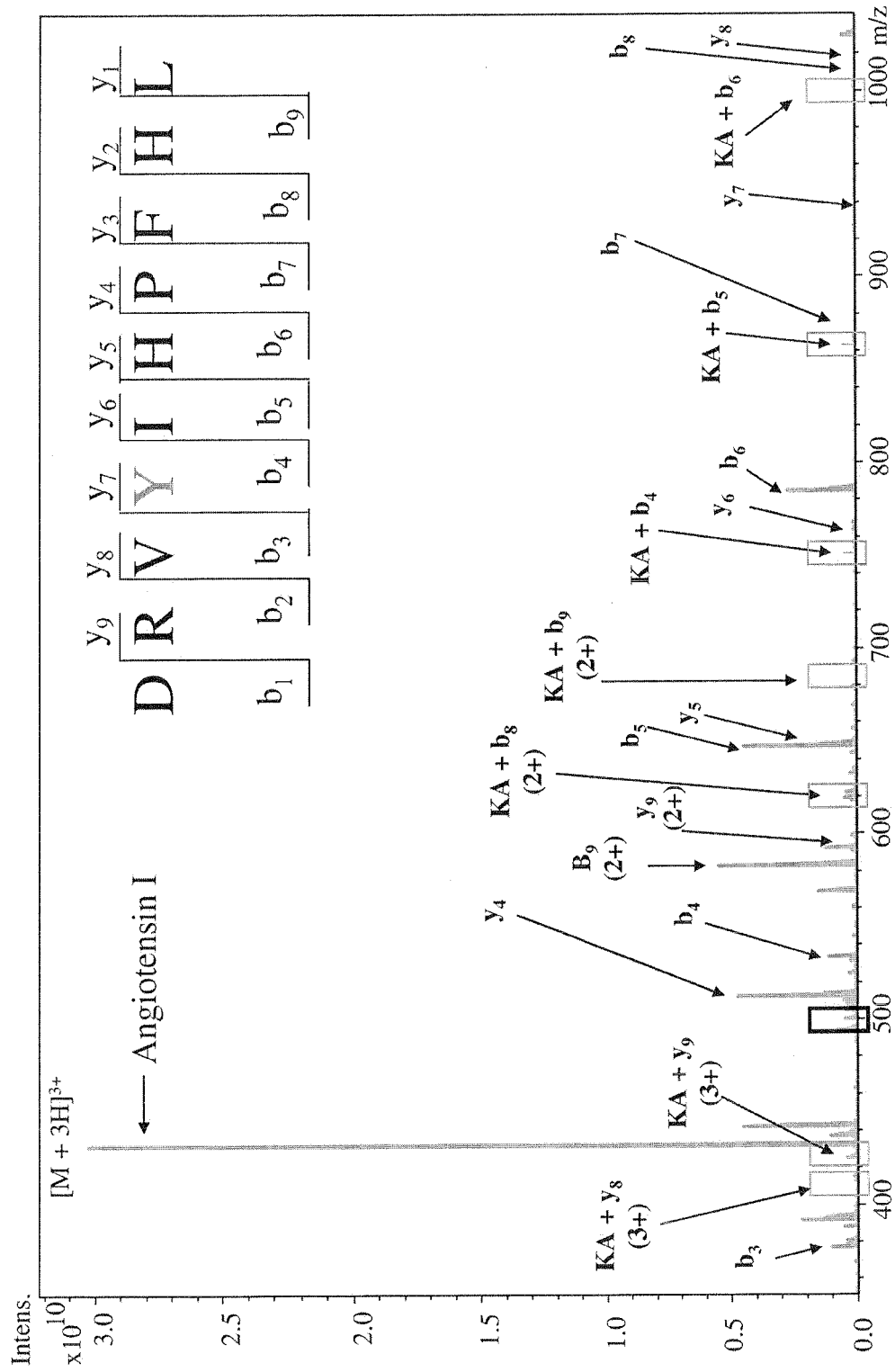
Figure 23:
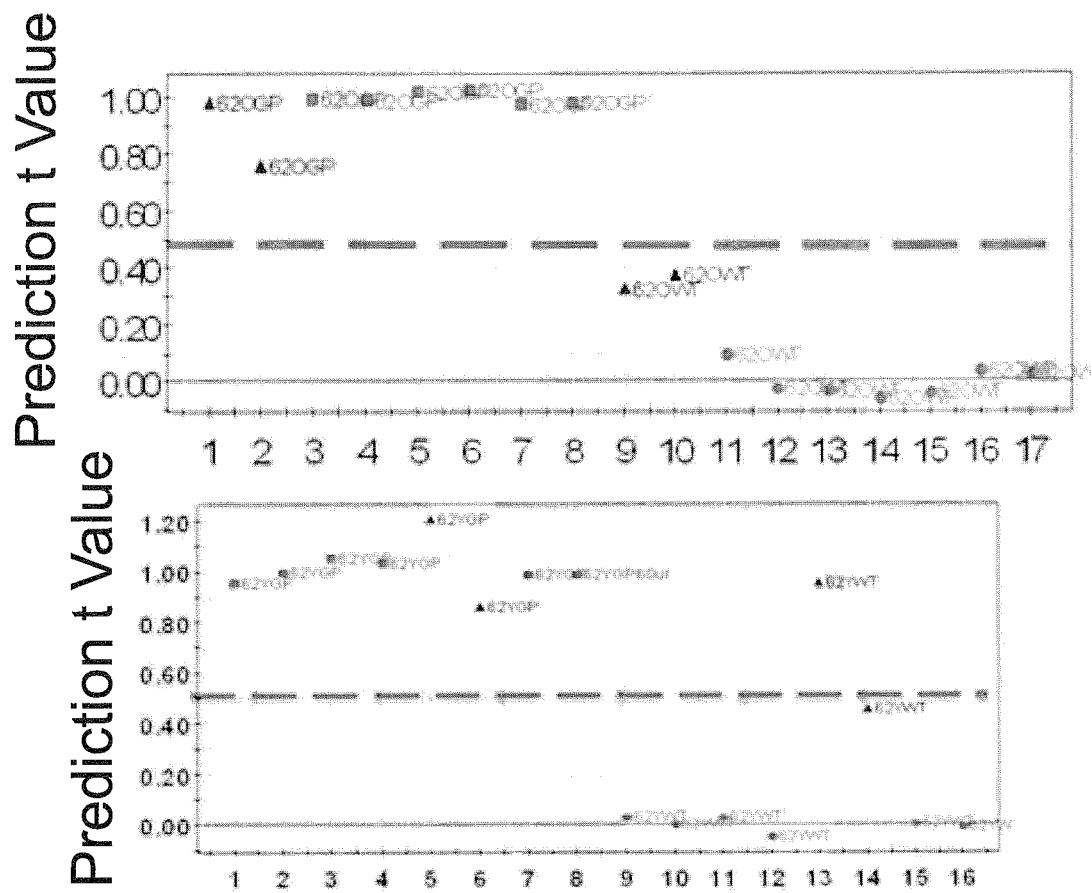

FIG. 18 schematically illustrates I3PA combining with ubiquintin as a result of a "Fenton" reaction;

FIG. 19 are four mass spectra of ubiquintin and I3PA;

FIG. 20 are plots showing isotopic distribution of kynuric acid covalently and co-ordinately bound to ubiquintin;

FIG. 21 is an MS/MS spectrum of kynuric acid;

FIG. 22 shows the MS/MS spectrum of product assigned as kynuric acid;

FIG. 23 shows the categorical separation of the CAG140 HD mouse model from its wild type littermates based on the foot print ot the gut microbiome in feces at 19 days post weaning (left hand panel) and at 3 months (right hand panel). The figures as shown are for one of 5 tests of the models using 2/3 training sets and 1/3 validation sets. The correlct classification rate for these models was 90% and 83% respectively. This indicates that the genomic variant imposes a unique variationin the aggregate composition of the gut microbiome at a very young age that persists through maturation. IPA was a major variable of importance contributing to the separation.

Figure 24:
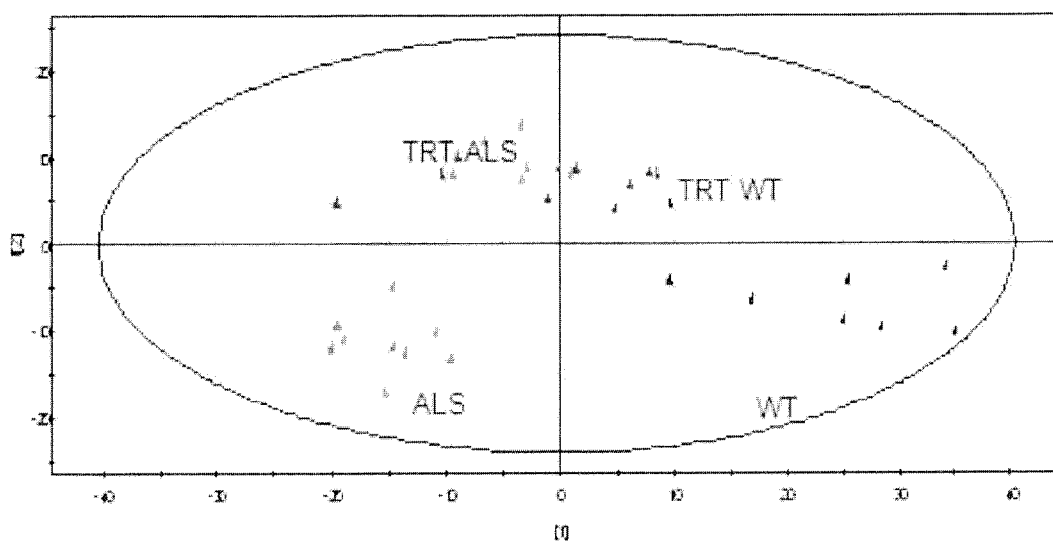

FIG. 24 This PLS-DA model shows a similar separation in the G93A ALS model mice from their wild type littermates based on the footprint of the gut microbiome and the effect of creatine administration both wild type and G93A mice on changing the gut microbiome to a different state. This shows that although the gut microbiome is genetically determined it can be modified by therapeutic intervention. Again in this case I3PA was a variable of importance in the separation of the gene modified and wild type mice. However, it was not significantly changed by creatine in this study.

Figure 25A:
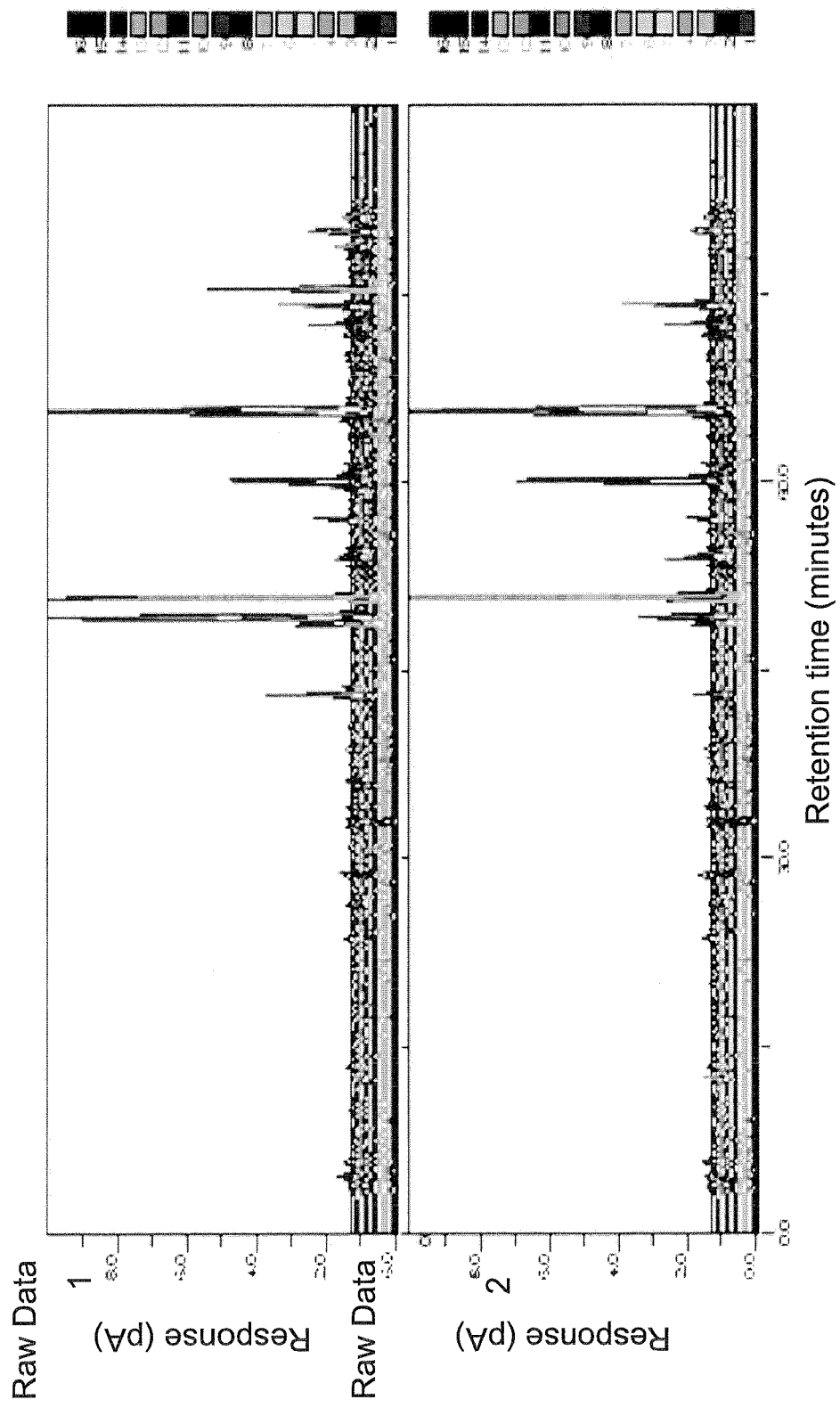
Figure 25B:
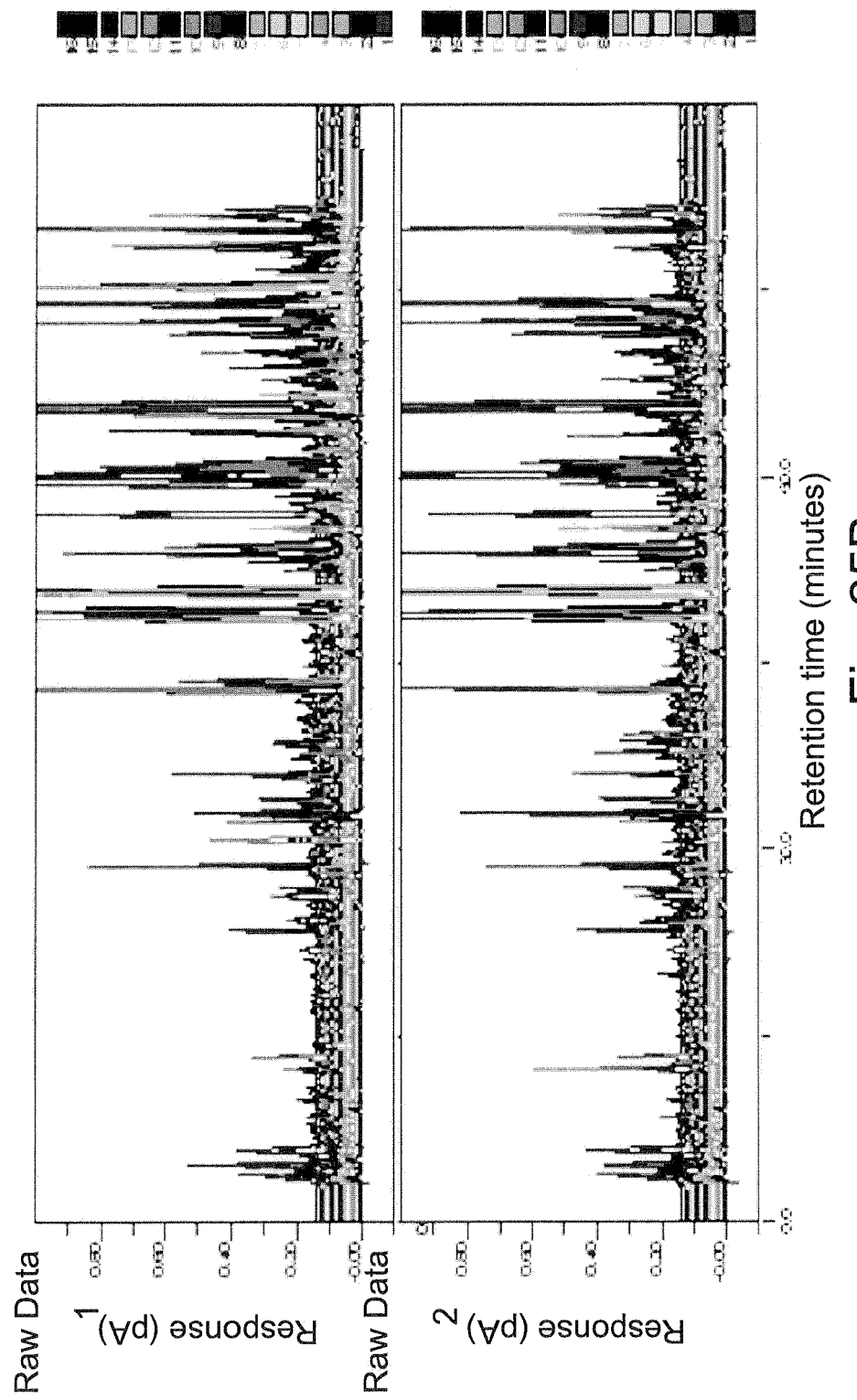
Figure 25C:
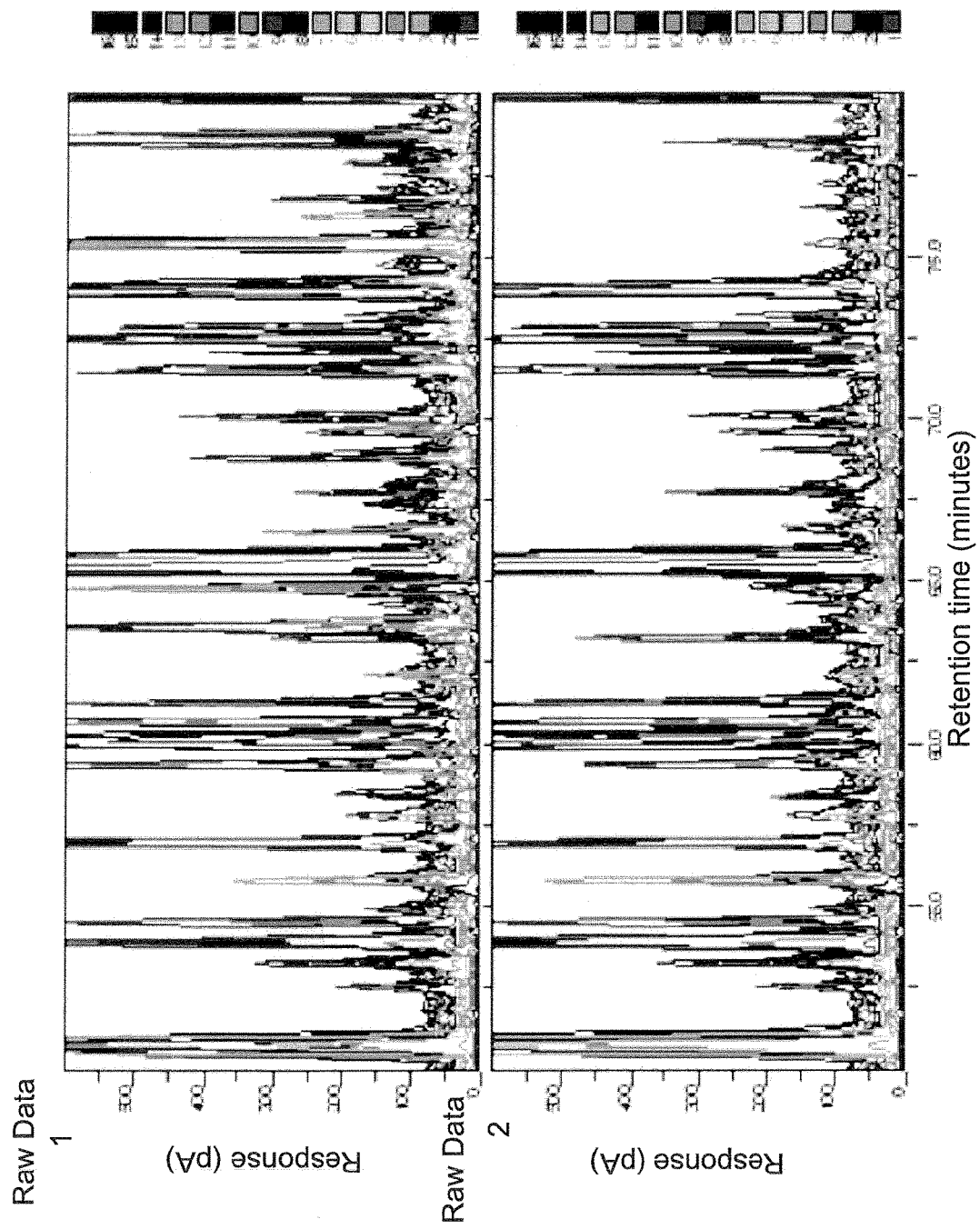

FIGS. 25 A, B and C. these show LCEC chromatograms of fecal sample acquired on toilet paper into 70% isopropanol and subsequently processed and analyzed. (panel 1 is husband, panel2 is wife). Notable visual differences are amplified in FIG. 25C in the region of 75-80 min.

Figure 26:
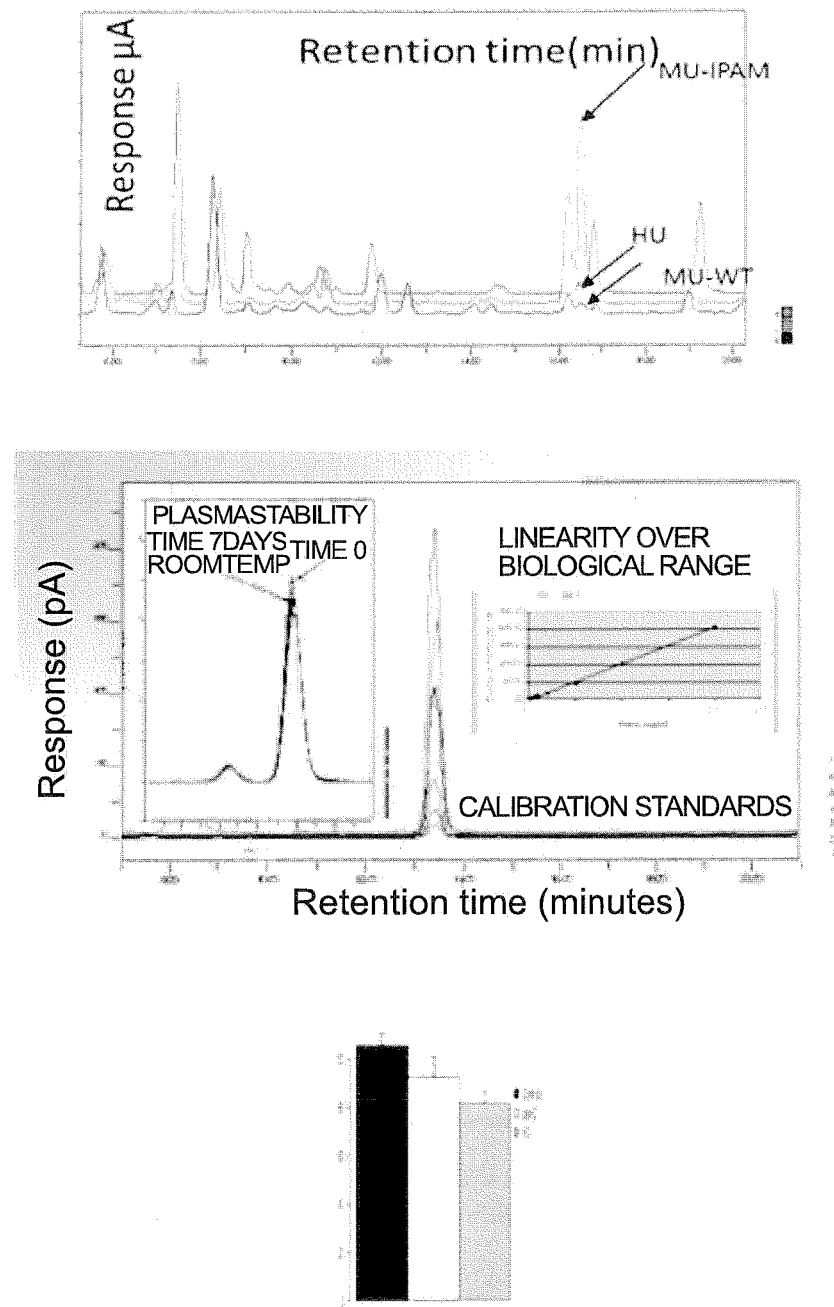

FIG. 26 shows the basic charicteristics of the targeted method for I3PA. the left hand panel shows the progressive decrease in plasma I3PA from control to Presymptomatic HD to HD subjects using the long gradient LC-EC protocol, which was the initial rationale for developing a targeted method, The middle panel shows the stability of plasma I3PA over a one week period with a plasma sample at room temperature which is critical for methods aimed at population based screening and the response of IPA and linearity of the method in a rapid 8 min. method. Panel three shows the application of a variant of the targeted method for urine samples which allowed the definition of two metabolites of IPA and subsequently the ability to monitor IPA levels from urine in both mouse trials and in human subjects.

Figure 27:
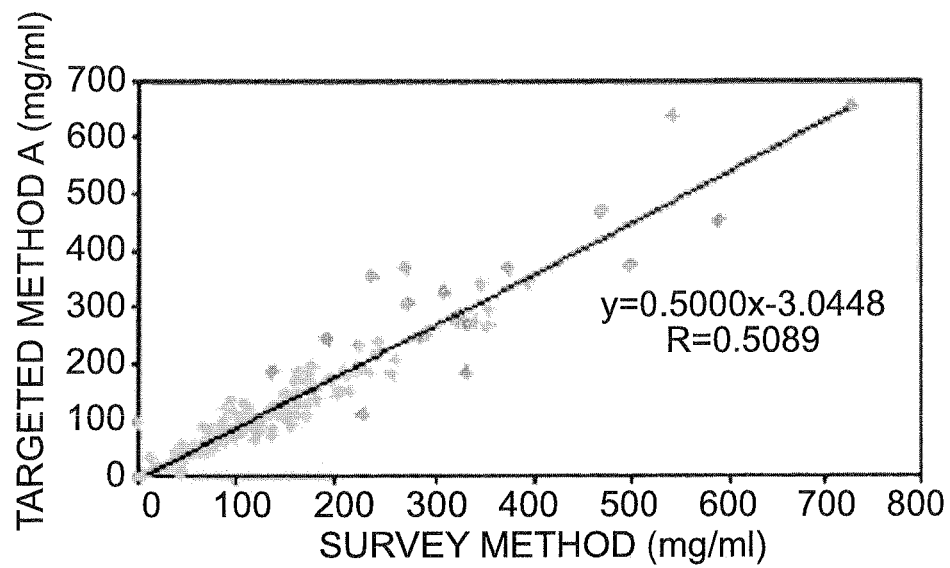

FIG. 27 shows the linearity of the targeted method with long gradient method chromatograms where I3PA was determined by coulometric integration of the dominant, leading and following sensor responses of coulometric sensors. This allowed the quantitative assay of I3PA in archived historical studies which had been performed prior to the structural identification of I3PA and in historical archives of sample sets.

Figure 28:
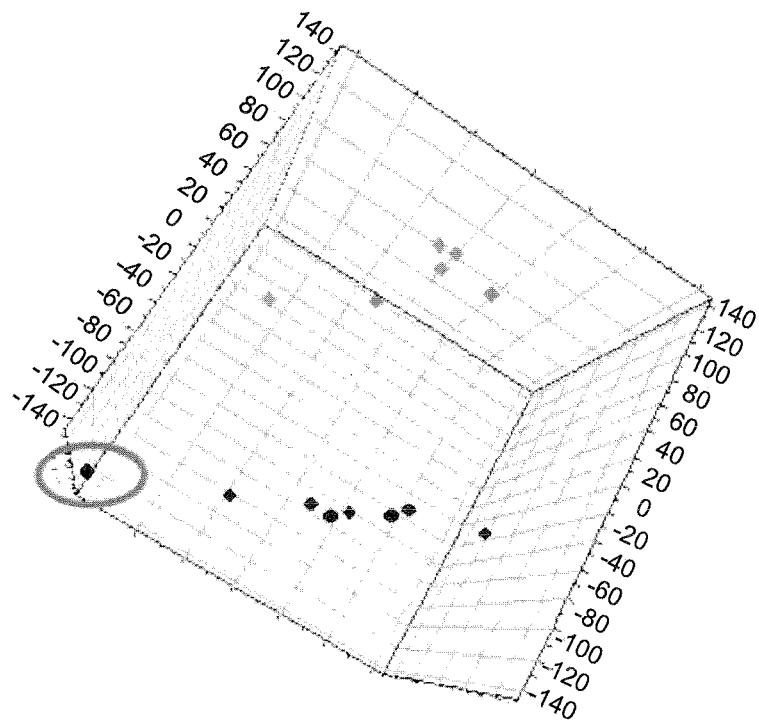

FIG. 28 this shows the PLS-DA separation of husband and wife using 8 and 6 fecal samples taken ove a 10-15 day period, processed for LC-EC profiles as shown in FIG. 25 and analyzed as ratios of all resolved peaks. The circled outlier is a sample drawn after five days of antibiotic therapy post dental surgery. This indicates again the individual specific character of the gut microbiome reflected in the foot print of the gut microbiome in feces, ad provide a means of monitoring the composition and changes in the gut microbiome.

Figure 29:
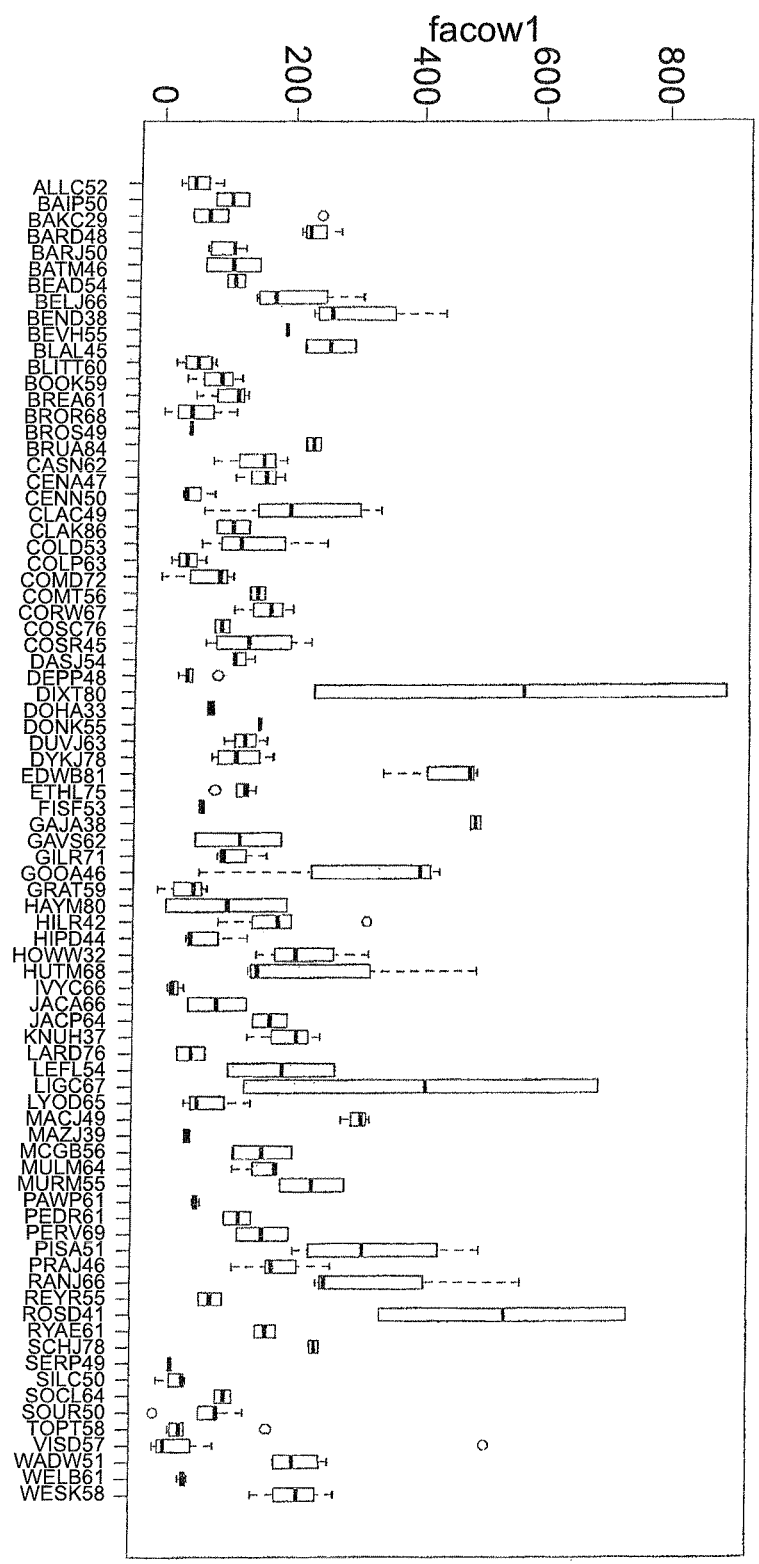

FIG. 29 shows an example of an ABNOVA box plot of serial plasma I3PA levels of subjects sampled over time periods of 3 months to 6 years, demonstrating that I3PA levels are an individual specific characteristic and again supporting that I3PA levels are to a large extent genetically determined and consequently low levels as seen in neurodegenerative and cardiovascular disease are a risk factor for these diseases.

FIG. 30 shows a summary of results from a loading study of the I3PA derivative indole propionamide (IPAM). This study led to the realization that the correlation between brain plasma and urine allows the tracking of animals in a therapy testing trial can be conducted without sacrificing the animals and that population based measurements can be accomplished with micro samples of either urine or plasma. As with other studies it also shows lower levels of IPA in the gene modified vs the wild type littermate mice. The data also indicates that IPAM is converted rapidly to I3PA in plasma and less rapidly in the gut suggesting that I3PA delivered to the gut through an appropriate vehicle is a better modality for therapy of supplementation than IPAM.

DETAILED DESCRIPTION

Initial Studies:

In order to identify potential candidates of interest, we first analyzed profiles from 200 plasma samples of HD subjects in a drug trial of creatine and 35 control subjects using a LC-EC array following the teachings of my U.S. Pat. No. 6,210,970. For the stated initial purposes of the study, the data was exported for compounds in tyrosine, tryptophan and purine pathways that were hypothesized to be affected. We also exported the data in digitized form capturing all of the information in the profiles. Analysis of this data between HD subjects and controls revealed a region 50% lower in the HD subjects of high significance P=10-8 in channels 11, and 12 and 78.2 min. From the electrochemical characteristics, we suspected that this region might reflect compounds containing an indole moiety.

We then ran in pooled samples spiked pools and standard mixtures of 20 indoles varying the chromatography to determine the mobility of the indole mix standard with the qualitatively unidentified peak. Under 5 different gradient conditions and with different ion pairing/non-ion pairing and pH mobile phases the unknown compound matched the retention time and electrochemical significance of indole propionic acid.

Thereafter we ran over 800 plasma samples from HD and control subjects and R6/2 and CAG140 HD mouse models and confirmed that the chromatographically identified indole-3-propionic acid (I3PA) was significantly lower 42% p=10-6 in both the HD humans and HD mouse. From these studies, and because of the congruence of the mouse model and human response we felt that I3PA would be a strong biomarker of HD state and a useful biomarker for translation of drug trials in mice to humans.

We then initiated source studies of mouse feces from HD and wild type mice which showed lower levels of I3PA in the HD mice confirming the source of the gut microflora-presumably *clostridium sporgenes*. We analyzed mouse chow and typical human foods and confirmed that levels of I3PA were too low to account for plasma or brain concentrations.

We analyzed brain samples from HD mouse models and human post mortem brain to confirm that the I3PA did cross the blood-brain-barrier and was lower in both HD mouse brain and human HD brain.

We also created pooled and spiked samples and carried out isolation and concentration procedures and chromatographic modifications to allow structural confirmation of the I3PA peak using parallel LC-EC/LC-MS.

Enabled by the development of targeted methods and the comparison of targeted methods to the survey method values extracted and analyzed by coulometric integration (FIG. 27), we have also performed studies of IPA levels in various other diseases, and with various pharmalogical interventions as set forth below, and recorded results as shown below.

To do this we returned to archived studies and samples of other conditions in studies with the same methodology dating back to 1992. These were initially undertaken to develop different markers and hypotheses. In these prior studies what we have now confirmed as I3PA had been identified only as a peak of significance for which we are now able [1-7] to obtain quantitative values. We also evaluated on-going studies to determine the specificity of I3PA as a marker for HD, the effect of drugs commonly used to treat symptoms of HD and IPA levels in other diseases. The summary below is from 17 different studies in which we used standard 2 tail t test statistics to determine the significance of levels of I3PA between categories and ABNOVA to determine the extent to which I3PA levels are an individual specific characteristic.

Alzheimer's Disease
Study 1. In CSF (from reevaluation of archived chromatograms from U.S. Pat. No. 6,210,970)
Control N=66 mean IPA 3.87 ng/ml
AD N=60 mean IPA 2.17 ng/ml
P=0.0014
From current work
Study 2. In CSF
Controls N=38 IPA mean 4.05 ng/ml
MCI N=39 IPA mean 3.41
AD N=40 IPA mean 2.95 ng/ml
P AD vs. Control=0.013
P MCI vs. control=0.052
Study 3. In Plasma
Controls n=30 mean 189.3 ng/ml
AD N=30 mean 154.3
P=0.046
ALS Amyotropic Lateral Sclerosis
Study 4. In Plasma (from re-assay of archived sub aliquots from (7))
Controls N=30 mean 192.3 ng/ml
ALS and Lower Motor Neuron Disease N=30 mean 167.8 ng/ml
P=0.032
Study 5. In CSF (from re-assay of archived sub aliquots from (7))
Control N=21 mean 3.25 ng/ml
ALS N=19 mean 2.24 ng/ml
P=0.054
Study 6 In Plasma (from reevaluation of archived chromatograms from (2))
Control N=27 mean 201.2
ALS N=23 mean 172.0
P=0.029
From current work
Study 7. In CSF
Control N=30 mean 4.13 ng/ml
ALS N=30 mean 2.89 ng/ml
P=0.018
Study 8. In Plasma
Control N=56 mean 201.4
ALS N=48 mean 172.7
P=0.0072
Parkinson's Disease
Study 9. In CSF (from reevaluation of archived chromatograms from DATATOP deprynyl study (1))
Controls N=47 mean 4.25 ng/ml
PD at baseline N=59 mean 3.01 ng/ml
P=0.035
Baseline vs. deprynyl treated subjects p=0.45
ABNOVA for serial samples p=6.3*10exp-7
Study 10. In Plasma (from reevaluation of archived chromatograms from (3,4))
Controls N=20 Mean 186.9
Un-medicated PD Mean 172.2
P=0.051
Study 11 In Plasma
Controls N=30 Mean 196.01
Un medicated PD Mean 167.90
P=0.032
Cardiovascular Disease
From current work
Ischemic heart subjects pre and post undergoing mental stress tests
Study 12. In plasma
N=20
Baseline mean 175.3

1 hour post mental stress test mean 161.3 ng/ml
Baseline vs. all controls all studies P=0.0016
Group baseline vs. post stress P=0.045
Group with change normalize to baseline P=0.0014
Stroke:
Study 40 subjects with hemorrhagic and or ischemic stroke. Samples of CSF, ipsilateral and contralateral jugular plasma. (From reevaluation of archived chromatograms of samples from the First Russian Medical University Stroke Center)
N=40
Study 13. In Plasma
Hemorrhagic stroke N=18 mean 102.1 ng/ml ipsilateral 112.09 ng/ml contra lateral ischemic stroke n=22 mean 88.7 ng/ml ipsilateral 83.1 ng/ml contra lateral p value all plasma vs. other controls p=10exp-6
Study 12. CSF
Hemorrhagic stroke N=18 mean 1.02 ng/ml
ischemic stroke n=22 mean 0.91 ng/ml
p value all CSF vs. other controls p=10exp-8
Anti-Depressants and Anti Hypertensives have Little Effect on IPA
Drug effects
Study: Depression study of Sertraline (from reevaluation of chromatograms in (5))
Study 15. In plasma
n=57 baseline I and 4 weeks
Baseline mean 192.4 ng/ml
4 weeks mean 186.3 ng/ml
Group p value pre and post p=−0.41
P value normalized to base line p=0.1
ABNOVA test of self-similarity 3 serial samples p=2.6*10 EXP-11
Depression study of Escitalopram/citalopram
From current work
Study 16. In Plasma
N=150 baseline 4 and 8 weeks
Baseline mean 205.15
8 weeks mean 210.09
Group pvalue baseline vs. 8 weeks p=0.87
Pvalue normalized to baseline p=0.67
ABNOVA test of self-similarity 3 serial samples p=9.1*10 EXP-14
Hypertension study of Atenolol
From current work
Study 17. In Plasma
N=40 baseline and 8 weeks
Baseline mean 169.7
8 week mean 160.5
Group p value baseline vs. 8 weeks p=−0.81
Baseline normalized p value p=−0.71
Group mean of hypertensive subjects vs. all study controls p=0.0007

We further confirmed that I3PA is a progressive disease marker in HD. Decreasing in pre symptomatic HD vs. Controls and decreasing further after pheno-conversion and development of symptoms. We confirmed that IPA is statistically significantly reduced in other neurodegenerative diseases although not to the extent in HD and that it is not affected by SSRI and antihypertensive medications used HD and other neurodegenerative disorder to control concurrent symptoms. It is also reduced in ischemic heart disease, stroke and hypertension although interestingly it is not affected by the common treatment for hypertension using atenolol.

Based on these studies, we observed:

(1) lower 13PA is a progressive biomarker of state in HD that is characteristic of HD. IPA levels are not affected by depression or by drugs commonly used to treat depression or hypertension side effects symptoms of the disease or co morbidities;

(2) I3PA is also lower in other neurodegenerative diseases but not to the same extent as in HD and lower in in ischemic heart disease and hypertension and stroke;

(3) I3PA is also a progressive biomarker of state in HD mouse models;

(4) I3PA crosses the blood-brain-barrier and may play a role as an antioxidant and in suppressing protein aggregation; and (5) the source of I3PA is the gut microflora with minimal direct dietary input.

These findings suggest the use of I3PA as a biomarker of state and progression in HD:

(A) as a biomarker of therapeutic intervention in a drug trials; and (B) as a biomarker to evaluate/increase the probability that a drug that works in mice will work in people.

(6) IPA is a compound whose levels are an individual specific characteristic shown in FIG. 29 further supporting the genetic determination of IPA levels and the indication that such levels constitute a modifiable genetic risk of development of certain neurological and cardiovascular disorders.

This suggests that the individual's genome affects/determines the aggregate genome of the individuals gut microbiome. This means for many diseases with a genetic component (hypertension, autism, ALS with SOD mutant gene, HD, Genetic linked PD, genetic linked AD) we should be treating the gut and monitoring the aggregate gut microflora either through metabolomic profiles in plasma or urine, through measures in feces or through new technologies using MS approaches for bacterial ID. I3PA is an initial discovery using these concepts and approaches that can serve both as a therapeutic agent and an agent to reduce the risk of disease in individuals with genetically caused low levels of I3PA caused by low production by the aggregate of the commensal gut microbiome.

Detailed Discussion

Following our initial studies, we then undertook detailed studies as follows:

Coupling separation and analytical technologies such as LC-EC array and MS technologies together in a parallel LC-EC array-MS system, provides a powerful tool for identifying metabolites in HD. In our investigations described in this chapter, we used both offline LC-EC array and offline MS, as well as parallel LC-EC array-MS, to conduct a preliminary investigation of HD versus control plasma samples in order to evaluate the differences in metabolic signatures between these two groups.

391 plasma samples from 150 subjects enrolled in an ongoing "HD Biomarkers Study" and 40 healthy control subjects were evaluated. The number of samples collected from any one patient varied depending on the time they were enrolled in the study. Thus, this number ranged from one sample to six, depending on the patient. Samples used for analysis were selected based on the TFC (total functional capacity) score associated with the patient at the time of sample collection. The TFC score is a scale employed by physicians to designate to what extent the individual is affected by the disease. The scale ranges from 1-13 with I being the most severely affected and 13 being the least severely affected.

To create an initial database of compounds that differed between HD and controls, all samples were analyzed using gradient LC optimized for EC array following the teachings of my aforesaid U.S. Pat. No. 6,210,970. Gradient LC-EC analyses were performed using ESA model 582 Pumps (ESA Biosciences Inc., Chelmsford, Mass.) and a 16-channel ESA model 5600 CoulArray detector. Channels 1-15 used series Coulometric electrodes set in equal increments of 56 mV from 0-840 mV. Channel 16 was set at 870 mV. Two 4.6 mm×250 mm series C18 5-μm columns (ESA Biosciences Inc., Chelmsford, Mass.) were used. The gradient employed was linear from 0% Phase A (0.1 M sodium pentane sulfonic acid with 5% acetic acid) to 100% Phase B (80/10/10 MeOH/isopropanol/acetonitrile with 0.06 M lithium acetate; 7% acetic acid). The linear gradient was employed to 84 minutes, then 100% B was run to 110 minutes. The flow rate was 1 ml/min.

Plasma samples were prepared by a standard method as follows. Plasma (125 μl) was precipitated with 500 μl of ACN/0.4% acetic acid, vortexed for 30 s, and centrifuged at 21,000×g for 25 min at 4° C. The supernatant (500 μl) was centrifugally evaporated and reconstituted to 100 μl in mobile phase A; a 50-μl aliquot was injected onto the system. During sample preparation, pools were created from equal volumes of sub aliquots of all samples. The assays were run in sequence as follows: a set of combined diagnostic standards (including 80 known compounds), a pool of all samples in the study, 8 individual samples from the study, the same diagnostic standards as above, and a global pool. This sequence was repeated until all samples had been run. Run orders of all individual samples in the study were randomized. These sequences minimized possible analytical artifacts during data processing. Pools were used to assess the precision of the entire data set. Additionally, the pools were used as references for time normalization (peak stretching).

All chromatograms in the study were background corrected to eliminate the baseline drift inherent in gradient profiles. By controlling analytical conditions, the location of any particular peak in a 16-channel 110-minute chromatogram was held to within +/−5-30 seconds throughout the study. Background-corrected files were then sequentially time normalized against a single pool in the middle of the study sequence. A two-step stretching protocol with a multitude of peaks was first used. First, ESA CEAS 512 software was used to align 15-20 major peaks in the chromatogram and interpolate the positions between them. Then, an additional 20-25 smaller peaks present in most samples were selected from the derivative file and those were realigned, keeping the major peaks in the same position. Selected peaks were aligned within +/−0.5 seconds and non-selected peaks within +/−1 to 5 seconds over the entire 110-minute assay.

We exported the data in the form of a digital map. Using the complete digital output served two purposes: (1) to capture all analytical information for future data analysis; (2) to avoid possible artifacts introduced by peak-finding algorithms. The number of variables in the digital maps depended on the resolution set during the data export. In this work the resolution was set at 1.5 sec and the number of data points (variables, defined as the signal at a given time on a given channel) obtained from one sample, using our current LC-EC array approach, was 66,000. The number of variables in a digital map is not equivalent to the number of analytes, because an individual analyte is represented by more than one variable. Depending on the concentration of an analyte and on its separation across the EC array chromatogram, the number of variables characterizing an analyte could be between 10 and 100. In the consolidated files of a study, all variables were aligned in a spreadsheet for data analysis with each column representing a single sample organized by time from channel 1 to 16. Each row in a spreadsheet represents the response of a compound (variable) at a specific time and channel for all samples. This approach avoids artifacts in data reduction and protects against over fitting in the data analysis. Prior to data analysis, rows in the digital maps for which all values were negative or less than 30 pA (the noise level of an analytical method) for all samples were eliminated.

The data obtained from the digital maps were analyzed using partial least squares discriminant analysis (PLS-DA). PLS-DA can find individual components that best categorize or explain the variance in a data set. Within a given data set, PLS-DA models can be tested by developing the model on a subset of the cases and using the variables to test the remaining cases for specificity and selectivity. Thus, SIMCA-P software was used to create three PLS-DA models. Those models included: controls versus HD samples with TFC score 13; controls versus HD samples with TFC scores 2-6; and HD with TFC 13 versus HD with TFC 2-6. Also generated were lists of variables of importance (VIPs). These are the variables (peaks) which best define the separation between the various groups of data. Tables of VIPs in all PLS-DAs were generated. Each table gives the dominant EC channel and elution time of the particular VIP.

To verify whether the VIPs suggested by the PLS-DA software were real, visual inspection was done on groups of 16 samples from channel I to 16 using the CEAS software. Various groups were compared including control samples versus various groupings of HD samples by TFC score. VIPs which appeared to be most consistent and prominent were noted, as candidate for identification.

LC-MS analyses were performed using ESA model 582 Pumps (ESA Biosciences Inc., Chelmsford, Mass.) and an ESA model 5600 CoulArray detector, channels 1-12, 0-840 mV in 70 mV increments (ESA Biosciences Inc., Chelmsford, Mass.) coupled on-line to a QStar quadrupole orthogonal time-of-flight (Q-o-TOF) mass spectrometer (Sciex/Applied Biosystems, Foster City, Calif.) equipped with an ESI ion source. We sequentially used both positive and negative ion scan modes (m/z 100-2000, ionspray voltage 4.5-5.5 kV). Metabolite mixtures were separated on a 4.6 mm×250 mm (5-μm Shiseido C18) column at a flow rate of 0.8 ml/min. The HPLC eluent was split at a ratio of 9:1 with 90% being directed to the EC-array and 10% being delivered to the MS.

The un-fractionated HD and control plasma samples were diluted between 1:10 times in mobile phase A. The dilution was based on the relative amounts of the compounds of interest and the requirement to 1) perform multiple different runs with varying LC and MS parameters 2) to preserve material for subsequent $MS^n$ studies. Samples were assayed using a gradient method. The gradient employed was linear from 0% Phase A (0.2 M ammonium acetate, 5% MeOH) to 80% Phase B (0.2 M ammonium acetate, 80% MeOH). The linear gradient was employed to 100 min, then 100% B was run to 110 min. The flow rate was 0.8 ml/min.

An Information Dependent Acquisition (IDA) MS method was used to monitor the most intense ion signals in the range m/z 100-1000 and to fragment each of these components with the collision energy set to 50 eV and the quadrupole set to low resolution. Using this method, the retention times of compounds of interest were monitored as they passed through the mass spectrometer. Additionally, we compared these retention times to those of the peaks detected by the simultaneous EC-array analysis and to obtain initial values for parent masses of the compounds and to obtain the relevant MS/MS fragmentation.

The parallel LC-EC array-MS method performed on the Q-o-TOF mass spectrometer helped us to determine the masses of the metabolites of interest which had been selected for MS identification using the offline LC-EC array method. The purpose of obtaining this preliminary MS data was to allow us to focus on these particular masses when obtaining exact masses using a higher resolution mass spectrometer.

Initial qualitative analyses were performed by visual observation of the chromatograms obtained from the parallel LC-EC array-MS system. Chromatograms were overlaid using CoulArray software and compared on all 12 channels. First, chromatograms were compared by grouping samples of similar TFC scores and then by cross comparison across a range of TFC scores against control samples. Ten peaks were deemed "of interest" based on the following criteria: a) peaks were present only in HD samples; b) peaks were present only in control samples; c) peaks changed in intensity as TFC scores changed throughout the course of disease progression; d) peaks had of high enough intensity to suggest that the components would be identifiable by MS. After the peaks of possible interest were selected, IDA data was used to determine the masses of these peaks.

A small aliquot of each of the samples used for preliminary analysis on the parallel LC-EC array-MS system was saved for high resolution MS and MS/MS by infusion using a Qh-FT-ICR/12-T Solarix instrument (Bruker Corp., Bremen, Germany).

Because we observed the most prominent differences between control and HD in the samples with the lowest TFC scores, we decided to focus on determining the structures of peaks in this group of samples adapting protocols we had previously reported (8-10). We obtained three control samples and 7 HD samples whose TFC scores ranged from 2-6. These samples were prepared by extraction in acidified acetonitrile. Once the HD and control plasmas had been pooled, dried down and concentrated, the pools were each reconstituted in 200 µl of deionized water. The two pooled plasma samples were then fractionated using solid phase extraction (500 mg Diazem C-18 SPE, Diazem Corp. Midland, Mich.). Columns were equilibrated with 2 ml deionized water, 2 ml acetonitrile and 2 ml 1% acetic acid in deionized water. Each concentrated reconstituted supernatant from the two plasma preparations (200 µl) was loaded onto a freshly equilibrated SPE column. For each column, a single 300-µl collection was made to recover the void fraction and then 1 ml of each of the following eluants was collected: 10%, 20%, 30%, 40%, and 100% ACN. The fractions were centrifugally evaporated and reconstituted in 20 l of 50/50 methanol/water with 0.5% formic acid.

Analysis of IDA data from the parallel LC-EC array-MS system provided a list of the masses of 10 candidate biomarkers. This preliminary MS data then allowed us to focus on these particular masses while obtaining exact masses using the high resolution SolariX mass spectrometer.

High resolution MS and MS/MS data was obtained using a 12-T Qh/FT-ICR hybrid mass spectrometer (SolariX, Bruker Daltonics) equipped with a nanospray source that was operated in the positive mode. Tandem mass spectrometry experiments were performed by using the CID activation mode. Samples from the 20%, 30% and 40% ACN fractions were diluted 1:10 in 50/50 methanol/water and analyzed. CID fragmentation was performed in the hexapole. Detection of ions in the SolariX was performed at a resolution of 100,000. The mass assignment accuracy was better than 5 ppm.

High resolution MS and MS/MS data was obtained by infusion using an LTQOrbitrap "Discovery" (Thermo-Fisher, San Jose, Calif.) equipped with a with NanoMate TriVersa robot (Advion, Ithaca, N.Y.). Diluted samples from the 30% and 100% ACN fractions were analyzed using nanoelectrospray in the positive ion mode. Due to the scarcity of sample, no fragmentation experiments were performed. However, it was possible to obtain exact mass values for some compounds of interest. The detection of intact molecular ions in the Orbitrap was obtained at a resolution of 30,000. The accuracy was better than 5 ppm.

Results

Potential biomarkers of HD were identified. Specifically of interest were compounds that a) were present only in HD samples; b) were present only in control samples; c) had changed in intensity as TFC scores declined throughout the course of disease progression; and d) were present in sufficient quantity as to be identifiable using MS.

All samples in the study were analyzed according to the protocols discussed above. All 391 plasma samples from 150 subjects enrolled in the "Biomarkers Study" and 40 healthy control subject plasmas were prepared by acidified ACN extraction. The samples were vortexed, spun and supernatant removed from the precipitated protein pellet. The protein pellet was frozen at −80° C. and the supernatant was centrifugally evaporated to dryness and reconstituted in buffers appropriate for offline LC-EC array experimentation. FIG. 1 shows a side-by-side comparison of two offline LC-EC array chromatograms showing a single control patient plasma sample post ACN precipitation (A) and a single plasma sample from a diagnosed HD patient, a single patient post ACN precipitation (B) not on drug therapy. Peaks that are either unique or significantly different in size are labeled with red arrows. The figure was generated directly from the data, using the CoulArray software. Distinct differences between the two are labeled with arrows.

FIG. 2 shows a side-by-side comparison of the same two offline LC-EC array chromatograms as FIG. 1, however, it is enlarged in the region 21-32 min so that differences between the two chromatograms can be seen more clearly. Peaks that are either unique or significantly different in size are labeled with red arrows. The figure was generated directly from the data, using CoulArray software. We then set about to determine the structures of the compounds which differed between the disease and control plasma samples.

All data obtained using the offline LC-EC array was exported as a "digital map" for analysis. Shown in FIG. 3 is an example of a digital map showing variables 45,151-45, 171. The digital maps were imported into Microsoft Excel, and analyzed using statistical programs as discussed below.

Figure 4:
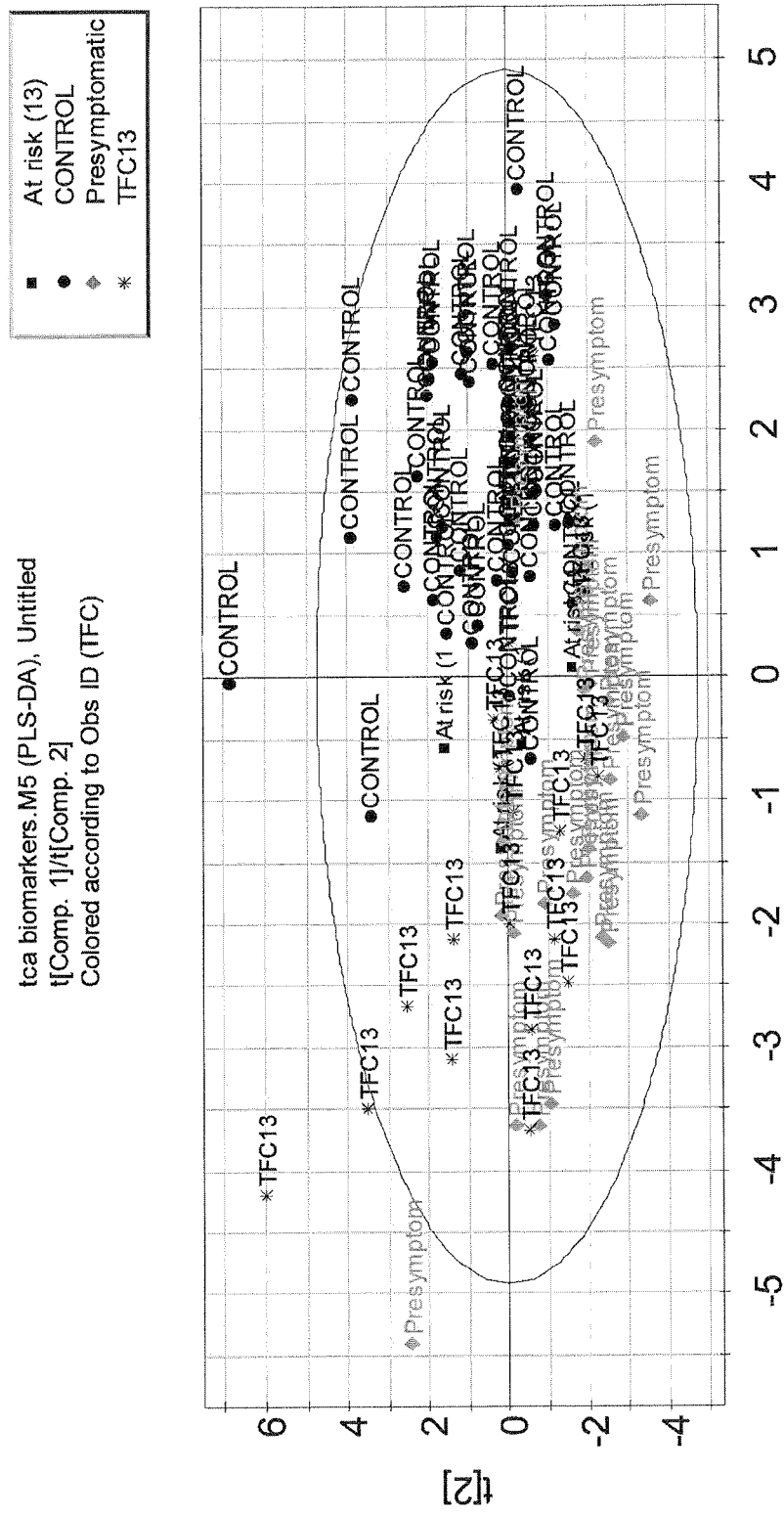
FIG. 4 is a partial least squares determinant analysis showing separation and grouping of the pre-symptomatic HD at-risk HD, HD samples with TFC score 13 and non-HD controls.
Figure 5:
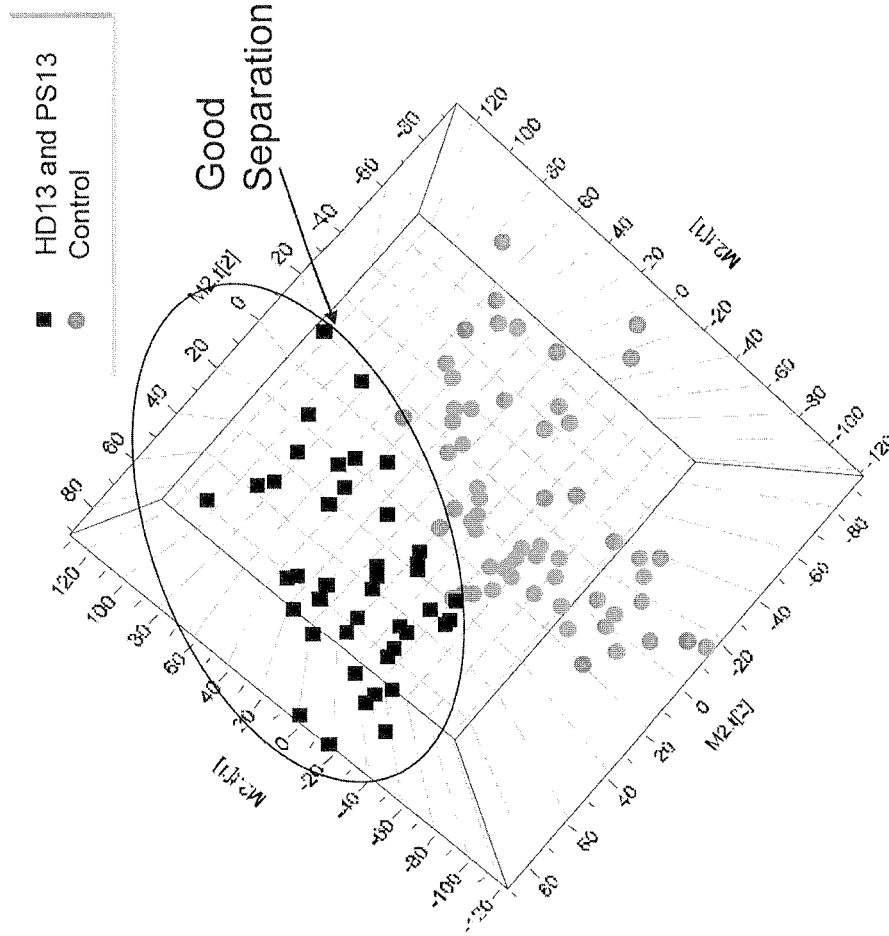
FIG. 5 is a partial least squares determinant analysis comparing control samples to HD patients with a TFC score of 13.

Using SIMCA-P software we created partial least squares determinant analysis (PLS-DA) figures showing the separation of various groups. FIG. 4 is a PLS-DA showing separation and grouping of the pre-symptomatic HD, at-risk HD, HD samples with TFC score 13 and non-HD controls. There is separation visible between the various groups indicating that specific variables may be involved with categorical separation. FIG. 5 is a PLS-DA comparing control samples (red) to HD patients with a TFC score of 13 (black). On the left side of the figure are the peaks (or determinants) which are most important in separating the two groups. 5 "VIP"s are listed on FIG. 5. After visual inspection of the results from approximately 60 samples, the most consistent VIP (that which was seen in at least 80% of the samples examined) is that which appeared on channel 9 and eluted at 88.75 min.

Figure 6:
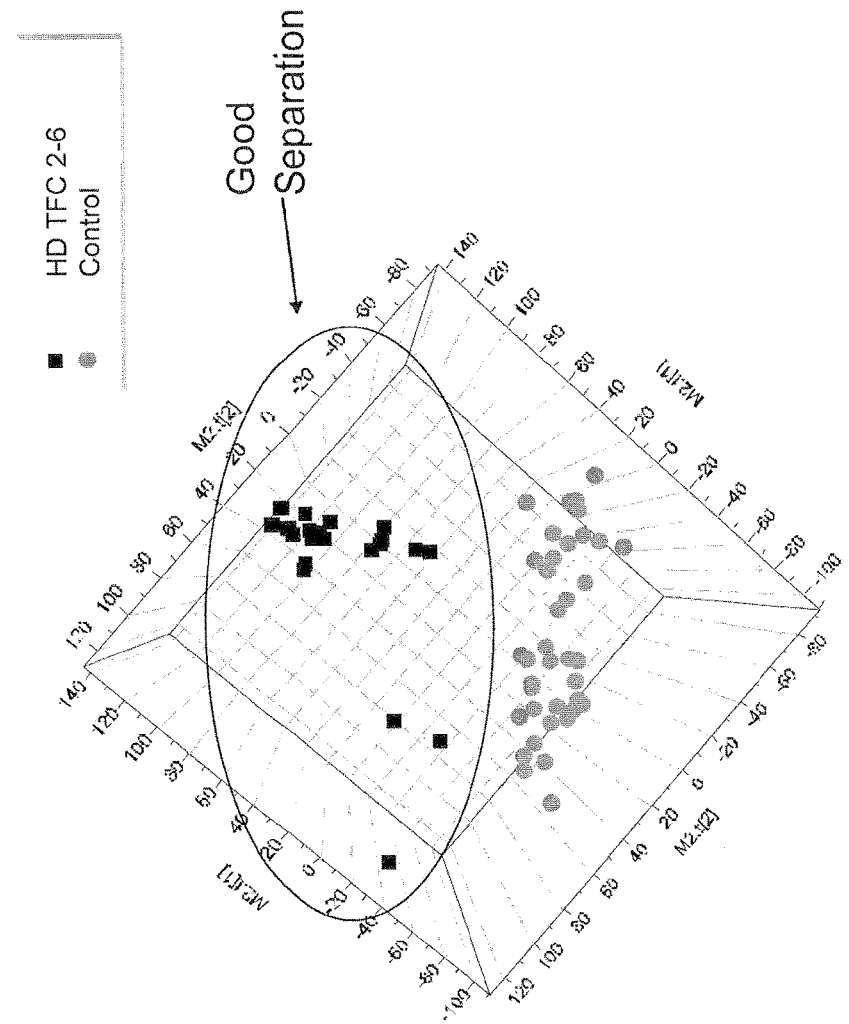
FIG. 6 is a partial least squares determinant analysis comparing control samples and HD patients with TFC scores of 2-6.

FIG. 6 is a PLS-DA comparing control samples (red) and all HD patients with TFC scores of 2-6 (black). Once again, good separation is visible. A list of VIPs is also shown in this figure. Those VIPs highlighted also appear to be present in at least 80% of the samples examined, which minimizes the risk that they are drug metabolite—related peaks or artifacts.

Figure 7:
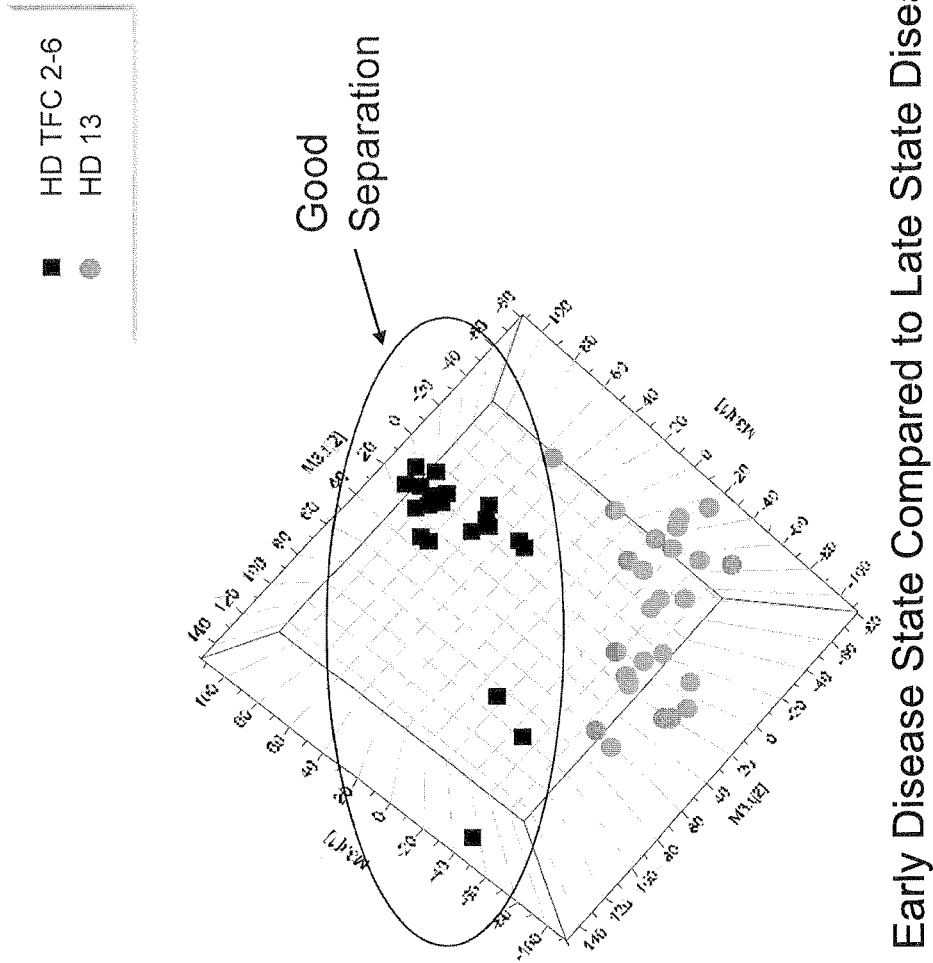
FIG. 7 is a partial least squares determinant analysis comparing early stage HD patient samples with TFC scores of 13 to late stage HD TFC scores of 2-6.

FIG. 7 is a PLS-DA comparing HD patient samples with TFC score 13 HD samples (red) with TFC scores 2-6 (black). Again, the VIP list is provided and the compounds highlighted appear to be present in at least 80% of the samples, which once again, minimizes the risk that they are drug metabolite related peaks or artifacts. Once we had obtained out list of candidate biomarker compounds, it was necessary to translate over to the parallel LC-EC array-MS system.

As before, a parallel LC-EC array-MS separation and detection system (red) was used to analyze all samples (black). A similar system consisting of a binary HPLC pump connected to a normal bore C-18 column followed by a 9:1 passive flow splitter that divided the eluant between the EC array and MS detectors was used for data acquisition. The MS flow rate was maintained at 80 μl/min in order to minimize possible ion suppression effects from both the biological samples and the high salt containing EC array buffers and facilitate efficient ion transfer. Additionally, the flow split was important for preserving agreement of the retention times between the EC array and the MS chromatograms in order to allow confident comparison between the results from the two instruments and identification of potential HD biomarkers. The delay times were adjusted such that a compound would be presented to the EC detector and the MS detector simultaneously within 1-2 seconds. The components of interest observed by the two detectors could subsequently be further characterized through the combination of high resolution MS measurements and CID tandem mass spectrometry (MS/MS).

Figure 8A:
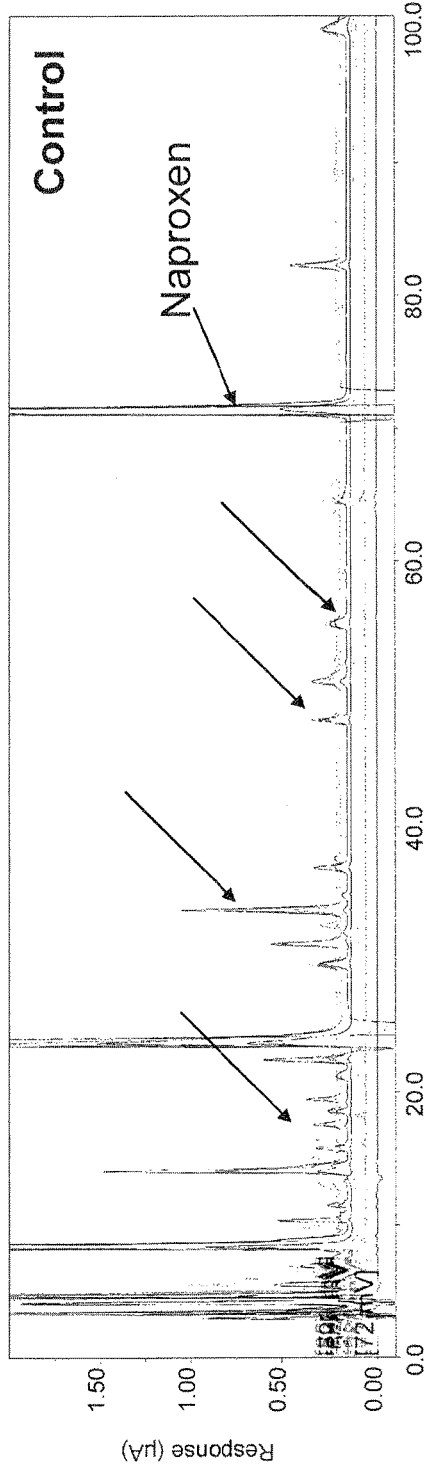
FIGS. 8A and 8B are a comparison of LC-EC array chromatographs of a control and HD subject respectively obtained from a 100-min gradiant method using the parallel system illustrating the ability of the technique to find un expected artifacts such as the un reported use of the pain medication Naproxen in survey studies of control vs. disease subjects.
Figure 8B:
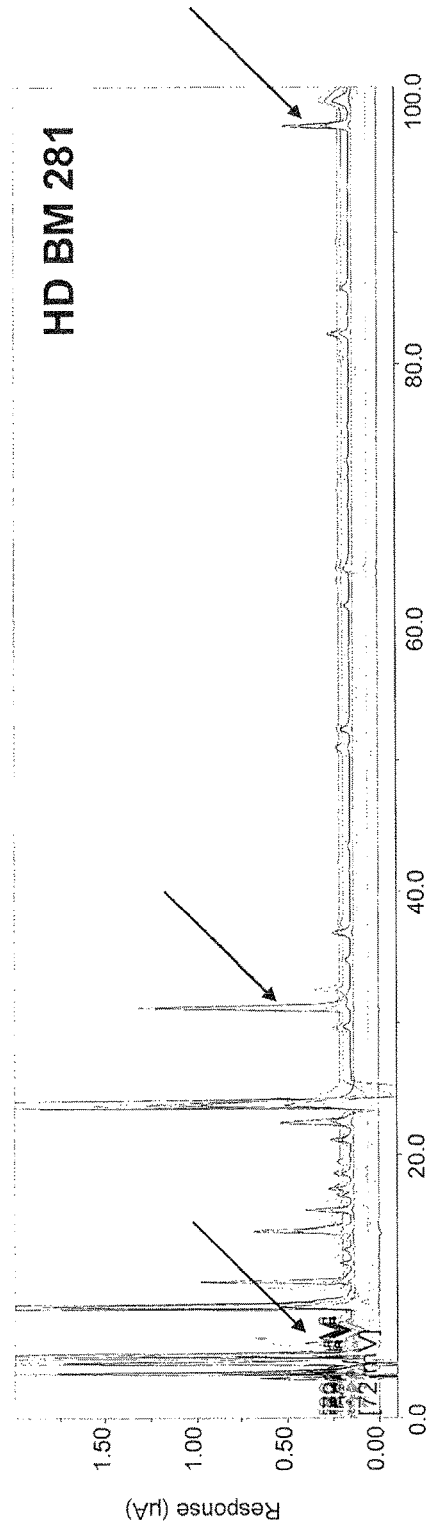

Shown in FIG. 8 is a comparison of LC-EC array chromatograms obtained from the 100-min gradient method using the parallel system. The top trace (A) is the chromatogram from one control sample and the bottom trace (B) is the chromatogram from one HD sample. Arrows point to some of the most prevalent differences between the two samples.

Since the most dramatic changes appeared between the control samples and HD samples with the lowest TFC scores, we decided to focus on these during the parallel LCEC array-MS analysis. Using the CoulArray software, we overlaid control and HD sample runs for visual inspection. Shown in FIG. 9 is an example of one peak of particular interest for which m/z determination was possible. Shown in panel A is the LCEC array peak corresponding to a proposed VIP. In panel B is the corresponding peak from the IDA method from the QStar MS. The peak shown in FIG. 9 was determined to have [M+H]+m/z 190.09 from the QStar IDA method in positive mode.

Figures 10A, 10B:
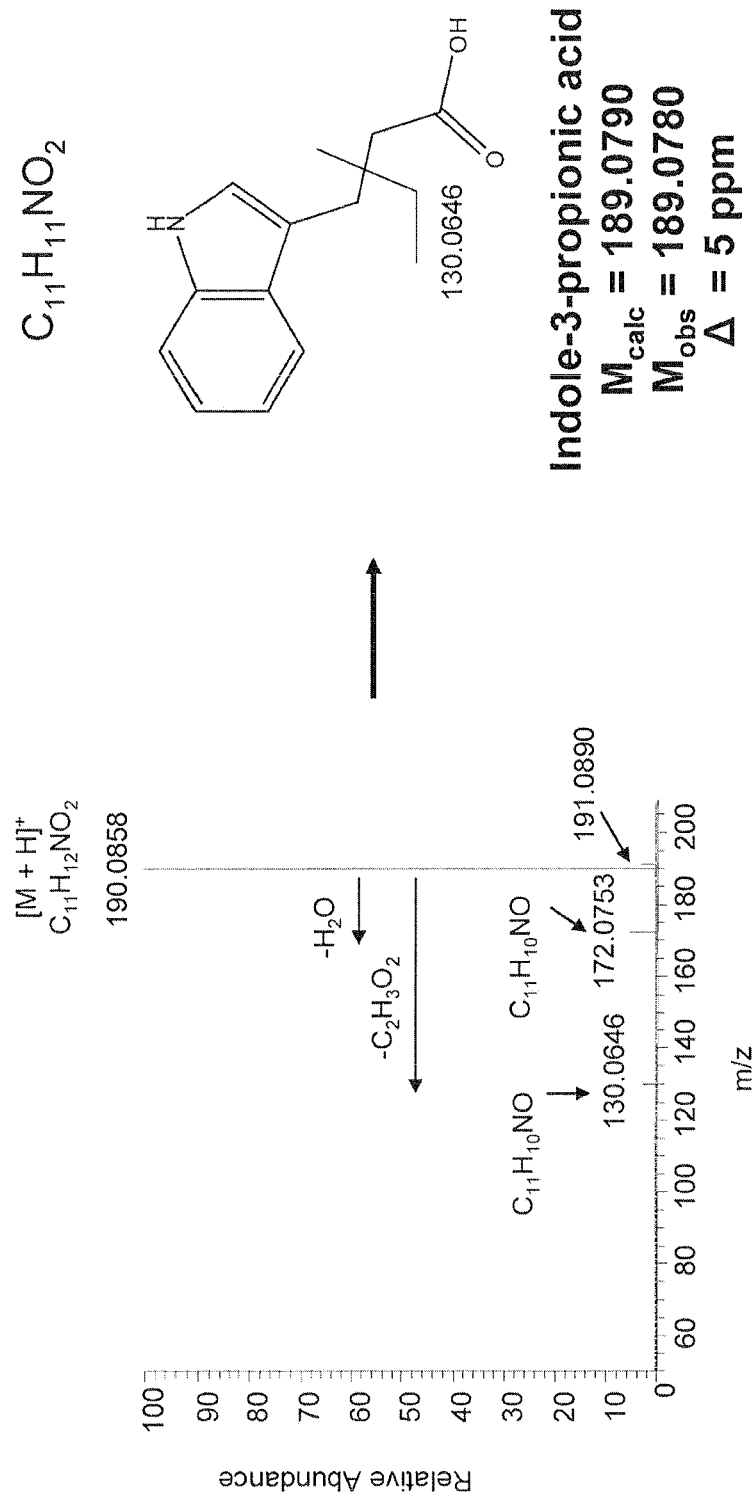
FIG. 10(A) is an MS/MS spectrum of the peak shown in FIG. 9.
FIG. 10(B) is a proposed structure for the candidate peaks.

Subsequent high resolution MS and MS/MS of the peak with [M+H]+m/z 190.0858 using the LTQ-Orbitrap yielded the fragmentation pattern shown in FIG. 10A. The fragments associated with the loss of H2O and C2H3O2 are indicated in the figure with m/z values of 172.0753 and 130.0646 respectively. From the fragmentation pattern we were able to assign the structure of the compound as indole-3-propionic acid (I3PA). This structure is shown in FIG. 10B. The observed mass of I3PA was 189.0780. The calculated mass for I3PA was 189.0790. The error was 5 ppm.

Provided in Table I are elution times and [M+H]+m/z values for each peak of interest taken from the QStar IDA method. These masses are believed to correspond to potential biomarkers.

Figure 11:
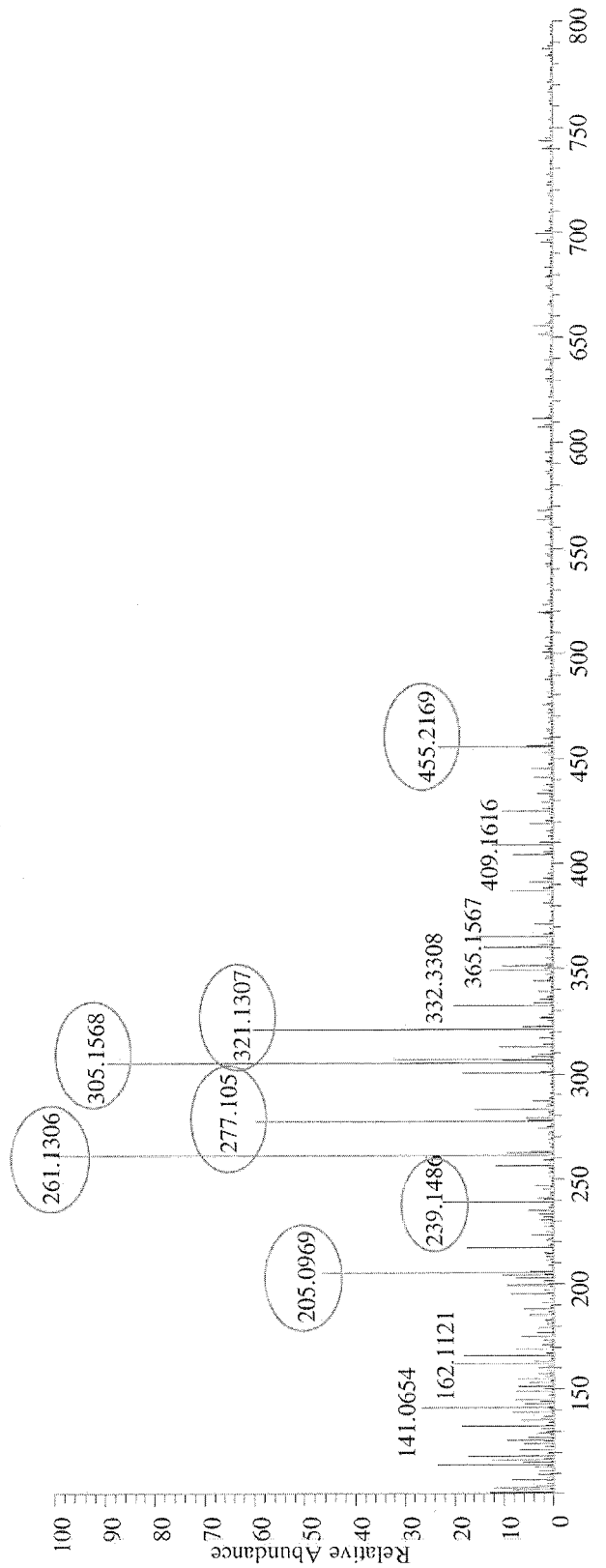
FIG. 11 shows the MS of a 30% acetonitrile fraction of control plasma.

We were able to see peaks in the range m/z 100-400 on the Orbitrap. Table I shows the m/z values found in mass spectra acquired using the SolariX that were measured for several compounds which differed between HD and control pools. Additionally, potential elemental compositions are provided in table I. FIG. 11 shows the MS of the 30% acetonitrile fraction of control plasma. Some of the most prevalent peaks are circled.

Figure 12:
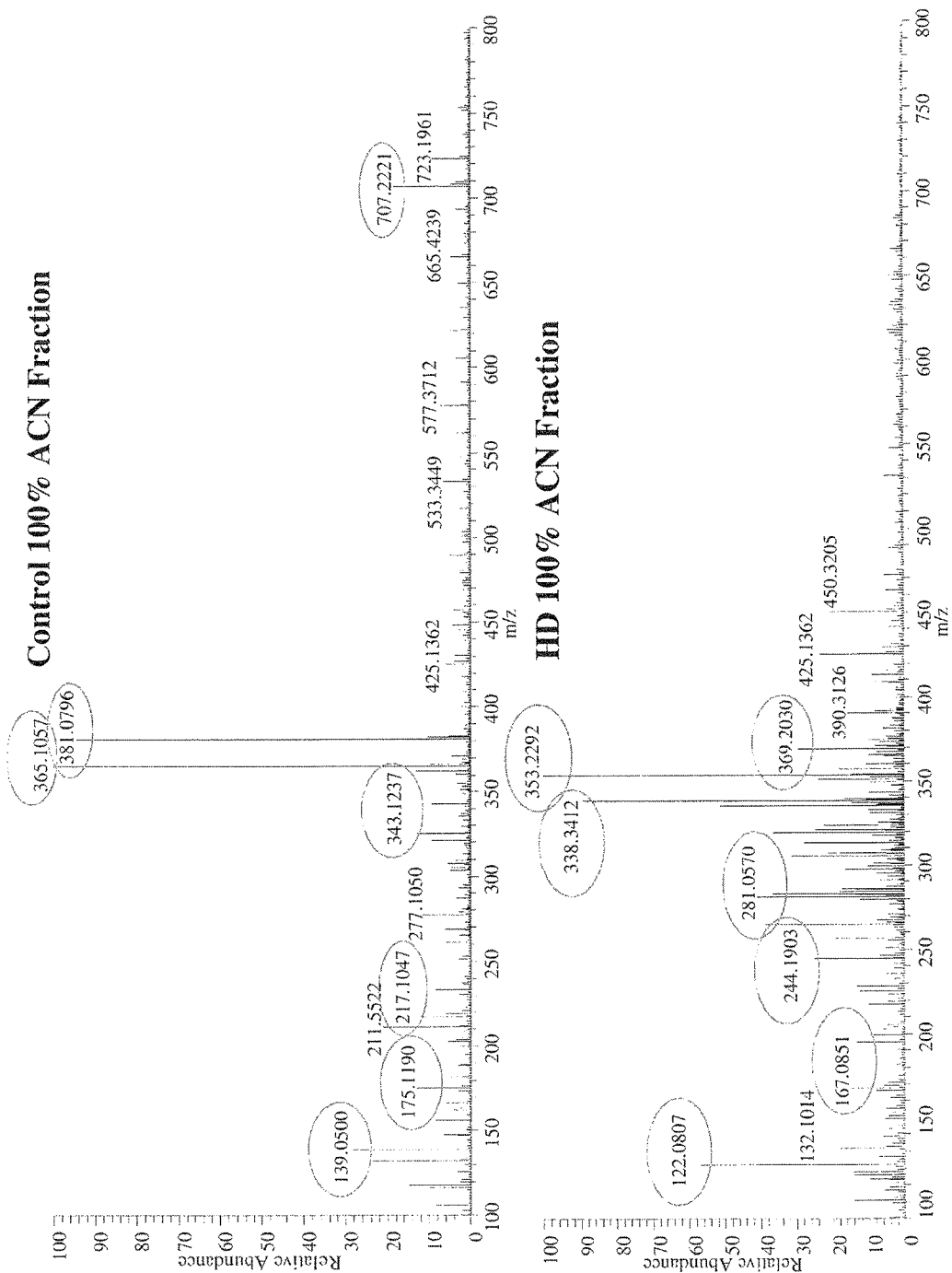
FIG. 12 shows the MS of a 100% acetonitrile fraction of control and HD plasma.

FIG. 12 shows the MS of the 100% acetonitrile fraction of control (top trace) and HD (bottom trace) plasma. The quantity of sample was sufficient to obtain MS data for both control and HD from the 100% acetonitrile fraction. Notable differences between the two are circled. In Table II, data from FIG. 11 and FIG. 12 has been organized for simplification. Several peaks from the 30% acetonitrile fraction from control plasma as well as the 100% acetonitrile fractions taken from both control and HD samples are listed including potential elemental compositions for each. A mass that correlated with one "biomarkers of interest" shown in Table I is highlighted in Table II.

Table III: Several peaks from the Orbitrap that were unique to the 30% ACN fraction from the control plasma pool and the 100% ACN fractions from both HD and control plasma pools are listed.*

* Potential elemental compositions are provided next to each m/z. None of these peaks coincided with IDA data from the QStar.

Figure 13:
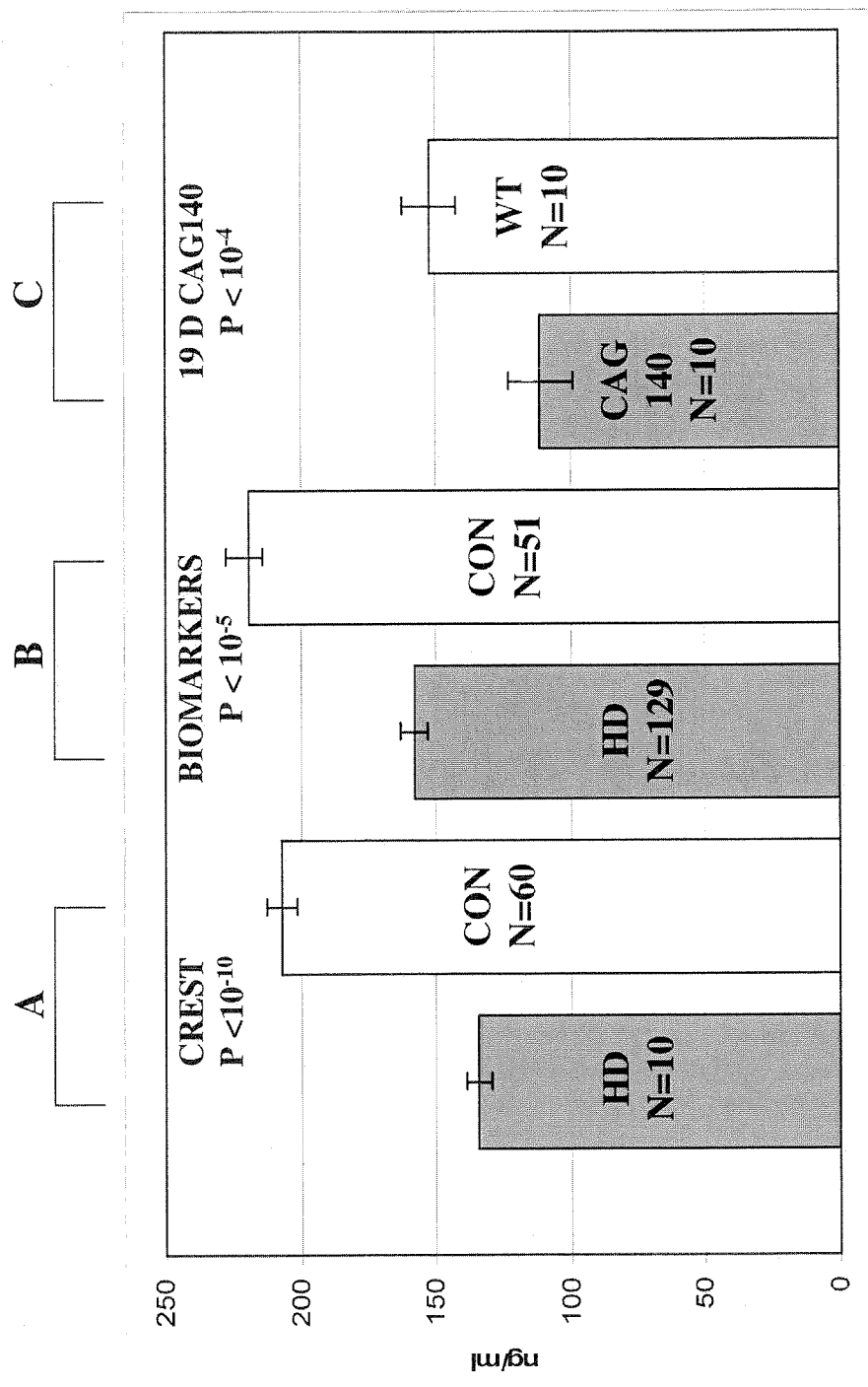
FIG. 13 is a digital map of levels of I3PA in diseased mice compared to levels of I3PA in wild-type litter mates.

We were able to identify one VIP as indole-3-propionic acid (I3PA). Subsequent re-injection of the I3PA standard at a concentration of 10-5 g/ml using the offline LC-EC array method, confirmed that the structure of the VIP was I3PA (shown in FIG. 13). FIG. 13 validates that I3PA is a differentiator between HD and controls. Shown are relative levels of I3PA in human HD, control, mouse model HD, and wild-type plasmas. Likewise, in FIG. 14, we have graphed I3PA levels in feces from R6/2 and CAG 140 Mouse N=9 (all $P < 10^2$). Results show that HD mouse feces have significantly less I3PA than the feces of their wild-type litter mates. Additional studies were performed on I3PA exclusively and will be described below.

Confirmation of I3PA

Indole-3-propionic acid (I3PA) has the molecular weight 189.2. It has a heterocyclic aromatic ring structure with high resonance stability. It is produced by two types of bacteria *Clostridium sporogenes* and *Clostridium cylindrosporum*, both of which are found in the small intestine. Although the full function of I3PA is unknown, I3PA has been described as a potential antioxidant in studies of Alzheimer β-amyloid protein; in these studies I3PA showed strong levels of neuroprotection in two examples of oxidative stress. Additional studies in mice and hamsters have shown that I3PA protects neurons from ischemia-induced neuronal damage by reducing DNA damage and lipid peroxidation. Given this information, it was of great interest for us to study both I3PA and its reactive intermediates. Since published reports have shown a correlation between oxidative damage and HD, determining whether levels of I3PA were consistently lower in HD patients was of interest. We were also interested in exploring why levels of I3PA were lower in HD patient samples.

Plasmas from the mouse model CAG 140 (19 days after birth) were obtained using the following method:

Samples of blood from the CAG 140 mouse model were collected by cardiac puncture. The blood samples were placed directly into an Eppendorf™ tube. Before the blood began to clot, 50 μl was removed from the tube into a separately labeled tube. Both samples were kept upright in dry ice until all collections were complete. All tubes were centrifuged at 8000×g for 20 min to separate red blood cells. Plasma was pipetted from of the top of the samples and stored at −80° C. All mouse plasma was then analyzed using the offline LC-EC array method as before.

Upon completion of plasma analysis, all chromatograms obtained from the above experiments were exported as digital maps as described above. Values of I3PA were averaged in the HD and control groups and two tailed t-tests were used to compare the levels of I3PA observed in the chromatograms of HD patient plasmas relative to each set of controls. Likewise, in the case of the plasmas obtained from the CAG 140 mouse model (at 19 days after birth), the levels of I3PA in the diseased mice were compared to the levels of I3PA in the wild-type littermates after averaging all values in each group. The results are shown in FIG. 13. The three pairs of bars correspond to the three groupings. The first pair are the average values of I3PA (ng/ml) in HD and control patients in the CREST (creatine dose escalation) study (A). The second pair are the average values of I3PA (ng/ml) in HD and control patients in the "Biomarkers Study" (B). The third pair are the average values of I3PA (ng/ml) in CAG 140 HD and WT collected 19 days after birth (C). Also shown on this figure are all p values describing I3PA's level of significance between disease and normal groups. Differences in I3PA levels are highly significant. In the CREST study, the p value is $<10^{-10}$. In the Biomarkers Study, the p value is <10-5. In the mouse model study, the p value is $<10^{-4}$. These results show that I3PA levels are lower in both human HD plasma and mouse HD plasma models as compared to their non-disease counterparts.

We observed that the differences in the levels of I3PA are statistically significant between diseased and control plasma in both human and mouse models. While not wishing to be bound by theory, we propose several hypotheses which might explain the lower levels of I3PA in the disease samples.

If human patients/mice with HD have lower plasma levels of I3PA, it suggests the possibility that the gut bacteria from these subjects are not producing as much I3PA as in non-disease subjects. Thus, it was of interest to determine whether this was the case.

Preparation and extraction protocol for mouse feces:

Feces were directly collected from mice and immediately placed on Dry Ice after collection. The feces were dried by roto-evaporation and weighed. Dried feces were extracted using acidified acetonitrile. Fifty mg feces were mixed with 1.2 ml of acetonitrile. The samples were sonicated for 30 min and centrifuged at 8000×g. One-ml of supernatant was removed and evaporated to dryness.

Samples from the procedure above were reconstituted in buffer as discussed above. The same LC-EC array method was used for analysis. All data was exported as digital maps as discussed above. Values for I3PA levels were compared and plotted.

Figure 14:
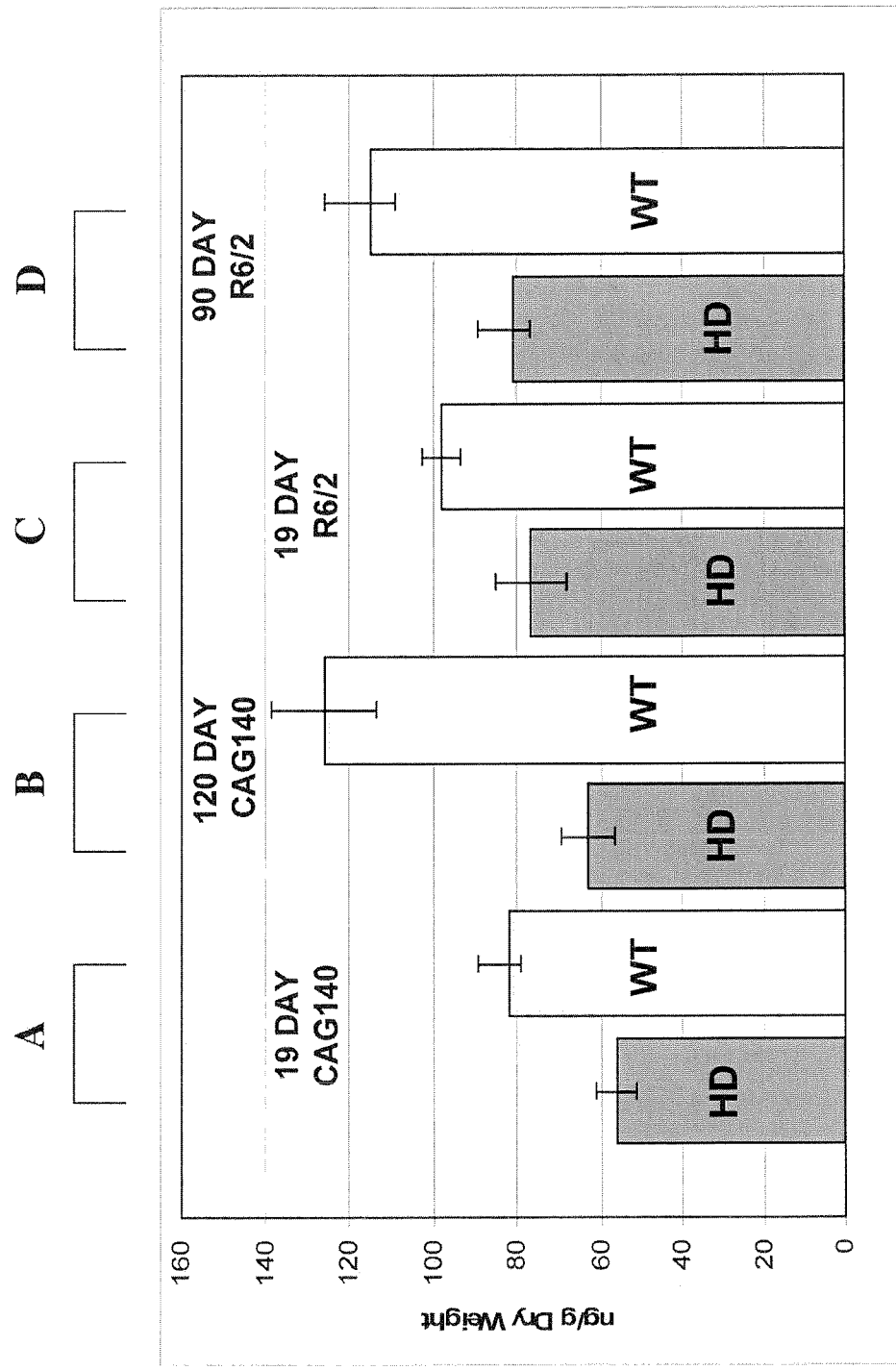
FIG. 14 is a bar graph showing results of analysis of mice feces.

Results from the analysis of mouse feces are shown in FIG. 14. In this figure there are four pairs of bar graphs. The first pair (A) shows a comparison of the amount of I3PA in mouse feces (ng/g dry weight) collected from 19 day-old CAG 140 HD mice and their WT littermates. The second pair (B) shows a comparison of the amount of I3PA in mouse feces (ng/g dry weight) collected from 120 day-old CAG 140 HD mice and their WT littermates. The third pair (C) shows a comparison of the amount of I3PA in mouse feces (ng/g dry weight) collected from 19 day-old R6/2 HD mice and their WT littermates. The fourth pair (D) shows a comparison of the amount of I3PA in mouse feces (ng/g dry weight) collected from 90 day-old R6/2 HD mice and their WT littermates. Each group had N=9 samples.

In all four cases the p values were $<10^{-2}$. Thus, we observed lower levels of I3PA in the feces of HD mice. The reduced levels could either be attributed to a) lower production of I3PA by bacteria; or b) fewer bacteria. While not wishing to be bound by theory, it has been suggested that I3PA undergoes an oxidation mechanism which ends in the formation of kynuric acid. This pathway is shown in FIG. 15.

We also were able to monitor the disappearance of I3PA over the course of 2 h using a Fenton reaction with the following conditions: 100 μM $H_2O_2$, 10 μM iron sulfate, 100 μM I3PA. The reaction mixture was kept at 4° C. in the dark. Every 30 min, a small aliquot of the reaction mixture was diluted 1:10 and injected onto the offline LC-EC array system. Although kynuric acid is not EC active, we were able to show the disappearance of I3PA.

Figure 15:
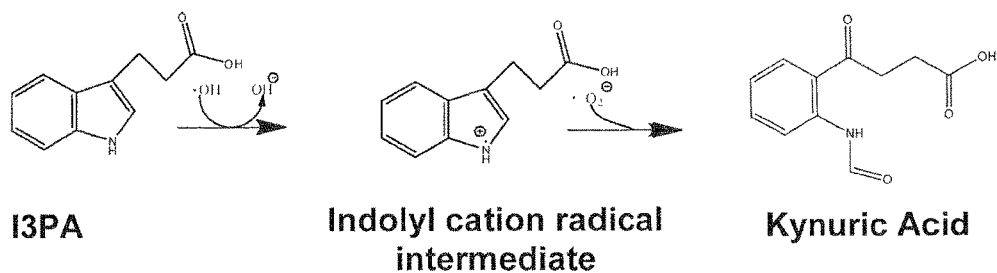
FIG. 15 is a suggested oxidation mechanism for I3PA.

If I3PA is subjected to free radical oxidation in patients with HD (which follows the logic that patients with HD are susceptible to high levels of oxidative damage), it would suggest that either the intermediate shown in FIG. 15 or kynuric acid itself might become a reactive species, capable of forming adducts with proteins. Accordingly, we were interested in determining whether kynuric acid was present in an unbound form in plasma. Thus, five randomly selected untreated HD patient plasmas were obtained, and were extracted as before the protein pellet was saved for later use. The supernatant of the plasma was analyzed for free kynuric acid using an LC-305 fluorometer (Linear, Alltech Associates, Deerfield, Ill., USA) set at excitation and emission wavelengths of 360 and 450 nm respectively. Loss of indole fluorescence was monitored at excitation and emission wavelengths of 285 and 345 nm. No free (unbound) kynuric acid was detected in plasma (LOD at 2% concentration of I3PA). This suggested that if kynuric acid had been formed, it was likely bound to protein.

Thus, it is seen that I3PA levels are lower at highly statistically significant levels in both HD human and HD mouse model plasma samples. While not wanting to be bound by theory, we believe that lower levels of I3PA may result from lower production of I3PA by bacteria in the small intestine. We were able to show that this is the case in two different mouse model examples (R6/2 and CAG 140) at two different collection time points (19 day and 120 day in CAG 140 and 19 day and 90 day in R6/2). However, it is unclear whether the decrease in I3PA production is caused by lower production rates of I3PA by bacteria or the presence of fewer bacteria. Another possibility for decreased levels of I3PA in plasma could stem from the conversion of I3PA into other products through an oxidation mechanism. Oxidative damage is suggested as a potential cause of neurodegenerative disorders such as HD. Thus, it is possible that I3PA is converted into other products as a result of elevated levels of oxidation. Since a primary product of the oxidation of I3PA is kynuric acid, we looked for the presence of kynuric acid in patient plasma. Using a fluorometer set at excitation and emission wavelengths of 360 and 450 nm, we looked for kynuric acid. However, none was detected.

Notwithstanding, while no free (unbound) kynuric acid was found in plasma of several randomly selected HD patients, it is believed that the kynuric acid may bind or other reactive intermediate(s) of I3PA to protein. In order to determine whether this was possible, Fenton reactions with I3PA and human serum albumin (HSA) (in vitro) standard were designed. Reaction mixtures were prepared as follows: 100 μM $H_2O_2$, 10 μM iron sulfate and 100 μM I3PA were combined with 1 μl of HSA (prepared at a concentration of 10 mg/ml). The reaction was incubated at room temperature for 1 h.

Two control and two HD plasma samples were selected at random from the "Biomarkers Study." Plasmas were prepared as per the same protocol discussed above. However, for metabolomics experiments the supernate was pipetted off and frozen at −80° C. and we focused on analysis of the protein pellets. Pellets of HD and control samples were washed with 500 μl of $H_2O$ twice to remove acidified acetonitrile. Water (250 μl) was added to the HSA-I3PA mixture. A solution of proteinase K (5 μl) which had been pre-filtered with a 1OK Centracon™ prep filter to remove contaminants (at a starting concentration of 10 mg/ml) was also added to the combined mixture. Samples were then placed in a water bath at 57° C. overnight.

An aliquot of the PK solution (1-μl) was added to all protein samples that had been subjected to the Fenton reaction with I3PA. Samples were vortexed and placed in a water bath at 57° C. overnight.

All samples which had been in the 57° C. water bath were removed and reextracted with the same protocol discussed above. 125-μl was precipitated with 500 μl of ACN/0.4% acetic acid, vortexed for 30 s, and centrifuged at 21,000×g for 25 min at 4° C. The supernatant (500 μl) was centrifugally evaporated and reconstituted to 100 μl in mobile phase A; a 50-μl aliquot was injected onto the LC-EC array system. LC-EC array analyses were performed using ESA model 582 Pumps (ESA Biosciences Inc., Chelmsford, Mass.) and a 16-channel ESA model 5600 CoulArray detector. Channels 1-15 used series coulometric electrodes set in equal increments of 56 mV from 0-840 mV. Channel 16 was set at 870 mV. Two 4.6 mm×250 mm series C18 5-μm columns (ESA Biosciences Inc, Chelmsford, Mass.) were used. The gradient employed was linear from 0% Phase A (0.1 M sodium pentane sulfonic acid with 5% acetic acid) to 100% Phase B (80/10/10 methanol/isopropanol/acetonitrile with 0.06 M lithium acetate; 7% acetic acid). The linear gradient was employed to 84 min, then 100% B was run to 110 min. The flow rate was 1 ml/min.

Figure 16:
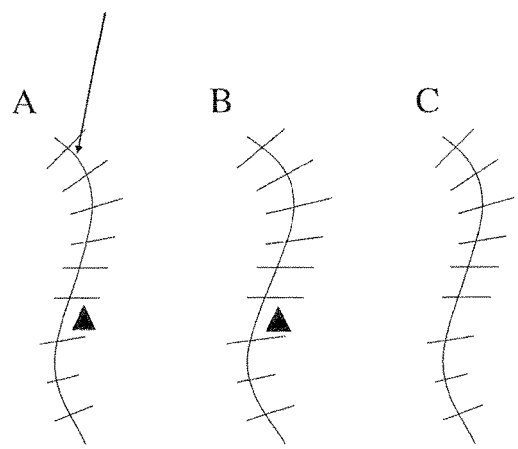
FIG. 16 is a representation of a PK digested fragment.

Results:

A comparison of the data obtained from the PK digests of in vitro generated I3PA oxidation products bound to HSA and the PK digests of HD and control protein pellets indicated similarities. FIG. 16 shows an illustration representing various PK digests. The PK digest of in vitro generated HSA reacted with I3PA in a Fenton reaction is shown in (A). (B) shows the PK digestion products of HD protein pellets. (C) shows the PK digestion products of un-reacted HSA. Similarities were observed in (A) and (B) and were not seen in (C) suggesting that an oxidation product of I3PA may have bound to the HSA.

Figure 17:
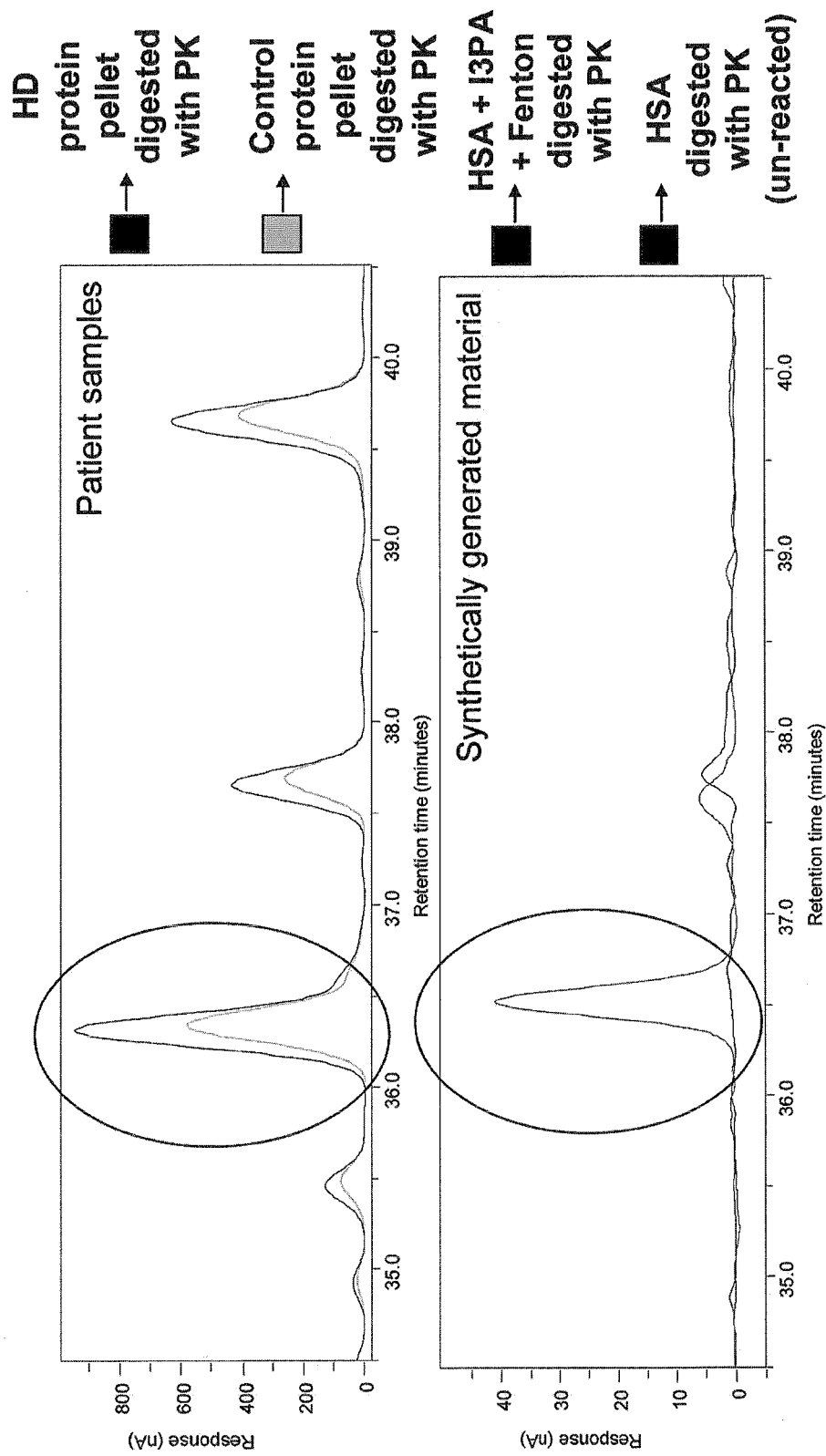
FIG. 17 are two LC-EC array chromatograms.

Additional evidence suggesting a similarity between PK digests of the in vitro created [HSA+I3PA+Fenton reaction] and PK digests of HD protein pellets is shown in FIG. 17. Here we see two LC-EC array chromatograms in the 34-41 min range. The blue trace in the top panel represents the HD protein pellet digested with PK. The green trace in the top panel represents a control protein pellet digested with PK. The red trace in the bottom panel represents the products of [HSA+I3PA+Fenton reaction] digested with PK. The black trace in the bottom panel represents HSA digested with PK. The circled peaks are suggested to have the same structure in the HD, control and in vitro generated material. Levels of the circled compound are significantly higher in HD protein pellet digests than in controls. We propose that these peaks correlate to an I3PA-related compound bound covalently to an amino acid or peptide fragment containing tyrosine or tryptophan, because these are the only two amino acids that are electrochemically active at the potentials applied.

Coulometric integration of the peak gives approximately 2 pmol from the 250 μl of plasma, which is estimated to be between 600-1200 pg or 2.4-4.8 ng/ml. The position of the peak in the chromatogram suggests that it is either bound to a single tyrosine or tryptophan, or to a di- or tri-peptide because its elution is early in the chromatogram relative to larger peptides such as the endorphins. This experiment suggests that one mechanism explaining the findings of significantly lower I3PA in HD plasma is due to the reaction of oxidative free radical intermediates of I3PA and subsequent binding of these intermediates with plasma protein.

The similar peaks found at higher levels in the HD digested protein pellets suggest that both lower production and increased oxidation of I3PA could be reasons for lower plasma levels of free I3PA being observed in HD.

We then investigated whether we could generate a covalently bound oxidation product of I3PA with a protein. Additionally, determined the structure of the oxidation product of I3PA and the binding site of the oxidation product on a protein. Two different models were used. These were ubiquitin and angiotensin I. Using MS techniques we hoped to identify the structure of the oxidation product and binding site.

Free Radical Binding of I3PA Oxidation Product to Ubiquitin

Preparation and Method:

A Fenton reaction was performed using the same concentrations of hydrogen peroxide, iron sulfate and I3PA as discussed above. One microliter of a solution of ubiquitin prepared to a concentration of 10 mg/mi was added to the mixture. In addition, a separate tube containing only the Fenton reaction without ubiquitin was prepared and labeled as the negative control. The reaction was kept in the dark at 4° C. for 16 h.

High resolution MS analysis of the reaction mixtures was performed using a 12-T Qh/FT-ICR hybrid mass spectrometer (SolariX, Bruker Daltonics) that was equipped with a nanospray source operated in the positive mode. Samples were diluted 1:10 in 50/50 methanol/water, 0.5% formic acid and analyzed on the SolariX. Detection of ions in the SolariX was obtained at a resolution of approximately 110,000.

Results:

Analysis of the data obtained on the SolariX indicated likelihood of a non-covalent interaction between an oxidation product of I3PA and ubiquitin. An illustration is provided in FIG. 18 demonstrating the attachment of I3PA to ubiquitin as a result of the Fenton reaction.

Shown in FIG. 19 are four mass spectra from the region m/z 794-804. Visible in the bottom spectrum are several peaks. An oxidation product of I3PA is shown bound to ubiquitin in (D). Binding occurs when a Fenton reaction occurs in the presence of I3PA and ubiquitin. In all other cases, no bound material is detected. The circled peak corresponding to $[M+11H]^{1+}$ m/z 799.25584 is found only in the sample containing I3PA, the complete Fenton reaction and ubiquitin. The remaining four spectra corresponding to: ubiquitin alone (A), ubiquitin and I3PA without the Fenton reaction (B) and ubiquitin plus I3PA with Fenton reaction without iron sulfate (C) do not show the presence of this peak.

Based on a comparison of the isotopic patterns of the peaks in FIG. 19 to the theoretical isotopic distributions of both the covalent and non-covalent adducts of kynuric acid to ubiquitin, it is believed that the circled clusters of peaks correspond to two different binding types. The first, circled with a solid line and labeled Coy corresponds to [M+H]$^+$ m/z 8779.7598. This peak corresponds to covalently bound kynuric acid. The second, circled with the dotted line and labeled Non-Coy corresponds to [M+H]+m/z 8781.7492. This peak corresponds to residual co-coordinately bound kynuric acid. FIG. 20 shows the region m/z 799.0-800.4 magnified with "peaks" indicating the isotopic patterns of both the covalent and non-covalent forms of kynuric acid. The isotopic pattern for covalently bound material is outlined in black. The isotopic pattern for co-coordinately bound material is outlined in green. Overlap was observed because of the small mass difference (2 Da) between the two.

Without wishing to be bound by theory, it is believed that the formation of co-coordinately bound kynuric acid reflects the direct conversion of the intermediate free radical to a kynuric acid during the Fenton reaction before it encounters a protein binding site. Because the two forms are so close in mass, the isotopic clusters overlap. A calculation of a theoretical value for ubiquitin ([M+H]+m/z 8560.6287) plus a covalently bound kynuric acid ($C_{11}H_{11}NO_4$, exact mass 221.0688) predicts [M+H]m/z 8779.7577 for such an adduct. The same calculation with ubiquitin and a non-covalently bound kynuric acid predicts [M+H]$^+$ m/z 878 1.6975 for such an adduct. The [M+H]+m/z of the first peak was reported as 8779.7598. The [M+H]$^+$ of the second peak was observed at m/z 8781.7492. This would correspond to a calculated error of −0.24 ppm for the covalently bound material and −5.8 ppm for the non-covalently bound kynuric acid. In this spectrum, the calculated measurement for the observed peak assigned to ubiquitin corresponds to a measurement error of −5.3 ppm. These results were confirmed when the sample was infused via nanospray onto the LTQ-Orbitrap. The [M+H]$^+$ of the first peak that we suggest corresponds to kynuric acid covalently bound to ubiquitin was observed at m/z 8779.6766, a measurement error of 9 ppm. The second peak that we suggest corresponds to kynuric acid non-covalently bound to ubiquitin was observed at m/z 8781.6989, a measurement error of −0.16 ppm. It is therefore likely that the circled peaks correspond to both kynuric acid covalently and non-covalently bound to ubiquitin (as there is only a 2 Da shift between the two). The two additional peaks [M+11H]$^{+11}$ m/z 800.70945 and 801.98019 are likely oxidized forms of the non-covalently bound kynuric acid/ubiquitin moiety.

In ancillary studies we measured the parent binding constants for I3PA with whole human plasma, HSA, BSA and ubiquitin using serial additions of I3PA to determine the number of molar equivalents of binding sites and mole equivalents of free I3PA. The binding constants (pk) for whole human plasma, HSA and BSA are one the order of 10$^3$ or greater than for ubiquitin alone. This would suggest that our data for ubiquitin in which we saw both covalently and co-coordinately bound kynuric acid, was realistic. Increasing the concentration of materials in the Fenton reaction resulted in the over creation of co-coordinately bound kynuric acid, as the I3PA intermediate free radical converted to kynuric acid prior to encountering a protein binding site. Thus, efforts to increase the yield of covalently bound kynuric acid were prevented by over generation of non-covalently bound material. We then decided to attempt this Fenton reaction with I3PA using angiotensin I as the peptide target.

Preparation and Method:

Angiotensin I was obtained from The American Peptide Co in Sunnyvale, Calif., USA. Six tubes were prepared with the following Fenton reaction mixtures: Tubes 1 and 4 contained 100 µM $H_2O_2$, 10 µM iron sulfate and 100 µM I3PA; Tubes 2 and 5 contained 100 µM $H_2O_2$, 100 µM iron sulfate and 100 µM I3PA. Tubes 3 and 6 contained 100 µM $H_2O_2$, 200 M iron sulfate and 100 µM I3PA. Tubes 4, 5, and 6 also contained 1 µl of angiotensin I prepared to a concentration of 10 mg/ml. A separate tube containing only the Fenton reaction without angiotensin I was prepared and labeled as the negative control. The tubes containing the reaction mixtures were covered with aluminum wrap so that none of the reagents would deteriorate in the ambient light. All reaction mixtures were kept on ice. The tubes were left to react for 30 h.

SolariX MS of Angiotensin 1 Plus Fenton Reaction Mixture.

High resolution MS analysis of the reaction mixtures was performed using a 12-T Qh/FT-ICR hybrid mass spectrometer (SolariX, Bruker Daltonics) that was equipped with a nanospray source operated in the positive mode. Samples were diluted 1:2 in 50/50 methanol/water, 0.5% formic acid (for positive-ion mode) or 50/50 methanol/water, 0.05% triethylamine (TEA) (VWR Scientific, PA, USA) (for negative-ion mode) and were analyzed on the SolariX in positive and negative modes. Detection of ions in the SolariX was obtained at a resolution of approximately 110,000. MS/MS fragmentation was performed using CID at 0-10 eV.

Analysis of the reaction tube containing the Fenton reaction products and I3PA without angiotensin I determined that the primary reaction product had [M−H]$^-$ m/z 220.0621. This product was only seen in negative mode on the MS. Fragmentation of this compound indicated that the likely structure corresponded to the anion of kynuric acid [$C_{11}H_{10}NO_4$]$^-$. Shown in FIG. 21 is the MS/MS spectrum of the ion corresponding to [M−H]$^-$ m/z 220.0621. The fragment at m/z 202.0503 corresponds to the loss of $H_2O$. The fragment at m/z 176.0710 corresponds to the loss of $CO_2$. The fragment at m/z 158.0605 corresponds to the loss of both $CO_2$ and $H_2O$. The fragment at m/z 148.0398 corresponds to the loss of $C_3H_4O_2$. The calculated value for the [M−H]$^-$ of kynuric acid is m/z 220.0610. The observed value was m/z 220.0609. The error was 0.45 ppm. Thus, it is likely that this structure corresponds to kynuric acid.

Analysis of the reaction tubes containing the products from the Fenton reaction, I3PA and angiotensin I determined that fraction 4 contained the highest quantity of "unique products." MS/MS of the peak [M+H]$^+$ m/z 1515.7413, which we theorized corresponded to the covalently bound oxidation product of I3PA (kynuric acid) to angiotensin I was performed.

Table IV provides b- and y-ion fragments of angiotensin I including observed values, theoretical values and ppm error. Also shown are all observed fragments containing covalently bound kynuric acid, likewise including observed and theoretical values as well as the ppm error. FIG. 22 shows the MS/MS spectrum of the product which has been assigned as kynuric acid (KA) covalently bound to angiotensin I (boxed in blue) represented by the peak with [M+3H]$^{3+}$ m/z 505.9175. Both b- and y-ions are labeled. Boxed are m/z values of b- and y-fragments containing covalently bound kynuric acid are boxed in red.

The first covalently bound member of the series was [M+H]⁺ m/z 753.3192. This peak corresponded to [b₄+kynuric acid]. Also present was [M+H⁺]m/z 866.4036 which corresponded to [b5+kynuric acid]. [M+H]⁺ m/z 1003.4624 corresponded to [b₆+kynuric acid]. [M+2H]²⁺ m/z 624.2948 which corresponded to [b⁸+kynuric acid]. [M+2H]²⁺ m/z 692.8247 which corresponded to [kynuric acid+b₉]. Also observed were [M+3H]³⁺ m/z 415.5549 which correspondence to [ys+kynuric acid]; and [M+3H]³⁺ m/z 467.5738 which corresponded to [y9+kynuric acid].

Because this series of fragment ions was observed to start at [b₄+kynuric acid], it is believed that the kynuric acid is bound on Tyr4. It was to be expected that binding of kynuric acid would have occurred on tyrosine, because the aromatic ring on tyrosine is a common point for free radical attack of reactive nitrogen and oxygen species.

Examining plasma data from three separate studies, the "Biomarkers Study", the CREST study and a study using the CAG 140 mouse model, we determined that plasma levels of I3PA in diseased samples were significantly lower than in non-disease controls. The discovery of the marked decrease in plasma I3PA levels led to an investigation of possible reasons for this phenomenon. Two hypotheses were proposed. First, because I3PA is produced by bacteria in the small intestine, it was of interest to determine whether the levels of I3PA in fecal matter of diseased patients was lower than that found in non-disease patients. Although we did not have access to human samples, we were able to use R6/2 and CAG 140 mouse feces which had been collected at two different time points. In all four cases, the diseased mice showed significantly lower levels of I3PA in their fecal matter as compared to the non-diseased wild-type controls. These results suggested that either the bacteria were producing less I3PA in diseased mice, or that there were fewer bacteria. Thus, the presence of the disease genotype clearly resulted in lower levels of I3PA production and excretion.

A second hypothesis describing why I3PA levels were lower in diseased patient plasma stemmed from the theory that oxidative damage, highly prevalent in neurodegenerative disorders such as HD, caused the I3PA to be converted into an oxidation product, lowering levels of I3PA and perhaps creating a protein-bound oxidation product of I3PA. A potential oxidation product of an in vitro reaction "mimicking" oxidative damage in the body was considered. We then sought to determine whether any kynuric acid was present in UD plasma. Although kynuric acid is not an electrochemically active structure, using a fluorometer, we investigated whether any kynuric acid was present in HD plasma. None was detected. A second possibility was that the kynuric acid had become bound to a plasma protein. In order to determine whether this type of reaction could occur in vivo, an in vitro reaction was simulated to mimic free radical oxidation of I3PA in the presence of angiotensin I and ubiquitin. Using MS we were able to determine that kynuric acid bound both covalently and co-coordinately to ubiquitin as well as covalently to angiotensin I. We identified the covalent binding site of kynuric acid on angiotensin I to be Tyr4.

Lastly, we compared PK digests of HD and control protein pellets to in vitro generated covalently bound oxidation products of I3PA to HSA. We prepared Fenton reaction solutions containing I3PA and HSA. These were digested with PK and compared to PK digests of UD and control protein pellets using the offline LCEC array method. Several similarities were detected, suggesting the possibility that an oxidation product of I3PA (possibly kynuric acid) was indeed bound to the HD protein pellets, possibly somewhere on HSA.

Various changes may be made in the above disclosure without departing from the spirit and scope thereof. Indeed, my investigation of ANOVA and ABNOVA analysis of the 612 subjects for whom we had serial samples with the null hypothesis that variance of the data was due to variance with individuals gave a p value of less than 10 exp-16 indicating strongly that in the absence of intervention IPA levels are an individual specific characteristic.

The information indicates that low levels of IPA are associated with four major neurological diseases and with ischemic heart failure and stress related events in heart failure subjects.

Moreover, as discussed below low levels of IPA are an individual characteristic determined in part by the effect of an individual's genome on the aggregate genome of the gut microbiome and thus are a genetically determined risk factor in the development of disease. This insight implies that population wide screening for IPA using techniques based on the rapid methods described and providing a means of increasing IPA levels through direct supplementation or modification of the gut microbiome through use of agents such as Froximum or dietary manipulation will provide a population wide decrease in degenerative or late onset diseases. Particularly those in which oxidative stress, related mitochondrial dysfunction and protein damage and aggregation are an eventual effect cumulative insult.

Methodology also has been developed for direct monitoring of the aggregate composition of the gut microbiome using fecal material.

In mouse trials sample acquisition is relatively simple involving only collection of fecal pellets and processing them with dry weight as a normalizer of values to obtain a metabolomic pattern reflecting the aggregate "footprint" of the gut microflora. Interpretation of differences is made simple because of the consistency of diet.

Measurement of such patterns in wild type and gene modified mice as shown below indicate that even at a very early age the footprint of the gut microflora is strongly influenced by the genome of the animal itself. Indeed we have determined that the microbiome foot print uniquely separates wild type mice from their gene positive littermates at weaning well before any onset of symptoms, or any measures of histopathology. An example is shown in FIG. 23 for young and old CAG 140 HD mouse models. Two of the variables of importance with the highest values in discriminating these gene positive and wild type mice from feces are IPA and the ratio of IPA to Indole lactic acid, with lower IPA and higher IPA/indole lactic acid in the gene positive mice.

Thus the genome that eventually determines the onset of disease also determines the aggregate makeup of the gut microbiome in an individual.

A second example incorporating the use of gut microflora modification is shown in FIG. 24. Administration of the compound Froximum (a folk remedy comprised of volcanic ash) changes the metabolomic profile of the G93a mouse brain, spinal cord and blood. However, this compound by its nature as an inorganic ash cannot cross the gut to plasma or the plasma to brain. The effect is on the aggregate gut microbiome which is then subsequently reflected in beneficial changes in other organs. As shown in FIG. 24 the separation of treated and untreated ALS model G93A from the changes in the microbiome footprint are sufficient to uniquely discriminate treated and un treated mice-in this case moving the ALS mouse model closer to the state of the wild type littermates. Again IPA was a strong variable of importance in this separation and lower in the gene positive mouse and elevated in both the treated gene positive and wild type littermates. The micro biome footprint of the G93a, CAG 140 and their respective wild type littermates were also significantly different from each other.

This indicates that: first a therapeutic compound for CNS disorders does not necessarily have to cross the blood brain barrier to have a profound effect on the network of genomic proteomic metabolomic and gut microbiome interactions that are beneficial to health and or deleterious to health; second that a compound that my cross the Blood brain barrier may also have a secondary effect on the gut microbiome that can be either beneficial or deleterious.

First implication is that strategies to prevent or delay the onset of symptoms of CNS diseases with a genetic component or predisposition such as Huntington's Alzheimer's, Parkinson's or ALS should include approaches to the modification of the aggregate makeup of the gut microbiome, and that these approaches should be undertaken at a very early stage prior to the onset of any potential systems. Essentially the aggregate composition of the gut microbiome like the individuals genome itself is a risk factor in neurodegenerative disease. However this individual aggregate gut microbiome genome can be more readily modified to a more beneficial state than that of the individual themselves.

Second implication is that in any trial of a potential therapeutic the foot print of the gut microbiome should be monitored. Changes introduced by a therapeutic agent could be beneficial or harmful and such changes can be compared against a data base for compounds in either category. Significant changes in the individuals gut microbiome which is stable without significant intervention can also be monitored To implement this approach we developed a protocol that could be applied to both monitoring without necessity of a clinical visit in a drug trail and to population based screening if indicated In humans monitoring of the gut microbiome footprint is more complex because of issues related to sample acquisition and interpretation because of dietary variation. The first issue has been addressed by simply taking a piece of used toilet paper after a bowel movement and placing it in a 50 ml tube containing 70% isopropanol (rubbing alcohol a common use material) which can be stored refrigerated and subsequently shipped to a laboratory.

Direct analysis of the supernate or supernate concentrates from the tube yields patterns as shown in (FIGS. 25A, B, and C) from baseline samples in the short proof of principle study of the time stability of the individual gut microbiome in a husband and wife described below. The technical innovations are in normalizing the data and in development of a statistical approach to eliminating dietary variations.

Initial normalization on concentrated aliquots is performed by centrifugal evaporation in tared tubes and diluting with running buffer to equivalent concentrations in g/ml.

Secondary Normalization for data analysis and profile matching is done by quantitatively analyzing the all resolved peaks against a pooled sample and taking the ratio of each peak to all others. i.e. in this example with 785 resolved peaks the number of ratios and values for analysis is 308,505.

Dietary variations are expected to have inconsistent ratios whereas compounds that are direct precursors and products of microbial metabolism are expected to be relatively consistent assuming no significant change in the aggregate microbiome.

In classifying individuals from serial samples using all ratios in PCA or supervised PLS-DA models the ratios of compounds that reflect aggregate gut microbiome activity would be expected to be the dominant variables of importance discriminating one individual from another, and the most significant variables defining a change from individual temporal similarity reflecting a change in the gut microbiome.

An example of this approach is shown in FIG. 24. Fecal material on toilet paper was acquired from a husband and wife sharing similar diets and medications over a period of 15 days by placing used toilet paper into a 50 ml tube containing 70% isopropanol. One sample was collected from the husband following 5 days of post dental reconstruction antibiotic therapy at day 20 (outlier in blue). Samples were maintained at 4 C until assay. Patterns were developed and ratios obtained as described above. The data was then analyzed by PLS-DA modeling. The variables with the highest Variable of importance values (greater than 2.5) were all compound ratios. One out modeling showed a consistency of variables of importance for the separation the principle known compound ratios were IPA/indolelactic acid, IPA/cresol, cresol/tyrosine, tryptophan/indoleacetic acid and tryptophan/IPA.

This indicates that even in the same environment the aggregate gut microbiome of two individuals is different. Supporting the influence of the individual's genetic makeup on the structure of the microbiome. It is an open question as to whether the metabolic foot print of the microbiome will be a better discriminator of individuals than the aggregate gene mapping of the microbiome.

FIG. 26 illustrates the first criterion for selecting compounds for targeted methods is that is a progressive biomarkers-as shown by the trend from C to PMHD to HD in the left hand panel for IPA. A practical criterion is stability. In the second panel stability of IPA in plasma shows only 5% degradation after 7 days at room temperature. Method development then involves integrating simplest preparative and instrument protocols for speed and minimum sample size and interferences. A preparative protocol using a simple 3:1 addition of methanol to plasma centrifuging and injecting supernate was matched to a mobile phase, column and detector settings allowing sensitivity to 2 ng/ml, linearity across the range and analysis with no currently determined interferences. The method was also adapted to brain feces and urine for animal trials to demonstrate the congruence of the biomarker in humans and HD mouse models as a desirable condition for using mouse models in therapeutic trials. The third panel illustrates the application of the method to mouse urine in a dose loading study of IPAM showing two metabolites in dosed animals (green) and the same two metabolites in un dosed mice (blue) and in human urine (red). The dosed animal urine provided sufficient material for isolation and MS determination as probable glucuronide type Phase II metabolite compounds with M/Z of 480.14 and 482.15 respectively FIG. 27A provides a comparison of plasma sub aliquots using the targeted IPA method vs. values derived by integrating the dominant leading and following peaks in the chromatograms from the long gradient survey method. The duplicate pair 11% rsd between the methods is trivial with respect to the biological variability of 100-125% rsd. This study allowed the derivation of accurate values from archived chromatograms from the last 21 years in which the IPA was present as a signal that had not been structurally identified or included in the mixed calibration standard used for all assays at that time.

Referring again to FIG. 23, the left hand panel shows one of a series of (two out) tests of the PLS-DA model for assessing the degree to which the foot print of the gut microbiome reflected in the dry weight normalized coordinately bound LCECA patterns of feces allows categorization of young 19 day littermate WT and GP CAG 140 mice. Training sets of 8 and validation sets of 2 are sequentially evaluated for all samples. In the example shown both GP and one WT were correctly classified. A similar model for old 90 day WT and GP CAG140 mice is shown in the left hand panel where both were correctly classified. Overall for the young an old categories CCR is 0.83 and 0.81 respectively. That suggests that we can currently categorize genetic status of a mouse by its microbiome foot print about 80% of the time even prior to any symptoms.

FIG. 24 illustrates fecal patterns of the gut microbiome footprint show complete categorical separation for the ALS mouse model G93A (ALS in red) and wild type littermates (WT in black). Froximum treated WT and TRTWT and G93A TRTALS in blue and green move to a different space in which they are more congruent with each other. Similar although categorically weaker separations are seen in the metabolic profiles of post mortem brain and spinal cord.

FIG. 25A illustrates a pattern of gut microbiome footprint from isopropanol extract of approximately equal quantities fecal material on toilet paper at low amplification of 10 ua full scale for two individuals (1 and 2)

FIG. 25B shows a pattern of gut microbiome footprint from isopropanol extract of approximately equal quantities fecal material on toilet paper at medium amplification of 1 ua full scale for two individuals (1 and 2)

FIG. 25C shows a pattern of gut microbiome footprint from isopropanol extract of approximately equal quantities of fecal material on toilet paper at low amplification of 500 ua full scale for two individuals (1 and 2) showing regions of significant differences.

FIG. 28 shows a PLS-DA 3 component model of gut microbiome footprint signatures derived from toilet paper fecal samples placed into 35 ml of 70% isopropanol 50 ml tubes and processed for LCECA profiles. 6 samples over a 15 day period from wife (red) and 7 samples over a 15 day period from husband (black) and one taken at 20 days after use of an antibiotic post dental surgery shown in blue.

FIG. 29 shows an ABNOVA box plot of individuals with IPA levels determined on serial samples over times of 6 months to 5 years. The P value for the null hypothesis (that the scatter in IPA values is within individuals and not due to individual specific differences) is $2.1*10exp-16$ which is a highly significant indication that I3PA is an individual specific characteristic over time FIG. 30 shows the results of a loading study of the I3PA derivative indole propionamide (IPAM) in the R6/2 HD mouse model from which we derived and developed methods for monitoring IPA levels in plasma and brain from urinary metabolites of IPA.

A cohort of R6/2 HD mice were dosed daily for 3 weeks intra peritoneal with 200 ug of the IPA derivative amide indole propionamide (IPAM) and compared with undosed R6/2 and their wild type littermates. Feces and urine were collected at the time of sacrifice and blood and brain after sacrifice. The data indicates:

1. That the brain and plasma levels correlate with urinary levels and thus animals can be tracked in a drug trial without sacrifice.
2. That IPAM is converted rapidly in the blood to IPA but less rapidly in the gut, resulting in levels in brain that correlate with plasma IPA levels suggesting that direct administration of IPA would be a better alternative than use of the derivative.
3. The R6/2 levels of IPA in brain and plasma are lower than in wild type mice. In this study although feces levels were lower the decrease was not significant.

In yet another aspect of the disclosure we provide a method for preparation of purified indole therapies. Indoles as a class are subject to degradation and contamination such as the problem encountered with preparations of tryptophan that were related to development basal eosinophilia. Nominally pure commercial sources of indoles when evaluated using ultra-sensitive LCECA techniques show traces of other compounds from the ug/mg to (pg/mg) levels (part per billion to sub part per trillion). These are potentially harmful. Pharmaceutical grade and supplemental tryptophan has now been brought to levels high purity that can be verified by LCECA. To take advantage of this we have developed a protocol for creating high concentrations of IPA using brewers yeast which also produces IPA with relatively good efficiency operating on a substrate of glucose and tryptophan. Brewers yeast as such is a common supplement and present as an extract in typical research mouse feed. Production of IPA in this matrix provides a highly purified IPA in a verifiably and long accepted matrix. As an example a preparation of 1 g of brewers yeast, 500 mg of glucose and 50 mg of tryptophan allowed to incubate to completion at room temperature (90-120 min) in 35 ml of distilled water yields ca. 3 mg of IPA. Passing the supernate through a 1 OK MW filter indicates that 75-80% of the IPA is coordinately bound to brewers yeast protein. The bound material is extractable in organic solvents but does not release significantly in HCl at concentrations found in the stomach. Protein bound IPA as a means of dosing in either animal or human trials allows the IPA to get to the Gut prior to being released from the protein and consequently provide both increased levels in plasma and potentiate changes in the aggregate gut microbiome. The process is inherently capable of scaling to any desired level.

The invention claimed is:

1. A method for treating an individual suffering from Huntington's disease, which comprises administering to said individual indole lactic acid or a mixture of indole-3-propionic acid and indole lactic acid or a salt or ester or protein complex or inorganically bound preparation thereof and a pharmaceutically acceptable carrier therefor, whereby to increase available levels of indole-3-propionic acid in the gut of the individual.

2. The method of claim 1, including the step of monitoring the efficacy of said administration by monitoring indole lactic acid or indole-3-propionic acid changes in the gut microbiome from a metabolomic profile reflecting an aggregate composition of the gut microbiome in the feces of said individual.

3. The method of claim 1, wherein the indole-3-propionic acid is administered as indole-3-propionic acid bound to a protein or indole-3-propionic acid bound to an inert material.

* * * * *